US005843725A

United States Patent [19]

Sledziewski et al.

[11] Patent Number: 5,843,725

[45] Date of Patent: *Dec. 1, 1998

[54] METHODS OF PRODUCING SECRETED RECEPTOR ANALOGS AND BIOLOGICALLY ACTIVE DIMERIZED POLYPEPTIDE FUSIONS

[75] Inventors: Andrzej Z. Sledziewski; Lillian Anne Bell; Wayne R. Kindsvogel, all of Seattle, Wash.

[73] Assignee: ZymoGenetics, Inc., Seattle, Wash.

[*] Notice: The term of this patent shall not extend beyond the expiration date of Pat. Nos. 5,155,027 and 5,750,375.

[21] Appl. No.: 475,458

[22] Filed: Jun. 7, 1995

Related U.S. Application Data

[62] Division of Ser. No. 180,195, Jan. 11, 1994, Pat. No. 5,567,584, which is a continuation of Ser. No. 634,510, Dec. 27, 1990, abandoned, which is a continuation-in-part of Ser. No. 347,291, May 2, 1989, Pat. No. 5,155,027, which is a continuation-in-part of Ser. No. 146,877, Jan. 22, 1988, abandoned.

[30] Foreign Application Priority Data

Jan. 18, 1989 [EP] European Pat. Off. ............... 8910087

[51] Int. Cl.$^6$ .............................. C12N 15/10; C12N 5/10; C07K 16/46; C07K 14/705
[52] U.S. Cl. .................... 435/69.7; 435/325; 435/320.1; 435/172.3; 530/387.1; 530/387.3; 530/333; 530/350; 530/399
[58] Field of Search ............................... 435/69.7, 320.1, 435/172.3, 325; 530/387.3, 399, 333, 350, 387.1

[56] References Cited

U.S. PATENT DOCUMENTS

| | | | |
|---|---|---|---|
| 4,474,893 | 10/1984 | Reading | 436/547 |
| 4,599,311 | 7/1986 | Kawasaki | 435/71 |
| 4,761,371 | 8/1988 | Bell et al. | 435/68 |
| 4,766,073 | 8/1988 | Murray et al. | 435/172.3 |
| 4,816,397 | 3/1989 | Boss et al. | 435/68 |
| 4,816,567 | 3/1989 | Cabilly et al. | 530/387 |
| 5,015,571 | 5/1991 | Niman et al. | 435/7.92 |
| 5,116,964 | 5/1992 | Capon et al. | 536/27 |
| 5,155,027 | 10/1992 | Sledziewski et al. | 435/69.7 |
| 5,169,939 | 12/1992 | Gefter et al. | 530/387.3 |
| 5,200,327 | 4/1993 | Garvin et al. | 435/69.5 |
| 5,567,584 | 10/1996 | Sledziewski et al. | 435/6 |

FOREIGN PATENT DOCUMENTS

| | | |
|---|---|---|
| 088 994 | 9/1983 | European Pat. Off. . |
| 116 201 | 8/1984 | European Pat. Off. . |
| 120 694 | 10/1984 | European Pat. Off. . |
| 162 319 | 11/1985 | European Pat. Off. . |
| 171 496 | 2/1986 | European Pat. Off. . |
| 173 494 | 3/1986 | European Pat. Off. . |
| 239 400 | 9/1987 | European Pat. Off. . |
| 244 221 A1 | 11/1987 | European Pat. Off. . |
| 256 654 | 2/1988 | European Pat. Off. . |
| 315 062 | 5/1989 | European Pat. Off. . |
| 327 369 A2 | 8/1989 | European Pat. Off. . |
| WO 86/01533 | 3/1986 | WIPO . |
| WO 90/06953 | 6/1990 | WIPO . |

OTHER PUBLICATIONS

Matsui et al., Isolation of a novel receptor cDNA establishes the existence of two PDGF receptor genes, Science, 243: 800–804, Feb. 1989.
Castanon et al., Cloning of human lysozyme gene and expression in the yeast *Saccharomyces cerevisiae,* Gene, 66: 223–234, Jun. 1988.
Schnee et al., Construction and expression of a recombinant antibody–targeted palsminogen activator, Proc. Natl. Acad. Sci. USA, 84: 6901–6908, Oct. 1987.
Bishayee et al., Ligand–induced dimerization of the platelet– derived growth factor receptor, J. Biol. Chem., 264: 11699–11705, Jul. 1989.
Kanakaraj et al., Ligand–induced interaction between alpha– and beta–type platelet–derived growth factor (PDGF) receptors, Biochem., 30: 1761–1767, 1991.
Heldin et al., Dimerization f B–type platelet–derived growth factor receptors occurs after ligand binding and is closely associated with receptor kinase activation, J. Biol. Chem., 264:8905–8912, May 1989.
Duan et al., A soluble extracellular region of the platelet–derived growth factor receptor (PDGF) antagonizes PDGF actions and dimerizes in response to PDGF, Clin. Res., 38(2): 407A, May 1990.
Heidaran et al., Role of alpha–beta receptor heterodimer formation in beta platelet–derived growth factor (PDGF) receptor aciviation by PDGF–AB, J. Biol. Chem., 266: 20232–20237, Oct. 1991.
Kuwana et al., *Biochemical and Biophysical Research Communications* 149(3): 960–968, 1987.
Yarden et al., *Nature 323*: 226–232, 1986.
Hart et al., *Science 240*: 1529–1531, 1988.
Escobedo et al., *Science 240*: 1532–1534, 1988.
Heldin et al., *EMBO J. 7*: 1387–1393, 1988.
Radeke et al, *Nature 325*: 593–597, 1987.
Ebina et al., *Cell 40*:747–758, 1985.
Rubin et al., *J.Immun. 135*: 3172–3177, 1985.
Ellis et al., *J. Cell. Biol. 150*: 14a, 1987.

(List continued on next page.)

*Primary Examiner*—Stephen Walsh
*Assistant Examiner*—Claire M. Kaufman
*Attorney, Agent, or Firm*—Townsend and Townsend and Crew

[57] ABSTRACT

Methods for producing secreted receptor analogs and biologically active peptide dimers are disclosed. The methods for producing secreted receptor analogs and biologically active peptide dimers utilize a DNA sequence encoding a receptor analog or a peptide requiring dimerization for biological activity joined to a dimerizing protein. The receptor analog includes a ligand-binding domain. Polypeptides comprising essentially the extracellular domain of a human PDGF receptor fused to dimerizing proteins, the portion being capable of binding human PDGF or an isoform thereof, are also disclosed. The polypeptides may be used within methods for determining the presence of and for purifying human PDGF or isoforms thereof.

49 Claims, 18 Drawing Sheets

OTHER PUBLICATIONS

Smith et al., *Science 238*: 1704–1707, 1987.
Livneh et al., *J. Biol. Chem. 261*: 12490–12497, 1986.
Boni–Schnetzler and Pilch, *Proc. Natl. Acad. Sci. USA 84*: 7832–7836, 1987.
Claesson–Welsh et al., *Mol. Cell. Biol. 8*: 3476–3486, 1988.
Ullrich et al., *Nature 309*: 418–425, 1984.
Ullrich et al., *Nature 313*:756–761, 1985.
Derynck et al., *Nature 316*:701–705, 1985.
Loh et al., *Cell 33*:85–93, 1983.
Honjo et al., *Cell 18*: 559–568, 1979.
Alber and Kawasaki, *J. Mol. Appl. Genet. 1*: 419–434, 1982.
Russell et al., *Nature 304*: 652–654, 1983.
Grosschedl and Baltimore, *Cell 41*: 885–897, 1985.
Hieter et al., *Cell 22*: 197–207, 1980.
Treiger et al., *J. Immunol. 136*: 4099–4105, 1986.
Roth et al., *J. Cell. Biol. 102*: 1271–1283, 1986.
Riedel et al., *Science 236*: 197–200, 1987.
Rieldel et al., *Nature 324*: 68–70, 1986.
Gascoigne et al., *Proc. Natl. Acad. Sci. USA 84*: 2936–2940, 1987.
Maddon et al., *Cell 47*: 333–348, 1986.
Maddon et al., *Cell 42*: 93–104, 1985.
Capon et al., *Nature 337*: 525–531, 1989.
Wood et al., *Nature 314*:446–449, 1985.
Carlson et al., *Mol. Cell. Biol. 3*: 439–447, 1983.
Marx, *Science 229*:455–456, 1985.
Neuberger et al., *Nature 312*: 604–609, 1984.
Oi and Morrison, *Biotechniques 4*: 214–221, 1986.
Bailon et al., *Bio/Technology 5*: 1195–1198, 1987.
Ballou et al., *J. Biol. Chem. 255*: 5986–5991, 1980.
Munro and Pelham, *EMBO J. 3*: 3087–3093, 1984.
von Heijne, *Nucl Acids Res. 14*: 4683–4690, 1986.
von Heijne, *Eur. J. Biochem. 133*:17–21, 1983.
Beggs, *Nature*: 104–108, 1978.
Clarke et al., *Meth. Enzym. 68*: 436–442, 1979.
Mariuzza and Winter, *J. Biol. Chem. 264*: 7310–7316, 1989.
Gronwald et al., *Proc. Natl. Acad. Sci. USA 85*: 3435–3439, 1988.
Riedel et al., *Protein Engineering 1*(3): 237, 1987.

```
   1 GGCCCCTCAGCCCTGCTGCCCAGCACGAGCCTGTGCTCGCCCTGCCCAACGCAGACAGCCAGACCCAGG   69
  70 GCGGCCCCTCTGGCGGCTCTGCTCCTCCCGAAGGATGCTTGGGGAGTGAGGCGAAGCTGGGCGCTCCTC  138
 139 TCCCCTACAGCAGCCCCCTTCCTCCATCCCTCTGTTCTCCTGAGCCTTCAGGAGCCTGCACCAGTCCTG  207
 208 CCTGTCCTTCTACTCAGCTGTTACCCACTCTGGGACCAGCAGTCTTTCTGATAACTGGGAGAGGGCAGT  276
 277 AAGGAGGACTTCCTGGAGGGGGTGACTGTCCAGAGCCTGGAACTGTGCCCACACCAGAAGCCATCAGCA  345
 346 GCAAGGACACCATGCGGCTTCCGGGTGCGATGCCAGCTCTGGCCCTCAAAGGCGAGCTGCTGTTGCTGT  414
                  M   R   L   P   G   A   M   P   A   L   A   L   K   G   E   L   L   L   L   S    20
 415 CTCTCCTGTTACTTCTGGAACCACAGATCTCTCAGGGCCTGGTCGTCACACCCCGGGGCCAGAGCTTG   483
       L   L   L   L   L   E   P   Q   I   S   Q   G   L   V   V   T   P   P   G   P   E   L   V    43
 484 TCCTCAATGTCTCCAGCACCTTCGTTCTGACCTGCTCGGGTTCAGCTCCGGTGGTGTGGGAACGGATGT  552
       L   N   V   S   S   T   F   V   L   T   C   S   G   S   A   P   V   V   W   E   R   M   S    66
 553 CCCAGGAGCCCCCACAGGAAATGGCCAAGGCCCAGGATGGCACCTTCTCCAGCGTGCTCACACTGACCA  621
       Q   E   P   P   Q   E   M   A   K   A   Q   D   G   T   F   S   S   V   L   T   L   T   N    89
 622 ACCTCACTGGGCTAGACACGGGAGAATACTTTTGCACCCACAATGACTCCCGTGGACTGGAGACCGATG  690
       L   T   G   L   D   T   G   E   Y   F   C   T   H   N   D   S   R   G   L   E   T   D   E   112
 691 AGCGGAAACGGCTCTACATCTTTGTGCCAGATCCCACCGTGGGCTTCCTCCCTAATGATGCCGAGGAAC  759
       R   K   R   L   Y   I   F   V   P   D   P   T   V   G   F   L   P   N   D   A   E   E   L   135
 760 TATTCATCTTTCTCACGGAAATAACTGAGATCACCATTCCATGCCGAGTAACAGACCCACAGCTGGTGG  828
       F   I   F   L   T   E   I   T   E   I   T   I   P   C   R   V   T   D   P   Q   L   V   V   158
 829 TGACACTGCACGAGAAGAAAGGGGACGTTGCACTGCCTGTCCCCTATGATCACCAACGTGGCTTTTCTG  897
       T   L   H   E   K   K   G   D   V   A   L   P   V   P   Y   D   H   Q   R   G   F   S   G   181
 898 GTATCTTTGAGGACAGAAGCTACATCTGCAAAACCACCATTGGGGACAGGGAGGTGGATTCTGATGCCT  966
       I   F   E   D   R   S   Y   I   C   K   T   T   I   G   D   R   E   V   D   S   D   A   Y   204
 967 ACTATGTCTACAGACTCCAGGTGTCATCCATCAACGTCTCTGTGAACGCAGTGCAGACTGTGGTCCGCC 1035
       Y   V   V   Y   R   L   Q   V   S   S   I   N   V   S   V   N   A   V   Q   T   V   V   R   227
1036 AGGGTGAGAACATCACCCTCATGTGCATTGTGATCGGGAATGAGGTGGTCAACTTCGAGTGGACATACC 1104
       Q   G   E   N   I   T   L   M   C   I   V   I   G   N   E   V   V   N   F   E   W   T   Y   250
1105 CCCGCAAAGAAAGTGGGCGGCTGGTGGAGCCGGTGACTGACTTCCTCTTGGATATGCCTTACCACATCC 1173
       P   R   K   E   S   G   R   L   V   E   P   V   T   D   F   L   L   D   M   P   Y   H   I   273
1174 GCTCCATCCTGCACATCCCCAGTGCCGAGTTAGAAGACTCGGGGACCTACACCTGCAATGTGACGGAGA 1242
       R   S   I   L   H   I   P   S   A   E   L   E   D   S   G   T   Y   T   C   N   V   T   E   296
1243 GTGTGAATGACCATCAGGATGAAAAGGCCATCAACATCACCGTGGTTGAGAGCGGCTACGTGCGGCTCC 1311
       S   V   N   D   H   Q   D   E   K   A   I   N   I   T   V   V   E   S   G   Y   V   R   L   319
```

*Fig. 1A*

```
1312 TGGGAGAGGTGGGCACACTACAATTTGCTGAGCTGCATCGGAGCCGGACACTGCAGGTAGTGTTCGAGG 1380
      G   E   V   G   T   L   Q   F   A   E   L   H   R   S   R   T   L   Q   V   V   F   E   A  342

1381 CCTACCCACCGCCCACTGTCCTGTGGTTCAAAGACAACCGCACCCTGGGCGACTCCAGCGCTGGCGAAA 1449
      Y   P   P   P   T   V   L   W   F   K   D   N   R   T   L   G   D   S   S   A   G   E   I  365

1450 TCGCCCTGTCCACGCGCAACGTGTCGGAGACCCGGTATGTGTCAGAGCTGACACTGGTTCGCGTGAAGG 1518
      A   L   S   T   R   N   V   S   E   T   R   Y   V   S   E   L   T   L   V   R   V   K   V  388

1519 TGGCAGAGGCTGGCCACTACACCATGCGGGCCTTCCATGAGGATGCTGAGGTCCAGCTCTCCTTCCAGC 1587
      A   E   A   G   H   Y   T   M'  R   A   F   H   E   D   A   E   V   Q   L   S   F   Q   L  411

1588 TACAGATCAATGTCCCTGTCCGAGTGCTGGAGCTAAGTGAGAGCCACCCTGACAGTGGGGAACAGACAG 1656
      Q   I   N   V   P   V   R   V   L   E   L   S   E   S   H   P   D   S   G   E   Q   T   V  434

1657 TCCGCTGTCGTGGCCGGGGCATGCCCCAGCCGAACATCATCTGGTCTGCCTGCAGAGACCTCAAAAGGT 1725
      R   C   R   G   R   G   M   P   Q   P   N   I   I   W   S   A   C   R   D   L   K   R   C  457

1726 GTCCACGTGAGCTGCCGCCCACGCTGCTGGGGAACAGTTCCGAAGAGGAGAGCCAGCTGGAGACTAACG 1794
      P   R   E   L   P   P   T   L   L   G   N   S   S   E   E   E   S   Q   L   E   T   N   V  480

1795 TGACGTACTGGGAGGAGGAGCAGGAGTTTGAGGTGGTGAGCACACTGCGTCTGCAGCACGTGGATCGGC 1863
      T   Y   W   E   E   E   Q   E   F   E   V   V   S   T   L   R   L   Q   H   V   D   R   P  503

1864 CACTGTCGGTGCGCTGCACGCTGCGCAACGCTGTGGGCCAGGACACGCAGGAGGTCATCGTGGTGCCAC 1932
      L   S   V   R   C   T   L   R   N   A   V   G   Q   D   T   Q   E   V   I   V   V   P   H  526

1933 ACTCCTTGCCCTTTAAGGTGGTGGTGATCTCAGCCATCCTGGCCCTGGTGGTGCTCACCATCATCTCCC 2001
      S   L   P   F   K   V   V   V   I   S   A   I   L   A   L   V   V   L   T   I   I   S   L  549

2002 TTATCATCCTCATCATGCTTTGGCAGAAGAAGCCACGTTACGAGATCCGATGGAAGGTGATTGAGTCTG 2070
      I   I   L   I   M   L   W   Q   K   K   P   R   Y   E   I   R   W   K   V   I   E   S   V  572

2071 TGAGCTCTGACGGCCATGAGTACATCTACGTGGACCCCATGCAGCTGCCCTATGACTCCACGTGGGAGC 2139
      S   S   D   G   H   E   Y   I   Y   V   D   P   M   Q   L   P   Y   D   S   T   W   E   L  595

2140 TGCCGCGGGACCAGCTTGTGCTGGGACGCACCCTCGGCTCTGGGGCCTTTGGGCAGGTGGTGGAGGCCA 2208
      P   R   D   Q   L   V   L   G   R   T   L   G   S   G   A   F   G   Q   V   V   E   A   T  618

2209 CGGCTCATGGCCTGAGCCATTCTCAGGCCACGATGAAAGTGGCCGTCAAGATGCTTAAATCCACAGCCC 2277
      A   H   G   L   S   H   S   Q   A   T   M   K   V   A   V   K   M   L   K   S   T   A   R  641

2278 GCAGCAGTGAGAAGCAAGCCCTTATGTCGGAGCTGAAGATCATGAGTCACCTTGGGCCCCACCTGAACG 2346
      S   S   E   K   Q   A   L   M   S   E   L   K   I   M   S   H   L   G   P   H   L   N   V  664

2347 TGGTCAACCTGTTGGGGGCCTGCACCAAAGGAGGACCCATCTATATCATCACTGAGTACTGCCGCTACG 2415
      V   N   L   L   G   A   C   T   K   G   G   P   I   Y   I   I   T   E   Y   C   R   Y   G  687

2416 GAGACCTGGTGGACTACCTGCACCGCAACAAACACACCTTCCTGCAGCACCACTCCGACAAGCGCCGCC 2484
      D   L   V   D   Y   L   H   R   N   K   H   T   F   L   Q   H   H   S   D   K   R   R   P  710

2485 CGCCCAGCGCGGAGCTCTACAGCAATGCTCTGCCCGTTGGGCTCCCCCTGCCCAGCCATGTGTCCTTGA 2553
      P   S   A   E   L   Y   S   N   A   L   P   V   G   L   P   L   P   S   H   V   S   L   T  733
```

*Fig. 1B*

```
2554 CCGGGGAGAGCGACGGTGGCTACATGGACATGAGCAAGGACGAGTCGGTGGACTATGTGCCCATGCTGG 2622
      G   E   S   D   G   G   Y   M   D   M   S   K   D   E   S   V   D   Y   V   P   M   L   D  756

2623 ACATGAAAGGAGACGTCAAATATGCAGACATCGAGTCCTCCAACTACATGGCCCCTTACGATAACTACG 2691
      M   K   G   D   V   K   Y   A   D   I   E   S   S   N   Y   M   A   P   Y   D   N   Y   V  779

2692 TTCCCTCTGCCCCTGAGAGGACCTGCCGAGCAACTTTGATCAACGAGTCTCCAGTGCTAAGCTACATGG 2760
      P   S   A   P   E   R   T   C   R   A   T   L   I   N   E   S   P   V   L   S   Y   M   D  802

2761 ACCTCGTGGGCTTCAGCTACCAGGTGGCCAATGGCATGGAGTTTCTGGCCTCCAAGAACTGCGTCCACA 2829
      L   V   G   F   S   Y   Q   V   A   N   G   M   E   F   L   A   S   K   N   C   V   H   R  825

2830 GAGACCTGGCGGCTAGGAACGTGCTCATCTGTGAAGGCAAGCTGGTCAAGATCTGTGACTTTGGCCTGG 2898
      D   L   A   A   R   N   V   L   I   C   E   G   K   L   V   K   I   C   D   F   G   L   A  848

2899 CTCGAGACATCATGCGGGACTCGAATTACATCTCCAAAGGCAGCACCTTTTTGCCTTTAAAGTGGATGG 2967
      R   D   I   M   R   D   S   N   Y   I   S   K   G   S   T   F   L   P   L   K   W   M   A  871

2968 CTCCGGAGAGCATCTTCAACAGCCTCTACACCACCCTGAGCGACGTGTGGTCCTTCGGGATCCTGCTCT 3036
      P   E   S   I   F   N   S   L   Y   T   T   L   S   D   V   W   S   F   G   I   L   L   W  894

3037 GGGAGATCTTCACCTTGGGTGGCACCCCTTACCCAGAGCTGCCCATGAACGAGCAGTTCTACAATGCCA 3105
      E   I   F   T   L   G   G   T   P   Y   P   E   L   P   M   N   E   Q   F   Y   N   A   I  917

3106 TCAAACGGGGTTACCGCATGGCCCAGCCTGCCCATGCCTCCGACGAGATCTATGAGATCATGCAGAAGT 3174
      K   R   G   Y   R   M   A   Q   P   A   H   A   S   D   E   I   Y   E   I   M   Q   K   C  940

3175 GCTGGGAAGAGAAGTTTGAGATTCGGCCCCCCTTCTCCCAGCTGGTGCTGCTTCTCGAGAGACTGTTGG 3243
      W   E   E   K   F   E   I   R   P   P   F   S   Q   L   V   L   L   L   E   R   L   L   G  963

3244 GCGAAGGTTACAAAAAGAAGTACCAGCAGGTGGATGAGGAGTTTCTGAGGAGTGACCACCCAGCCATCC 3312
      E   G   Y   K   K   K   Y   Q   Q   V   D   E   E   F   L   R   S   D   H   P   A   I   L  986

3313 TTCGGTCCCAGGCCCGCTTGCCTGGGTTCCATGGCCTCCGATCTCCCCTGGACACCAGCTCCGTCCTCT 3381
      R   S   Q   A   R   L   P   G   F   H   G   L   R   S   P   L   D   T   S   S   V   L   Y 1009

3382 ATACTGCCGTGCAGCCCAATGAGGGTGACAACGACTATATCATCCCCCTGCCTGACCCCAAACCCGAGG 3450
      T   A   V   Q   P   N   E   G   D   N   D   Y   I   I   P   L   P   D   P   K   P   E   V 1032

3451 TTGCTGACGAGGGCCCACTGGAGGGTTCCCCCAGCCTAGCCAGCTCCACCCTGAATGAAGTCAACACCT 3519
      A   D   E   G   P   L   E   G   S   P   S   L   A   S   S   T   L   N   E   V   N   T   S 1055

3520 CCTCAACCATCTCCTGTGACAGCCCCCTGGAGCCCCAGGACGAACCAGAGCCAGAGCCCCAGCTTGAGC 3588
      S   T   I   S   C   D   S   P   L   E   P   Q   D   E   P   E   P   E   P   Q   L   E   L 1078

3589 TCCAGGTGGAGCCGGAGCCAGAGCTGGAACAGTTGCCGGATTCGGGGTGCCCTGCGCCTCGGGCGGAAG 3657
      Q   V   E   P   E   P   E   L   E   Q   L   P   D   S   G   C   P   A   P   R   A   E   A 1101

3658 CAGAGGATAGCTTCCTGTAGGGGGCTGGCCCCTACCCTGCCCTGCCTGAAGCTCCCCCCCTGCCAGCAC 3726
      E   D   S   F   L   .                                                                     1106

3727 CCAGCATCTCCTGGCCTGGCCTGACCGGGCTTCCTGTCAGCCAGGCTGCCCTTATCAGCTGTCCCCTTC 3795
```

*Fig. 1C*

```
3796 TGGAAGCTTTCTGCTCCTGACGTGTTGTGCCCCAAACCCTGGGGCTGGCTTAGGAGGCAAGAAAACTGC 3864
3865 AGGGGCCGTGACCAGCCCTCTGCCTCCAGGGAGGCCAACTGACTCTGAGCCAGGGTTCCCCCAGGGAAC 3933
3934 TCAGTTTTCCCATATGTAAGATGGGAAAGTTAGGCTTGATGACCCAGAATCTAGGATTCTCTCCCTGGC 4002
4003 TGACACGGTGGGGAGACCGAATCCCTCCCTGGGAAGATTCTTGGAGTTACTGAGGTGGTAAATTAACAT 4071
4072 TTTTTCTGTTCAGCCAGCTACCCCTCAAGGAATCATAGCTCTCTCCTCGCACTTTTTATCCACCCAGGA 4140
4141 GCTAGGGAAGAGACCCTAGCCTCCCTGGCTGCTGGCTGAGCTAGGGCCTAGCTTGAGCAGTGTTGCCTC 4209
4210 ATCCAGAAGAAAGCCAGTCTCCTCCCTATGATGCCAGTCCCTGCGTTCCCTGGCCCGAGCTGGTCTGGG 4278
4279 GCCATTAGGCAGCCTAATTAATGCTGGAGGCTGAGCCAAGTACAGGACACCCCCAGCCTGCAGCCCTTG 4347
4348 CCCAGGGCACTTGGAGCACACGCAGCCATAGCAAGTGCCTGTGTCCCTGTCCTTCAGGCCCATCAGTCC 4416
4417 TGGGGCTTTTTCTTTATCACCCTCAGTCTTAATCCATCCACCAGAGTCTAGAAGGCCAGACGGGCCCCG 4485
4486 CATCTGTGATGAGAATGTAAATGTGCCAGTGTGGAGTGGCCACGTGTGTGTGCCAGTATATGGCCCTGG 4554
4555 CTCTGCATTGGACCTGCTATGAGGCTTTGGAGGAATCCCTCACCCTCTCTGGGCCTCAGTTTCCCCTTC 4623
4624 AAAAAATGAATAAGTCGGACTTATTAACTCTGAGTGCCTTGCCAGCACTAACATTCTAGAGTATTCCAG 4692
4693 GTGGTGCACATTTGTCCAGATGAAGCAAGGCCTATACCCTAAACTTCATCCTGGGGGTCAGCTGGGCTC 4761
4762 CTGGGAGATTCCAGATCACACATCACACTCTGGGGACTCAGGAACCATGCCCCTTCCCCAGGCCCCCAG 4830
4831 CAAGTCTCAAGAACACAGCTGCACAGGCCTTGACTTAGAGTGACAGCCGGTGTCCTGGAAAGCCCCAAG 4899
4900 CAGCTGCCCCAGGGACATGGGAAGACCACGGGACCTCTTTCACTACCCACGATGACCTCCGGGGGTATC 4968
4969 CTGGGCAAAAGGGACAAAGAGGGCAAATGAGATCACCTCCTGCAGCCCACCACTCCAGCACCTGTGCCG 5037
5038 AGGTCTGCGTCGAAGACAGAATGGACAGTGAGGACAGTTATGTCTTGTAAAAGACAAGAAGCTTCAGAT 5106
5107 GGTACCCCAAGAAGGATGTGAGAGGTGGCTGCTTTGGAGTTTGCCCCCTCACCCCACCAGCTGCCCCAT 5175
5176 CCCTGAGGCATGCGCTCCATGGGGGTATGGTTTTGTCACTGCCCAGACCTAGCAGTGACATCTCATTGT 5244
5245 CCCCAGCCCAGTGGGCATTGGAGGTGCCAGGGGAGTCAGGGTTGTAGCCAAGACGCCCCCGCACGGGGA 5313
5314 GGGTTGGGAAGGGGGTGCAGGAAGCTCAACCCCTCTGGGCACCAACCCTGCATTGCAGGTTGGCACCTT 5382
5383 ACTTCCCTGGGATCCCCAGAGTTGGTCCAAGGAGGGAGAGTGGGTTCTCAATACGGTACCAAAGATATA 5451
5452 ATCACCTAGGTTTACAAATATTTTTAGGACTCACGTTAACTCACATTTATACAGCAGAAATGCTATTTT 5520
5521 GTATGCTGTTAAGTTTTTCTATCTGTGTACTTTTTTTTAAGGGAAAGATTTT 5572
```

```
  1  GCCCTGGGGACGGACCGTGGGCGGCGCGCAGCGGCGGGACGCGTTTTGGGGACGTGGTGGCCAGCGCCT
 70  TCCTGCAGACCCACAGGGAAGTACTCCCTTTGACCTCCGGGGAGCTGCGACCAGGTTATACGTTGCTGG

139  TGGAAAAGTGACAATTCTAGGAAAAGAGCTAAAAGCCGGATCGGTGACCGAAAGTTTCCCAGAGCTATG
                                                                       M
                                                                       1

208  GGGACTTCCCATCCGGCGTTCCTGGTCTTAGGCTGTCTTCTCACAGGGCTGAGCCTAATCCTCTGCCAG
      G  T  S  H  P  A  F  L  V  L  G  C  L  L  T  G  L  S  L  I  L  C  Q

277  CTTTCATTACCCTCTATCCTTCCAAATGAAAATGAAAAGGTTGTGCAGCTGAATTCATCCTTTTCTCTG
      L  S  L  P  S  I  L  P  N  E  N  E  K  V  V  Q  L  N  S  S  F  S  L

346  AGATGCTTTGGGGAGAGTGAAGTGAGCTGGCAGTACCCCATGTCTGAAGAAGAGAGCTCCGATGTGGAA
      R  C  F  G  E  S  E  V  S  W  Q  Y  P  M  S  E  E  E  S  S  D  V  E

415  ATCAGAAATGAAGAAAACAACAGCGGCCTTTTTGTGACGGTCTTGGAAGTGAGCAGTGCCTCGGCGGCC
      I  R  N  E  E  N  N  S  G  L  F  V  T  V  L  E  V  S  S  A  S  A  A

484  CACACAGGGTTGTACACTTGCTATTACAACCACACTCAGACAGAAGAGAATGAGCTTGAAGGCAGGCAC
      H  T  G  L  Y  T  C  Y  Y  N  H  T  Q  T  E  E  N  E  L  E  G  R  H

553  ATTTACATCTATGTGCCAGACCCAGATGTAGCCTTTGTACCTCTAGGAATGACGGATTATTTAGTCATC
      I  Y  I  Y  V  P  D  P  D  V  A  F  V  P  L  G  M  T  D  Y  L  V  I

622  GTGGAGGATGATGATTCTGCCATTATACCTTGTCGCACAACTGATCCCGAGACTCCTGTAACCTTACAC
      V  E  D  D  D  S  A  I  I  P  C  R  T  T  D  P  E  T  P  V  T  L  H

691  AACAGTGAGGGGGTGGTACCTGCCTCCTACGACAGCAGACAGGGCTTTAATGGGACCTTCACTGTAGGG
      N  S  E  G  V  V  P  A  S  Y  D  S  R  Q  G  F  N  G  T  F  T  V  G

760  CCCTATATCTGTGAGGCCACCGTCAAAGGAAAGAAGTTCCAGACCATCCCATTTAATGTTTATGCTTTA
      P  Y  I  C  E  A  T  V  K  G  K  K  F  Q  T  I  P  F  N  V  Y  A  L

829  AAAGCAACATCAGAGCTGGATCTAGAAATGGAAGCTCTTAAAACCGTGTATAAGTCAGGGGAAACGATT
      K  A  T  S  E  L  D  L  E  M  E  A  L  K  T  V  Y  K  S  G  E  T  I

898  GTGGTCACCTGTGCTGTTTTTAACAATGAGGTGGTTGACCTTCAATGGACTTACCCTGGAGAAGTGAAA
      V  V  T  C  A  V  F  N  N  E  V  V  D  L  Q  W  T  Y  P  G  E  V  K
```

Figure 11B

```
 967  GGCAAAGGCATCACAATACTGGAAGAAATCAAAGTCCCATCCATCAAATTGGTGTACACTTTGACGGTC
      G  K  G  I  T  I  L  E  E  I  K  V  P  S  I  K  L  V  Y  T  L  T  V

1036  CCCGAGGCCACGGTGAAAGACAGTGGAGATTACGAATGTGCTGCCCGCCAGGCTACCAGGGAGGTCAAA
      P  E  A  T  V  K  D  S  G  D  Y  E  C  A  A  R  Q  A  T  R  E  V  K

1105  GAAATGAAGAAAGTCACTATTTCTGTCCATGAGAAAGGTTTCATTGAAATCAAACCCACCTTCAGCCAG
      E  M  K  K  V  T  I  S  V  H  E  K  G  F  I  E  I  K  P  T  F  S  Q

1174  TTGGAAGCTGTCAACCTGCATGAAGTCAAACATTTTGTTGTAGAGGTGCGGGCCTACCCACCTCCCAGG
      L  E  A  V  N  L  H  E  V  K  H  F  V  V  E  V  R  A  Y  P  P  P  R

1243  ATATCCTGGCTGAAAAACAATCTGACTCTGATTGAAAATCTCACTGAGATCACCACTGATGTGGAAAAG
      I  S  W  L  K  N  N  L  T  L  I  E  N  L  T  E  I  T  T  D  V  E  K

1312  ATTCAGGAAATAAGGTATCGAAGCAAATTAAAGCTGATCCGTGCTAAGGAAGAAGACAGTGGCCATTAT
      I  Q  E  I  R  Y  R  S  K  L  K  L  I  R  A  K  E  E  D  S  G  H  Y

1381  ACTATTGTAGCTCAAAATGAAGATGCTGTGAAGAGCTATACTTTTGAACTGTTAACTCAAGTTCCTTCA
      T  I  V  A  Q  N  E  D  A  V  K  S  Y  T  F  E  L  L  T  Q  V  P  S

1450  TCCATTCTGGACTTGGTCGATGATCACCATGGCTCAACTGGGGGACAGACGGTGAGGTGCACAGCTGAA
      S  I  L  D  L  V  D  D  H  H  G  S  T  G  G  Q  T  V  R  C  T  A  E

1519  GGCACGCCGCTTCCTGATATTGAGTGGATGATATGCAAAGATATTAAGAAATGTAATAATGAAACTTCC
      G  T  P  L  P  D  I  E  W  M  I  C  K  D  I  K  K  C  N  N  E  T  S

1588  TGGACTATTTTGGCCAACAATGTCTCAAACATCATCACGGAGATCCACTCCCGAGACAGGAGTACCGTG
      W  T  I  L  A  N  N  V  S  N  I  I  T  E  I  H  S  R  D  R  S  T  V

1657  GAGGGCCGTGTGACTTTCGCCAAAGTGGAGGAGACCATCGCCGTGCGATGCCTGGCTAAGAATCTCCTT
      E  G  R  V  T  F  A  K  V  E  E  T  I  A  V  R  C  L  A  K  N  L  L

1726  GGAGCTGAGAACCGAGAGCTGAAGCTGGTGGCTCCCACCCTGCGTTCTGAACTCACGGTGGCTGCTGCA
      G  A  E  N  R  E  L  K  L  V  A  P  T  L  R  S  E  L  T  V  A  A  A

1795  GTCCTGGTGCTGTTGGTGATTGTGATCATCTCACTTATTGTCCTGGTTGTCATTTGGAAACAGAAACCG
      V  L  V  L  L  V  I  V  I  I  S  L  I  V  L  V  V  I  W  K  Q  K  P
```

Figure 11C

```
1864  AGGTATGAAATTCGCTGGAGGGTCATTGAATCAATCAGCCCGGATGGACATGAATATATTTATGTGGAC
      R  Y  E  I  R  W  R  V  I  E  S  I  S  P  D  G  H  E  Y  I  Y  V  D

1933  CCGATGCAGCTGCCTTATGACTCAAGATGGGAGTTTCCAAGAGATGGACTAGTGCTTGGTCGGGTCTTG
      P  M  Q  L  P  Y  D  S  R  W  E  F  P  R  D  G  L  V  L  G  R  V  L

2002  GGGTCTGGAGCGTTTGGGAAGGTGGTTGAAGGAACAGCCTATGGATTAAGCCGGTCCCAACCTGTCATG
      G  S  G  A  F  G  K  V  V  E  G  T  A  Y  G  L  S  R  S  Q  P  V  M

2071  AAAGTTGCAGTGAAGATGCTAAAACCCACGGCCAGATCCAGTGAAAAACAAGCTCTCATGTCTGAACTG
      K  V  A  V  K  M  L  K  P  T  A  R  S  S  E  K  Q  A  L  M  S  E  L

2140  AAGATAATGACTCACCTGGGGCCACATTTGAACATTGTAAACTTGCTGGGAGCCTGCACCAAGTCAGGC
      K  I  M  T  H  L  G  P  H  L  N  I  V  N  L  L  G  A  C  T  K  S  G

2209  CCCATTTACATCATCACAGAGTATTGCTTCTATGGAGATTTGGTCAACTATTTGCATAAGAATAGGGAT
      P  I  Y  I  I  T  E  Y  C  F  Y  G  D  L  V  N  Y  L  H  K  N  R  D

2278  AGCTTCCTGAGCCACCACCCAGAGAAGCCAAAGAAAGAGCTGGATATCTTTGGATTGAACCCTGCTGAT
      S  F  L  S  H  H  P  E  K  P  K  K  E  L  D  I  F  G  L  N  P  A  D

2347  GAAAGCACACGGAGCTATGTTATTTTATCTTTTGAAAACAATGGTGACTACATGGACATGAAGCAGGCT
      E  S  T  R  S  Y  V  I  L  S  F  E  N  N  G  D  Y  M  D  M  K  Q  A

2416  GATACTACACAGTATGTCCCCATGCTAGAAAGGAAAGAGGTTTCTAAATATTCCGACATCCAGAGATCA
      D  T  T  Q  Y  V  P  M  L  E  R  K  E  V  S  K  Y  S  D  I  Q  R  S

2485  CTCTATGATCGTCCAGCCTCATATAAGAAGAAATCTATGTTAGACTCAGAAGTCAAAAACCTCCTTTCA
      L  Y  D  R  P  A  S  Y  K  K  K  S  M  L  D  S  E  V  K  N  L  L  S

2554  GATGATAACTCAGAAGGCCTTACTTTATTGGATTTGTTGAGCTTCACCTATCAAGTTGCCCGAGGAATG
      D  D  N  S  E  G  L  T  L  L  D  L  L  S  F  T  Y  Q  V  A  R  G  M

2623  GAGTTTTTGGCTTCAAAAAATTGTGTCCACCGTGATCTGGCTGCTCGCAACGTCCTCCTGGCACAAGGA
      E  F  L  A  S  K  N  C  V  H  R  D  L  A  A  R  N  V  L  L  A  Q  G

2692  AAAATTGTGAAGATCTGTGACTTTGGCCTGGCCAGAGACATCATGCATGATTCGAACTATGTGTCGAAA
      K  I  V  K  I  C  D  F  G  L  A  R  D  I  M  H  D  S  N  Y  V  S  K

2761  GGCAGTACCTTTCTGCCCGTGAAGTGGATGGCTCCTGAGAGCATCTTTGACAACCTCTACACCACACTG
      G  S  T  F  L  P  V  K  W  M  A  P  E  S  I  F  D  N  L  Y  T  T  L
```

Figure 11D

```
2830  AGTGATGTCTGGTCTTATGGCATTCTGCTCTGGGAGATCTTTTCCCTTGGTGGCACCCCTTACCCCGGC
       S  D  V  W  S  Y  G  I  L  L  W  E  I  F  S  L  G  G  T  P  Y  P  G

2899  ATGATGGTGGATTCTACTTTCTACAATAAGATCAAGAGTGGGTACCGGATGGCCAAGCCTGACCACGCT
       M  M  V  D  S  T  F  Y  N  K  I  K  S  G  Y  R  M  A  K  P  D  H  A

2968  ACCAGTGAAGTCTACGAGATCATGGTGAAATGCTGGAACAGTGAGCCGGAGAAGAGACCCTCCTTTTAC
       T  S  E  V  Y  E  I  M  V  K  C  W  N  S  E  P  E  K  R  P  S  F  Y

3037  CACCTGAGTGAGATTGTGGAGAATCTGCTGCCTGGACAATATAAAAAGAGTTATGAAAAAATTCACCTG
       H  L  S  E  I  V  E  N  L  L  P  G  Q  Y  K  K  S  Y  E  K  I  H  L

3106  GACTTCCTGAAGAGTGACCATCCTGCTGTGGCACGCATGCGTGTGGACTCAGACAATGCATACATTGGT
       D  F  L  K  S  D  H  P  A  V  A  R  M  R  V  D  S  D  N  A  Y  I  G

3175  GTCACCTACAAAAACGAGGAAGACAAGCTGAAGGACTGGGAGGGTGGTCTGGATGAGCAGAGACTGAGC
       V  T  Y  K  N  E  E  D  K  L  K  D  W  E  G  G  L  D  E  Q  R  L  S

3244  GCTGACAGTGGCTACATCATTCCTCTGCCTGACATTGACCCTGTCCCTGAGGAGGAGGACCTGGGCAAG
       A  D  S  G  Y  I  I  P  L  P  D  I  D  P  V  P  E  E  E  D  L  G  K

3313  AGGAACAGACACAGCTCGCAGACCTCTGAAGAGAGTGCCATTGAGACGGGTTCCAGCAGTTCCACCTTC
       R  N  R  H  S  S  Q  T  S  E  E  S  A  I  E  T  G  S  S  S  T  F

3382  ATCAAGAGAGAGGACGAGACCATTGAAGACATCGACATGATGGACGACATCGGCATAGACTCTTCAGAC
       I  K  R  E  D  E  T  I  E  D  I  D  M  M  D  D  I  G  I  D  S  S  D

3451  CTGGTGGAAGACAGCTTCCTGTAACTGGCGGATTCGAGGGGTTCCTTCCACTTCTGGGGCCACCTCTGG
       L  V  E  D  S  F  L
                        1089

3520  ATCCCGTTCAGAAAACCACTTTATTGCAATGCGGAGGTTGAGAGGAGGACTTGGTTGATGTTTAAAGAG
3589  AAGTTCCCAGCCAAGGGCCTCGGGGAGCGTTCTAAATATGAATGAATGGGATATTTTGAAATGAACTTT
3658  GTCAGTGTTGCCTCTTGCAATGCCTCAGTAGCATCTCAGTGGTGTGTGAAGTTTGGAGATAGATGGATA
3727  AGGGAATAATAGGCCACAGAAGGTGAACTTTGTGCTTCAAGGACATTGGTGAGAGTCCAACAGACACAA
3796  TTTATACTGCGACAGAACTTCAGCATTGTAATTATGTAAATAACTCTAACCAAGGCTGTGTTTAGATTG
3865  TATTAACTATCTTCTTTGGACTTCTGAAGAGACCACTCAATCCATCCTGTACTTCCCTCTTGAAACCTG
3934  ATGTAGCTGCTGTTGAACTTTTTAAAGAAGTGCATGAAAAACCATTTTTGAACCTTAAAAGGTACTGGT
4003  ACTATAGCATTTTGCTATCTTTTTTAGTGTTAAAGAGATAAAGAATAATAAG
```

METHODS OF PRODUCING SECRETED RECEPTOR ANALOGS AND BIOLOGICALLY ACTIVE DIMERIZED POLYPEPTIDE FUSIONS

This application is a divisional of U.S. application Ser. No. 08/180,195, filed Jan. 11, 1994, now U.S. Pat. No. 5,567,584, which is a continuation of U.S. application Ser. No. 07/634,510 filed Dec. 27, 1990, now abandoned, which is a continuation-in-part of U.S. application Ser. No. 07/347, 291, filed May 2, 1989, now U.S. Pat. No. 5,155,027, which is a continuation-in-part of U.S. application Ser. No. 07/146, 877, filed Jan. 22, 1988, now abandoned.

TECHNICAL FIELD

The present invention is generally directed toward the expression of proteins, and more specifically, toward the expression of growth factor receptor analogs and biologically active dimerized polypeptide fusions.

BACKGROUND OF THE INVENTION

In higher eucaryotic cells, the interaction between receptors and ligands (e.g., hormones) is of central importance in the transmission of and response to a variety of extracellular signals. It is generally accepted that hormones and growth factors elicit their biological functions by binding to specific recognition sites (receptors) in the plasma membranes of their target cells. Upon ligand binding, a receptor undergoes a conformational change, triggering secondary cellular responses that result in the activation or inhibition of intracellular processes. The stimulation or blockade of such an interaction by pharmacological means has important therapeutic implications for a wide variety of illnesses.

Ligands fall into two classes: those that have stimulatory activity, termed agonists; and those that block the effects elicited by the original ligands, termed antagonists. The discovery of agonists that differ in structure and composition from the original ligand may be medically useful. In particular, agonists that are smaller than the original ligand may be especially useful. The bioavailability of these smaller agonists may be greater than that of the original ligand. This may be of particular importance for topical applications and for instances when diffusion of the agonist to its target sites is inhibited by poor circulation. Agonists may also have slightly different spectra of biological activity and/or different potencies, allowing them to be used in very specific situations. Agonists that are smaller and chemically simpler than the native ligand may be produced in greater quantity and at lower cost. The identification of antagonists which specifically block, for example, growth factor receptors has important pharmaceutical applications. Antagonists that block receptors against the action of endogenous, native ligand may be used as therapeutic agents for conditions including atherosclerosis, autocrine tumors, fibroplasia and keloid formation.

The discovery of new ligands that may be used in pharmaceutical applications has centered around designing compounds by chemical modification, complete synthesis, and screening potential ligands by complex and costly screening procedures. The process of designing a new ligand usually begins with the alteration of the structure of the original effector molecule. If the original effector molecule is known to be chemically simple, for example, a catecholamine or prostaglandin, the task is relatively straightforward. However, if the ligand is structurally complex, for example, a peptide hormone or a growth factor, finding a molecule which is functionally equivalent to the original ligand becomes extremely difficult.

Currently, potential ligands are screened using radioligand binding methods (Lefkowitz et al., Biochem. Biophys. Res. Comm. 60: 703–709, 1974; Aurbach et al., Science 186: 1223–1225, 1974; Atlas et al., Proc. Natl. Acad. Sci. USA 71: 4246–4248, 1974). Potential ligands can be directly assayed by binding the radiolabeled compounds to responsive cells, to the membrane fractions of disrupted cells, or to solubilized receptors. Alternatively, potential ligands may be screened by their ability to compete with a known labeled ligand for cell surface receptors.

The success of these procedures depends on the availability of reproducibly high quality preparations of membrane fractions or receptor molecules, as well as the isolation of responsive cell lines. The preparation of membrane fractions and soluble receptor molecules involves extensive manipulations and complex purification steps. The isolation of membrane fractions requires gentle manipulation of the preparation, a procedure which does not lend itself to commercial production. It is very difficult to maintain high biological activity and biochemical purity of receptors when they are purified by classical protein chemistry methods. Receptors, being integral membrane proteins, require cumbersome purification procedures, which include the use of detergents and other solvents that interfere with their biological activity. The use of these membrane preparations in ligand binding assays typically results in low reproducibility due to the variability of the membrane preparations.

As noted above, ligand binding assays require the isolation of responsive cell lines. Often, only a limited subset of cells is responsive to a particular agent, and such cells may be responsive only under certain conditions. In addition, these cells may be difficult to grow in culture or may possess a low number of receptors. Currently available cell types responsive to platelet-derived growth factor (PDGF), for example, contain only a low number (up to $4 \times 10^5$; see Bowen-Pope and Ross, J. Biol. Chem. 257: 5161–5171, 1982) of receptors per cell, thus requiring large numbers of cells to assay PDGF analogs or antagonists.

Presently, only a few naturally-occurring secreted receptors, for example, the interleukin-2 receptor (IL-2-R) have been identified. Rubin et al. (J. Immun. 135: 3172–3177, 1985) have reported the release of large quantities of IL-2-R into the culture medium of activated T-cell lines. Bailon et al. (Bio/Technology 5: 1195–1198, 1987) have reported the use of a matrix-bound interleukin-2 receptor to purify recombinant interleukin-2.

Three other receptors have been secreted from mammalian cells. The insulin receptor (Ellis et al., J. Cell Biol. 150: 14a, 1987), the HIV-1 envelope glyco-protein cellular receptor CD4 (Smith et al., Science 238: 1704–1707, 1987), the murine IL-7 receptor (Cell 60: 941–951, 1990) and the epidermal growth factor (EGF) receptor (Livneh et al., J. Biol. Chem. 261: 12490–12497, 1986) have been secreted from mammalian cells using truncated cDNAs that encode portions of the extracellular domains.

Naturally-occurring, secreted receptors have not been widely identified, and there have been only a limited number of reports of secreted recombinant receptors. Secreted receptors may be used in a variety of assays, which include assays to determine the presence of ligand in biological fluids and assays to screen for potential agonists and antagonists. Current methods for ligand screening and ligand/receptor binding assays have been limited to those using preparations of whole cells or cell membranes for as a source for receptor molecules. The low reproducibility and high cost of producing such preparations does not lend itself to commercial production. There is therefore a need in the art for a method of producing secreted receptors. There is a further need in the art for an assay system that permits high volume screening of compounds that may act on higher eucaryotic cells via specific surface receptors. This assay system should be rapid, inexpensive and adaptable to high volume screening. The present invention discloses such a method and assay system, and further provides other related advantages.

DISCLOSURE OF INVENTION

Briefly stated, the present invention discloses methods for producing secreted receptor analogs, including receptor analogs and secreted platelet-derived growth factor receptor (PDGF-R) analogs. In addition, the present invention discloses methods for producing secreted biologically active dimerized polypeptide fusions.

Within one aspect of the invention a method for producing a secreted PDGF-R analog is disclosed, comprising (a) introducing into a eukaryotic host cell a DNA construct comprising a transcriptional promoter operatively linked to a secretory signal sequence followed downstream of and in proper reading frame with a DNA sequence encoding at least a portion of the ligand-binding domain of a PDGF-R, the portion including a ligand-binding domain; (b) growing the host cell in an appropriate growth medium under physiological conditions to allow the secretion of a PDGF-R analog encoded by said DNA sequence; and (c) isolating the PDGF-R analog from the host cell.

Within one embodiment of the present invention, a PDGF-R analog comprising the amino acid sequence of FIG. 1 (Sequence ID Numbers 1 and 2) from isoleucine, number 29, to methionine, number 441, is secreted. Within another embodiment, a PDGF-R analog comprising the amino acid sequence of FIG. 1 (Sequence ID Numbers 1 and 2) from isoleucine, number 29 to lysine, number 531 is secreted. Within yet another embodiment of the invention, a PDGF-R analog comprising the amino acid sequence of FIG. 11 (Sequence ID Numbers 35 and 36) from glutamine, number 24 to glutamic acid, number 524 is secreted.

Yet another aspect of the present invention discloses a method for producing a secreted, biologically active dimerized polypeptide fusion. The method generally comprises a) introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring dimerization for biological activity joined to a dimerizing protein; (b) growing the host cell in an appropriate growth medium under physiological conditions to allow the secretion of a dimerized polypeptide fusion encodes by said DNA sequence; and (c) isolating the biologically active dimerized polypeptide fusion from the host cell.

Within one embodiment, the dimerizing protein is yeast invertase. Within another embodiment, the dimerizing protein is at least a portion of an immunoglobulin light chain. Within another embodiment, the dimerizing protein is at least a portion of an immunoglobulin heavy chain.

In another aspect of the invention, a method is disclosed for producing a secreted, biologically active dimerized polypeptide fusion, comprising (a) introducing into a eukaryotic host cell a first DNA construct comprising a transcriptional promoter operatively linked to a first secretory signal sequence followed downstream by and in proper reading frame with a first DNA sequence encoding a non-immunoglobulin polypeptide requiring dimerization for biological activity joined to an immunoglobulin light chain constant region; (b) introducing into the host cell a second DNA construct comprising a transcriptional promoter operatively linked to a second secretory signal sequence followed downstream by and in proper reading frame with a second DNA sequence encoding an immunoglobulin heavy chain constant region domain selected from the group consisting of $C_H1$, $C_H2$, $C_H3$, and $C_H4$; (c) growing the host cell in an appropriate growth medium under physiological conditions to allow the secretion of a dimerized polypeptide fusion encoded by said first and second DNA sequences; and (d) isolating the dimerized polypeptide fusion from the host cell. In one embodiment, the second DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin heavy chain constant region.

In another aspect of the invention, a method is disclosed for producing a secreted, biologically active dimerized polypeptide fusion, comprising (a) introducing into a eukaryotic host cell a first DNA construct comprising a transcriptional promoter operatively linked to a first secretory signal sequence followed downstream by and in proper reading frame with a first DNA sequence encoding a non-immunoglobulin polypeptide requiring dimerization for biological activity joined to an immunoglobulin heavy chain constant region domain selected from the group consisting of $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding an immunoglobulin light chain constant region; (c) growing the host cell in an appropriate growth medium under physiological conditions to allow the secretion of a dimerized polypeptide fusion encoded by said first and second DNA sequences; and (d) isolating the dimerized polypeptide fusion from the host cell. In one embodiment, the first DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin light chain constant region.

In another aspect of the invention, a method is disclosed for producing a secreted, biologically active dimerized polypeptide fusion, comprising (a) introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring dimerization for biological activity joined to an immunoglobulin heavy chain constant region domain selected from the group consisting of $C_H1$, $C_H2$, $C_H3$, and $C_H4$; (b) growing the host cell in an appropriate growth medium under physiological conditions to allow the secretion of a dimerized polypeptide fusion encoded by said first and second DNA sequences; and (c) isolating the biologically active dimerized polypeptide fusion from the host cell. In one embodiment, the DNA sequence further encodes an immunoglobulin heavy chain hinge region wherein the hinge region is joined to the heavy chain constant region domain.

In another aspect of the invention, a method is disclosed for producing a secreted, biologically active dimerized polypeptide fusion, comprising (a) introducing into a eukaryotic host cell a first DNA construct comprising a transcriptional promoter operatively linked to a first secretory signal sequence followed downstream by and in proper reading frame with a first DNA sequence encoding a first polypeptide chain of a non-immunoglobulin polypeptide dimer requiring dimerization for biological activity joined to an immunoglobulin heavy chain constant region domain, selected from the group consisting of $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding a second polypeptide chain of the non-immunoglobulin polypeptide dimer joined to an immunoglobulin light chain constant region domain; (c) growing the host cell in an appropriate growth medium under physiological conditions to allow the secretion of a dimerized polypeptide fusion encoded by said first and second DNA sequences wherein said dimerized polypeptide fusion exhibits biological activity characteristic of said non-immunoglobulin polypeptide dimer; and (d) isolating the dimerized polypeptide fusion from the host cell. In one embodiment the first DNA sequence further encodes an immunoglobulin heavy chain hinge region domain wherein the hinge region is joined to the immunoglobulin heavy chain constant region domain.

Within one embodiment of the present invention, a biologically active dimerized polypeptide fusion comprising the amino acid sequence of FIG. 1 (Sequence ID Numbers 1 and 2) from isoleucine, number 29, to methionine, number 441, is secreted. Within another embodiment, a biologically active dimerized polypeptide fusion comprising the amino acid sequence of FIG. 1 (Sequence ID Numbers 1 and 2) from isoleucine, number 29 to lysine, number 531 is secreted. Within another embodiment of the invention, a biologically active dimerized polypeptide fusion comprising the amino acid sequence of FIG. 11 (Sequence ID Numbers 35 and 36) from glutamine, number 24 to glutamic acid, number 524 is secreted. Within yet another embodiment of the invention, a biologically active dimerized polypeptide fusion comprising the amino acid sequence of FIG. 1 (Sequence ID Numbers 1 and 2) from isoleucine, number 29 to lysine, number 531 dimerized to the amino acid sequence of FIG. 11 (Sequence ID Numbers 35 and 36) from glutamine, number 24 to glutamic acid, number 524 is secreted.

In yet another aspect of the invention, a method is disclosed for producing a secreted receptor analog, comprising (a) introducing into a eukaryotic host cell a DNA construct comprising a transcriptional promoter operatively linked to at least one secretory signal sequence followed downstream by and in proper reading frame with a DNA sequence encoding a ligand-binding domain of a receptor requiring dimerization for biological activity joined to a dimerizing protein; (b) growing the host cell in an appropriate growth medium under physiological conditions to allow the secretion of a receptor analog encoded by said DNA sequence; and (c) isolating the receptor analog from the host cell.

In yet another aspect of the invention, a method is disclosed for producing a secreted receptor analog, comprising (a) introducing into a eukaryotic host cell a first DNA construct comprising a transcriptional promoter operatively linked to a first secretory signal sequence followed downstream by and in proper reading frame with a first DNA sequence encoding a ligand-binding domain of a receptor requiring dimerization for biological activity joined to an immunoglobulin light chain constant region; (b) introducing into the host cell a second DNA construct comprising a transcriptional promoter operatively linked to a second secretory signal sequence followed downstream by and in proper reading frame with a second DNA sequence encoding an immunoglobulin heavy chain constant region domain, selected from the group consisting of $C_H1$, $C_H2$, $C_H3$, and $C_H4$; (c) growing the host cell in an appropriate growth medium under physiological conditions to allow the secretion of a receptor analog encoded by said first and second DNA sequences; and (d) isolating the receptor analog from the host cell. In one embodiment, the second DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin heavy chain constant region.

In another aspect of the invention, a method is disclosed for producing a secreted receptor analog, comprising (a) introducing into a eukaryotic host cell a DNA construct comprising a transcriptional promoter operatively linked to a secretory signal sequence followed downstream by and in proper reading frame with a DNA sequence encoding a ligand-binding domain of a receptor requiring dimerization for biological activity joined to an immunoglobulin heavy chain constant region domain, selected from the group $C_H1$, $C_H2$, $C_H3$, and $C_H4$; (b) growing the host cell in an appropriate growth medium under physiological conditions to allow the secretion of the receptor analog; and (c) isolating the receptor analog from the host cell. In one embodiment, the DNA sequence further encodes an immunoglobulin heavy chain hinge region wherein the hinge region is joined to the heavy chain constant region domain.

In another aspect of the invention, a method is disclosed for producing a secreted receptor analog, comprising (a) introducing into a eukaryotic host cell a first DNA construct comprising a transcriptional promoter operatively linked to a first secretory signal sequence followed downstream of and in proper reading frame with a first DNA sequence encoding a ligand-binding domain of a receptor requiring dimerization for biological activity joined to an immunoglobulin heavy chain constant region domain, selected from the group $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding an immunoglobulin light chain constant region; (c) growing the host cell in an appropriate growth medium under physiological conditions to allow the secretion of a receptor analog encoded by said first and second DNA sequences; and (d) isolating the receptor analog from the host cell. In one embodiment, the first DNA sequence further encodes an immunoglobulin heavy chain hinge region wherein the hinge region is joined to the heavy chain constant region domain. In a preferred embodiment, the second DNA sequence further encodes an immunoglobulin variable region joined upstream of and in proper reading frame with the immunoglobulin light chain constant region.

In another aspect of the invention, a method is disclosed for producing a secreted receptor analog, comprising (a) introducing into a eukaryotic host cell a first DNA construct comprising a transcriptional promoter operatively linked to a first secretory signal sequence followed downstream in proper reading frame by a first DNA sequence encoding a first polypeptide chain of a ligand-binding domain of a receptor requiring dimerization for biological activity joined to an immunoglobulin heavy chain constant region domain, selected from the group $C_H1$, $C_H2$, $C_H3$, and $C_H4$; (b) introducing into the host cell a second DNA construct comprising a transcriptional promoter operatively linked to a second secretory signal sequence followed downstream by and in proper reading frame with a second DNA sequence encoding a second polypeptide chain of the ligand-binding domain of said receptor joined to an immunoglobulin light chain constant region domain; (c) growing the host cell in an appropriate growth medium under physiological conditions to allow the secretion of a receptor analog encoded by said first and second DNA sequences; and (d) isolating the receptor analog from the host cell. In one embodiment the first DNA sequence further encodes an immunoglobulin heavy chain hinge region domain wherein the hinge region is joined to the immunoglobulin heavy chain constant region domain.

Host cells for use in the present invention include cultured mammalian cells and fungal cells. In a preferred embodiment strains of the yeast *Saccharomyces cerevisiae* are used as host cells. Within another preferred embodiment cultured rodent myeloma cells are used as host cells.

Within one embodiment of the present invention, a receptor analog is a PDGF-R analog comprising the amino acid sequence of FIG. 1 (Sequence ID Numbers 1 and 2) from isoleucine, number 29, to methionine, number 441. Within another embodiment a PDGF-R analog comprises the amino acid sequence of FIG. 1 (Sequence ID Numbers 1 and 2) from isoleucine, number 29, to lysine, number 531. Within another embodiment of the invention, a PDGF-R analog comprises the amino acid sequence of FIG. 11 (Sequence ID Numbers 35 and 36) from glutamine, number 24 to glutamic acid, number 524 is secreted. Within yet another embodiment of the invention, a PDGF-R analog comprises the amino acid sequence of FIG. 1 (Sequence ID Numbers 1 and 2) from isoleucine, number 29 to lysine, number 531 and the amino acid sequence of FIG. 11 (Sequence ID Numbers 35 and 36) from glutamine, number 24 to glutamic acid, number 524 is secreted.

PDGF-R analogs produced by the above-disclosed methods may be used, for instance, within a method for determining the presence of human PDGF or an isoform thereof in a biological sample.

A method for determining the presence of human PDGF or an isoform thereof in a biological sample is disclosed and comprises (a) incubating a polypeptide comprising a PDGF receptor analog fused to a dimerizing protein with a biological sample suspected of containing PDGF or an isoform thereof under conditions that allow the formation of receptor/ligand complexes; and (b) detecting the presence of receptor/ligand complexes, and therefrom determining the presence of PDGF or an isoform thereof. Suitable biological samples in this regard include blood, urine, plasma, serum, platelet and other cell lysates, platelet releasates, cell suspensions, cell-conditioned culture media, and chemically or physically separated portions thereof.

These and other aspects of the present invention will become evident upon reference to the following detailed description and attached drawings.

BRIEF DESCRIPTION OF THE DRAWINGS

FIGS. 1A–D (Sequence ID Numbers 1 and 2) illustrate the nucleotide sequence of a representative PDGF β-receptor cDNA and the derived amino acid sequence of the primary translation product and corresponds to Sequence ID Number 1). Numbers above the lines refer to the nucleotide sequence; numbers below the lines refer to the amino acid sequence.

FIGS. 11A–D illustrates the sequence of a representative PDGF $\alpha$-receptor cDNA and the deduced amino acid sequence (using standard one-letter codes) encoded by the cDNA and corresponds to Sequence ID Numbers 35 and 36. Numbers at the ends of the lines refer to nucleotide positions. Numbers below the sequence refer to amino acid positions.

DETAILED DESCRIPTION OF THE INVENTION

Figure 2:
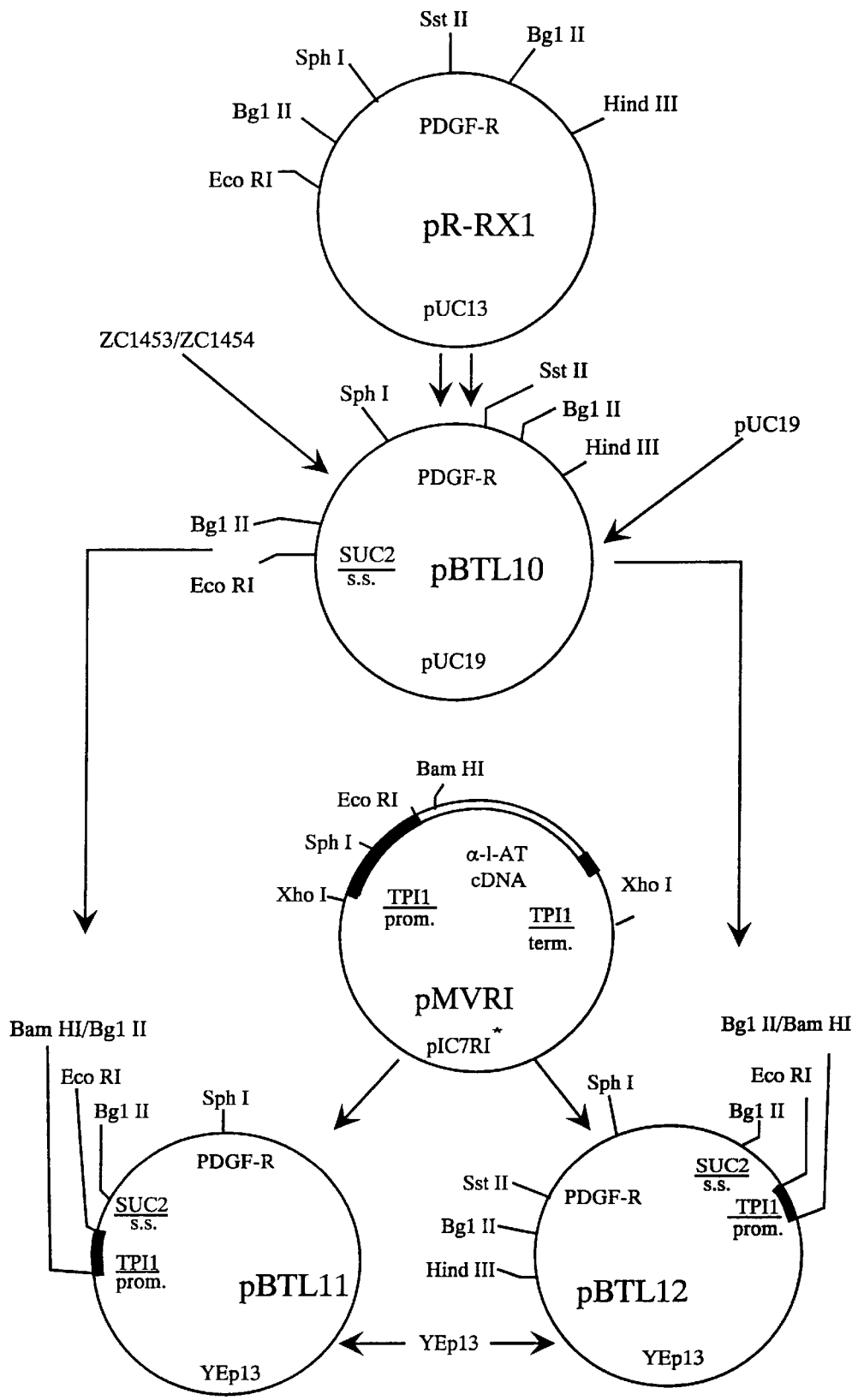
FIG. 2 illustrates the construction of pBTL10, pBTL11 and pBTL12.

Prior to setting forth the invention, it may be helpful to an understanding thereof to set forth definitions of certain terms to be used hereinafter.

DNA Construct: A DNA molecule, or a clone of such a molecule, either single- or double-stranded that has been modified through human intervention to contain segments of DNA combined and juxtaposed in a manner that as a whole would not otherwise exist in nature.

DNA constructs contain the information necessary to direct the expression and/or secretion of DNA sequences encoding polypeptides of interest. DNA constructs will generally include promoters, enhancers and transcription terminators. DNA constructs containing the information necessary to direct the secretion of a polypeptide will also contain at least one secretory signal sequence.

Secretory Signal Sequence: A DNA sequence encoding a secretory peptide. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly sythesized proteins. Very often the secretory peptide is cleaved from the mature protein during secretion. Such secretory peptides contain processing sites that allow cleavage of the signal peptides from the mature proteins as it passes through the secretory pathway. Processing sites may be encoded within the signal peptide or may be added to the signal peptide by, for example, in vitro mutagenesis. Certain secretory peptides may be used in concert to direct the secretion of polypeptides and proteins. One such secretory peptide that may be used in combination with other secretory peptides is the third domain of the yeast Barrier protein.

Receptor Analog: A non-immunoglobulin polypeptide comprising a portion of a receptor which is capable of binding ligand and/or is recognized by anti-receptor antibodies. The amino acid sequence of the receptor analog may contain additions, substitutions or deletions as compared to the native receptor sequence. A receptor analog may be, for example, the ligand-binding domain of a receptor joined to another protein. Platelet-derived growth factor receptor (PDGF-R) analogs may, for example, comprise a portion of a PDGF receptor capable of binding anti-PDGF receptor antibodies, PDGF, PDGF isoforms, PDGF analogs, or PDGF antagonists.

Dimerizing Protein: A polypeptide chain having affinity for a second polypeptide chain, such that the two chains associate under physiological conditions to form a dimer. The second polypeptide chain may be the same or a different chain.

Biological activity: A function or set of activities performed by a molecule in a biological context (i.e., in an organism or an in vitro facsimile thereof). Biological activities may include the induction of extracellular matrix secretion from responsive cell lines, the induction of hormone secretion, the induction of chemotaxis, the induction of mitogenesis, the induction of differentiation, or the inhibition of cell division of responsive cells. A recombinant protein or peptide is considered to be biologically active if it exhibits one or more biological activities of its native counterpart.

Ligand: A molecule capable of being bound by the ligand-binding domain of a receptor or by a receptor analog. The molecule may be chemically synthesized or may occur in nature. Ligands may be grouped into agonists and antagonists. Agonists are those molecules whose binding to a receptor induces the response pathway within a cell. Antagonists are those molecules whose binding to a receptor blocks the response pathway within a cell.

Joined: Two or more DNA coding sequences are said to be joined when, as a result of in-frame fusions between the DNA coding sequences or as a result of the removal of intervening sequences by normal cellular processing, the DNA coding sequences are translated into a polypeptide fusion.

As noted above, the present invention pr vides methods for producing biologically active dimerized polypeptide fusions and secreted receptor analogs, which include, for example, PDGF receptor analogs. Secreted receptor analogs may be used to screen for new compounds that act as agonists or antagonists when interacting with cells containing membrane-bound receptors. In addition, the methods of the present invention provide dimerized non-immunoglobulin polypeptide fusions of therapeutic value that are biologically active only as dimers. Moreover, the present invention provides methods of producing polypeptide dimers that are biologically active only as non-covalently associated dimers. Secreted, biologically active dimers that may be produced using the present invention include nerve growth factor, colony stimulating factor-1, factor XIII, and transforming growth factor β.

As used herein, the ligand-binding domain of a receptor is that portion of the receptor that is involved with binding the natural ligand. While not wishing to be bound by theory, the binding of a natural ligand to a receptor is believed to induce a conformational change which elicits a response to the change within the response pathway of the cell. For membrane-bound receptors, the ligand-binding domain is generally believed to comprise the extracellular domain for the receptor. The structure of receptors may be predicted from the primary translation products using the hydrophobicity plot function of, for example, P/C Gene or Intelligenetics Suite (Intelligenetics, Mt. View, Calif.) or may be predicted according to the methods described, for example, by Kyte and Doolittle, *J. Mol. Biol.* 157:105–132, 1982). The ligand-binding domain of the PDGF p-receptor, for example, has been predicted to include amino acids 29–531 of the published sequence (Gronwald et al., ibid.). The ligand-binding domain of the PDGF α-receptor has been predicted to include amino acids 25–500 of the published α-receptor sequence (Matsui et al., ibid.). As used herein, the ligand-binding domain of the PDGF β-receptor includes amino acids 29–441 of the sequence of FIGS. 1A and 1B (Sequence ID Number 1) and C-terminal extensions up to and including amino acid 531(FIG. 1B). The ligand-binding domain of the PDGF α-receptor is understood to include amino acids 24–524 of FIGS. 11A and 11B (Sequence ID Numbers 35 and 36).

Receptor analogs that may be used in the present invention include the ligand-binding domains of the epidermal growth factor receptor (EGF-R) and the insulin receptor. As used herein, a ligand-binding domain is that portion of the receptor that is involved in binding ligand and is generally a portion or essentially all of the extracellular domain that extends from the plasma membrane into the extracellular space. The ligand-binding domain of the EGF-R, for example, resides in the extracellular domain. EGF-R dimers have been found to exhibit higher ligand-binding affinity than EGF-R monomers (Boni-Schnetzler and Pilch, *Proc. Natl. Acad. Sci. USA* 84:7832–7836, 1987). The insulin receptor (Ullrich et al., *Nature* 313:756–761, 1985) requires dimerization for biological activity.

Another example of a receptor that may be secreted from a host cell is a platelet-derived growth factor receptor (PDGF-R). Two classes of PDGF-Rs, which recognized different isoforms of PDGF, have been identified. (PDGF is a disulfide-bonded, two-chain molecule, which is made up of an A chain and a B chain. These chains may be combined as AB heterodimers, AA homodimers or BB homodimers. These dimeric molecules are referred to herein as "isoforms".) The β-receptor (PDGFβ-R), which recognizes only the BB isoform of PDGF (PDGF-BB), has been described (Claesson-Welsh et al., *Mol. Cell. Biol.* 8:3476–3486, 1988; Gronwald et al., *Proc. Natl. Acad. Sci. USA* 85:3435–3439, 1988). The α-receptor (PDGFα-R), which recognizes all three PDGF isoforms (PDGF-AA, PDGF-AB and PDGF-BB), has been described by Matsui et al. (Science 243:800–804, 1989) and Kelly and Murray (pending commonly assigned U.S. patent application Ser.

No. 07/355,018, which is incorporated herein by reference). The primary translation products of these receptors indicate that each includes an extracellular domain implicated in the ligand-binding process, a transmembrane domain, and a cytoplasmic domain containing a tyrosine kinase activity.

The present invention provides a standardized assay system, not previously available in the art, for determining the presence of PDGF, PDGF isoforms, PDGF agonists or PDGF antagonists using a secreted PDGF receptor analogs. Such an assay system will typically involve combining the secreted PDGF receptor analog with a biological sample under physiological conditions which permit the formation of receptor-ligand complexes, followed by detecting the presence of the receptor-ligand complexes. The term physiological conditions is meant to include those conditions found within the host organism and include, for example, the conditions of osmolarity, salinity and pH. Detection may be achieved through the use of a label attached to the PDGF receptor analog or through the use of a labeled antibody which is reactive with the receptor analog or the ligand. A wide variety of labels may be utilized, such as radionuclides, fluorophores, enzymes and luminescers. Receptor-ligand complexes may also be detected visually, i.e., in immunoprecipitation assays which do not require the use of a label. This assay system provides secreted PDGF receptor analogs that may be utilized in a variety of screening assays for, for example, screening for analogs of PDGF. The present invention also provides a methods for measuring the level of PDGF and PDGF isoforms in biological fluids.

As noted above, the present invention provides methods for producing dimerized polypeptide fusions that require dimerization for biological activity or enhancement of biological activity. Polypeptides requiring dimerization for biological activity include, in addition to certain receptors, nerve growth factor, colony-stimulating factor-1 (CSF-1), transforming growth factor β (TGF-β), PDGF, and factor XIII. Nerve growth factor is a non-covalently linked dimer (Harper et al., *J. Biol. Chem.* 257: 8541–8548, 1982). CSF-1, which specifically stimulates the proliferation and differentiation of cells of mononuclear phagocytic lineage, is a disulfide-bonded homodimer (Retternmier et al., *Mol. Cell. Biol.* 7: 2378–2387, 1987). TGF-β is biologically active as a disulfide-bonded dimer (Assoian et al., *J. Biol. Chem.* 258: 7155–7160, 1983). Factor XIII is a plasma protein that exists as a two chain homodimer in its activated form (Ichinose et al., *Biochem.* 25: 6900– 6906, 1986). PDGF, as noted above, is a disulfide-bonded, two chain molecule (Murray et al., U.S. Pat. No. 4,766,073).

The present invention provides methods by which receptor analogs, including receptor analogs and PDGF-R analogs, requiring dimerization for activity may be secreted from host cells. The methods described herein are particularly advantageous in that they allow the production of large quantities of purified receptors. The receptors may be used in assays for the screening of potential ligands, in assays for binding studies, as imaging agents, and as agonists and antagonists within therapeutic agents.

A DNA sequence encoding a human PDGF receptor may be isolated as a cDNA using techniques known in the art (see, for example, Okayama and Berg, *Mol. Cell. Biol.* 2: 161–170, 1982; *Mol. Cell. Biol.* 3: 280–289, 1983) from a library of human genomic or cDNA sequences. Such libraries may be prepared by standard procedures, such as those disclosed by Gubler and Hoffman (*Gene* 25: 263–269, 1983). It is preferred that the molecule is a cDNA molecule because cDNA lack introns and are therefore more suited to manipulation and expression in transfected or transformed cells. Sources of mRNA for use in the preparation of a cDNA library include the MG-63 human osteosarcoma cell line (available from ATCC under accession number CRL 1427), diploid human dermal fibroblasts and human embryo fibroblast and brain cells (Matsui et al., ibid.). A cDNA encoding a PDGFβ-R has been cloned from a diploid human dermal fibroblast cDNA library using oligonucleotide probes complementary to sequences of the mouse PDGF receptor (Gronwald et al., ibid.). A PDGFα-R cDNA has been isolated by Matsui et al. (ibid.) from human embryo fibroblast and brain cells. Alternatively, a cDNA encoding a PDGFα-R may be isolated from a library prepared from MG-63 human osteosarcoma cells using a cDNA probe containing sequences encoding the transmembrane and cytoplasmic domains of the PDGFβ-R (described by Kelly and Murray, ibid.). Partial cDNA clones (fragments) can be extended by re-screening of the library with the cloned cDNA fragment until the full sequence is obtained. In one embodiment, a ligand-binding domain of a PDGF receptor is encoded by the sequence of FIGS. 1A and 1B (Sequence ID Number 1) from amino acid 29 through amino acid 441. In another embodiment, a ligand-binding domain of a PDGF receptor is encoded by the sequence of FIGS. 1A and 1B (Sequence ID Number 1) from amino acid 29 through amino acid 531. In yet another embodiment, a ligand-binding domain of a PDGF receptor is encoded by the sequence of FIGS. 11A and 11B (Sequence ID Numbers 35 and 36) from amino acid 24 through amino acid 524. One skilled in the art may envision the use of a smaller DNA sequence encoding the ligand-binding domain of a PDGF receptor containing at least 400 amino acids of the extracellular domain.

DNA sequences encoding EGF-R (Ullrich et al., *Nature* 304: 418–425, 1984), the insulin receptor (Ullrich et al., *Nature* 313: 756–761, 1985), nerve growth factor (Ullrich et al. *Nature* 303: 821–825, 1983), colony stimulating factor-1 (Rettenmier et al., ibid.), transforming growth factor β (Derynck et al., *Nature* 316: 701–705, 1985), PDGF (Murray et al., ibid.), and factor XIII (Ichinose et al., ibid.) may also be used within the present invention.

To direct polypeptides requiring dimerization for biological activity or receptor analogs into the secretory pathway of the host cell, at least one secretory signal sequence is used in conjunction with the DNA sequence of interest. Preferred secretory signals include the alpha factor signal sequence (pre-pro sequence) (Kurjan and Herkowitz, *Cell* 30: 933–943, 1982; Kurjan et al., U.S. Pat. No. 4,546,082; Brake, EP 116,201, 1983), the PHO5 signal sequence (Beck et al., WO 86/00637), the BAR1 secretory signal sequence (MacKay et al., U.S. Pat. No. 4,613,572; MacKay, WO 87/002670), immunoglobulin $V_H$ signal sequences (Loh et al., *Cell* 33: 85–93, 1983; Watson *Nuc. Acids. Res.* 12: 5145–5164, 1984) and immunoglobulin $V_\kappa$ signal sequences (Watson, ibid.). Particularly preferred signal sequences are the SUC2 signal sequence (Carlson et al., *Mol. Cell. Biol.* 3: 439–447, 1983) and PDGF receptor signal sequences. Alternatively, secretory signal sequences may be synthesized according to the rules established, for example, by von Heinje (*Eur. J. Biochem.* 133: 17–21, 1983; *J. Mol. Biol.* 184: 99–105, 1985; *Nuc. Acids. Res.* 14: 4683–3690, 1986).

Secretory signal sequences may be used singly or may be combined. For example, a first secretory signal sequence may be used singly or combined with a sequence encoding the third domain of Barrier (described in co-pending commonly assigned U.S. patent application Ser. No. 07/104,316, which is incorporated by reference herein in its entirety). The third domain of Barrier may be positioned in proper reading frame 3' of the DNA sequence of interest or 5' to the DNA sequence and in proper reading frame with both the secretory signal sequence and the DNA sequence of interest.

In one embodiment of the present invention, a sequence encoding a dimerizing protein is joined to a sequence encoding a polypeptide chain of a polypeptide dimer or a receptor analog, and this fused sequence is joined in proper reading frame to a secretory signal sequence. As shown herein, the present invention utilizes such an arrangement to drive the association of the polypeptide or receptor analog to form a biologically active molecule upon secretion. Suitable dimerizing proteins include the S. cerevisiae repressible acid phosphatase (Mizunaga et al., J. Biochem. (Tokyo) 103: 321–326, 1988), the S. cerevisiae type 1 killer preprotoxin (Sturley et al., EMBO J. 5: 3381–3390, 1986), the S. calsberaensis alpha galactosidase melibiase (Sumner-Smith et al., Gene 36: 333–340, 1985), the S. cerevisiae invertase (Carlson et al., Mol. Cell. Biol. 3: 439–447, 1983), the Neurospora crassa ornithine decarboxylase (Digangi et al., J. Biol. Chem. 262: 7889–7893, 1987), immunoglobulin heavy chain hinge regions (Takahashi et al., Cell 29: 671–679, 1982), and other dimerizing immunoglobulin sequences. In a preferred embodiment, S. cerevisiae invertase is used to drive the association of polypeptides into dimers. Portions of dimerizing proteins, such as those mentioned above, may be used as dimerizing proteins where those portions are capable of associating as a dimer in a covalent or noncovlent manner. Such portions may be determined by, for example, altering a sequence encoding a dimerizing protein through in vitro mutagenesis to delete portions of the coding sequence. These deletion mutants may be expressed in the appropriate host to determine which portions retain the capability of associating as dimers. Portions of immunoglobulin gene sequences may be used to drive the association of non-immunoglobulin polypeptides. These portions correspond to discrete domains of immunoglobulins. Immunoglobulins comprise variable and constant regions, which in turn comprise discrete domains that show similarity in their three-dimensional conformations. These discrete domains correspond to immunoglobulin heavy chain constant region domain exons, immunoglobulin heavy chain variable region domain exons, immunoglobulin light chain variable region domain exons and immunoglobulin light chain constant region domain exons in immunoglobulin genes (Hood et al., in Immunology, The Benjamin/Cummings Publishing Company, Inc., Menlo Park, Calif.; Honjo et al., Cell 18: 559–568, 1979; Takahashi et al., Cell 29: 671–679, 1982; and Honjo, Ann. Rev. Immun. 1:499–528, 1983)). Particularly preferred portions of immunoglobulin heavy chains include Fab and Fab' fragments. (An Fab fragment is a portion of an immunoglobulin heavy chain that includes a heavy chain variable region domain and a heavy chain constant region domain. An Fab' fragment is a portion of an immunoglobulin heavy chain that includes a heavy chain variable region domain, a heavy chain constant region domain and a heavy chain hinge region domain.)

It is preferred to use an immunoglobulin light chain constant region in association with at least one immunoglobulin heavy chain constant region domain. In another embodiment, an immunoglobulin light chain constant region is associated with at least one immunoglobulin heavy chain constant region domain joined to an immunoglobulin hinge region. In one set of embodiments, an immunoglobulin light chain constant region joined in frame with a polypeptide chain of a non-immunoglobulin polypeptide dimer or receptor analog and is associated with at least one heavy chain constant region. In a preferred set of embodiments a variable region is joined upstream of and in proper reading frame with at least one immunoglobulin heavy chain constant region. In another set of embodiments, an immunoglobulin heavy chain is joined in frame with a polypeptide chain of a non-immunoglobulin polypeptide dimer or receptor analog and is associated with an immunoglobulin light chain constant region. In yet another set of embodiments, a polypeptide chain of a non-immunoglobulin polypeptide dimer or receptor analog is joined to at least one immunoglobulin heavy chain constant region which is joined to an immunoglobulin hinge region and is associated with an immunoglobulin light chain constant region. In a preferred set of embodiments an immunoglobulin variable region is joined upstream of and in proper reading frame with the immunoglobulin light chain constant region.

Immunoglobulin heavy chain constant region domains include $C_H1$, $C_H2$, $C_H3$, and $C_H4$ of any class of immunoglobulin heavy chain including γ, α, ε, μ, and δ classes (Honjo, ibid., 1983) A particularly preferred immunoglobulin heavy chain constant region domain is human $C_H1$. Immunoglobulin variable regions include $V_H$, $V_κ$, or $V_λ$. DNA sequences encoding immunoglobulins may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA sequences (see, for example, Hieter et al., Cell 22: 197–207, 1980). Alternatively, the polymerase chain reaction (PCR) method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of ordinary skill in the art.

Host cells for use in practicing the present invention include eukaryotic cells capable of being transformed or transfected with exogenous DNA and grown in culture, such as cultured mammalian and fungal cells. Fungal cells, including species of yeast (e.g., Saccharomvces spp., Schizosaccharomyces spp.), or filamentous fungi (e.g., Aspergillus spp., Neurospora spp.) may be used as host cells within the present invention. Strains of the yeast Saccharomyces cerevisiae are particularly preferred.

Expression units for use in the present invention will generally comprise the following elements, operably linked in a 5' to 3' orientation: a transcriptional promoter, a secretory signal sequence a DNA sequence encoding non-immunoglobulin polypeptide requiring dimerization for biological activity joined to a dimerizing protein and a transcriptional terminator. The selection of suitable promoters, signal sequences and terminators will be determined by the selected host cell and will be evident to one skilled in the art and are discussed more specifically below.

Suitable yeast vectors for use in the present invention include YRp7 (Struhl et al., Proc. Natl. Acad. Sci. USA 76: 1035–1039, 1978), YEp13 (Broach et al., Gene 8: 121–133, 1979), pJDB249 and pJDB219 (Beggs, Nature 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., Gene 8: 17, 1979), HIS3 (Struhl et al., ibid.) or POT1 (Kawasaki and Bell, EP 171,142). Other suitable selectable markers include the CAT gene, which confers chloramphenicol resistance on yeast cells.

Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, New York, 1982; Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652–654, 1983 and Irani and Kilgore, described in pending, commonly assigned U.S. patent application Ser. No. 07/183,130, which is incorporated herein by reference). The expression units may also include a transcriptional terminator. A preferred transcriptional terminator is the TPI1 terminator (Alber and Kawasaki, ibid.).

In addition to yeast, proteins of the present invention can be expressed in filamentous fungi, for example, strains of the fungi Aspergillus (McKnight and Upshall, described in commonly assigned U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4: 2093–2099, 1985) and the tpiA promoter. An example of a suitable terminator is the ADH3 terminator (McKnight et al., ibid.). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75: 1929–1933, 1978), Yelton et al., (*Proc. Natl. Acad. Sci. USA* 81: 1740–1747, 1984), and Russell (*Nature* 301: 167–169, 1983). The genotype of the host cell will generally contain a genetic defect that is complemented by the selectable marker present on the expression vector. Choice of a particular host and selectable marker is well within the level of ordinary skill in the art.

In a preferred embodiment, a *Saccharomyces cerevisiae* host cell that contains a genetic deficiency in a gene required for asparagine-linked glycosylation of glycoproteins is used. Preferably, the *S. cerevisiae* host cell contains a genetic deficiency in the MNN9 gene (described in pending, commonly assigned U.S. patent application Ser. Nos. 116,095 and 189,547 which are incorporated by reference herein in their entirety). Most preferably, the *S. cerevisiae* host cell contains a disruption of the MNN9 gene. *S. cerevisiae* host cells having such defects may be prepared using standard techniques of mutation and selection. Ballou et al. (*J. Biol. Chem.* 255: 5986–5991, 1980) have described the isolation of mannoprotein biosynthesis mutants that are defective in genes which affect asparagine-linked glycosylation. Briefly, mutagenized *S. cerevisiae* cells were screened using fluoresceinated antibodies directed against the outer mannose chains present on wild-type yeast. Mutant cells that did not bind antibody were further characterized and were found to be defective in the addition of asparagine-linked oligosaccharide moieties. To optimize production of the heterologous proteins, it is preferred that the host strain carries a mutation, such as the *S. cerevisiae* pep4 mutation (Jones, *Genetics* 85: 23–33, 1977), which results in reduced proteolytic activity.

In addition to fungal cells, cultured mammalian cells may be used as host cells within the present invention. Preferred cell lines are rodent myeloma cell lines, which include p3X63Ag8 (ATCC TIB 9), FO (ATCC CRL 1646), NS-1 (ATCC TIB 18) and 210-RCY-Ag1 (Galfre et al., *Nature* 277: 131, 1979). A particularly preferred rodent myeloma cell line is SP2/0-Ag14 (ATCC CRL 1581). In addition, a number of other cell lines may be used within the present invention, including COS-1 (ATCC CRL 1650), BHK, p363.Ag.8.653 (ATCC CRL 1580) Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CC 29.1), 293 (ATCC CRL 1573; Graham et al., *J. Gen. Virol.* 36: 59–72, 1977) and DUKX cells (Urlaub and Chasin, *Proc. Natl. Acad. Sci USA* 77: 4216–4220, 1980) A preferred BHK cell line is the tk$^-$ts13 BHK cell line (Waechter and Baserga, *Proc. Natl. Acad. Sci USA* 79: 1106–1110, 1982). A preferred BHK cell line is the tk$^-$ts13 BHK cell line (Waechter and Baserga, *Proc. Natl. Acad. Sci. USA* 79: 1106–1110, 1982). A tk$^-$ BHK cell line is available from the American Type Culture Collection, Rockville, Md., under accession number CRL 1632. A particularly preferred tk$^-$ BHK cell line is BHK 570 which is available from the American Type Culture Collection under accession number 10314.

Mammalian expression vectors for use in carrying out the present invention will include a promoter capable of directing the transcription of a cloned gene or cDNA. Preferred promoters include viral promoters and cellular promoters. Preferred viral promoters include the major late promoter from adenovirus 2 (Kaufman and Sharp, *Mol. Cell. Biol.* 2: 1304–13199, 1982) and the SV40 promoter (Subramani et al., *Mol. Cell. Biol.* 1: 854–864, 1981). Preferred cellular promoters include the mouse metallothionein 1 promoter (Palmiter et al., *Science* 222: 809–814, 1983) and a mouse $V_K$ promoter (Grant et al., *Nuc. Acids Res.* 15: 5496, 1987). A particularly preferred promoter is a mouse $V_H$ promoter (Loh et al., ibid.). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., *Nuc. Acids Res.* 9: 3719–3730, 1981). A particularly preferred polyadenylation signal is the $V_H$ gene terminator (Loh et al., ibid.). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse $\mu$ enhancer (Gillies, *Cell* 33: 717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973.) Other techniques for introducing cloned DNA sequences into mammalian cells, such as electroporation (Neumann et al., *EMBO J.* 1: 841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene.

A particularly preferred amplifiable marker is the DHFR$^r$ cDNA (Simonsen and Levinson, *Proc. Natl. Adac. Sci. USA* 80: 2495–2499, 1983). Selectable markers are reviewed by Thilly (*Mammalian Cell Technology*, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Host cells containing DNA constructs of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient which are complemented by the selectable marker on the DNA construct or co-transfected with the DNA construct. Yeast cells, for example, are preferably grown in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 25 0.1M and 1.5M., preferably at 0.5M or 1.0M. Cultured mammalian cells are generally grown in commercially available serum-containing or serum-free media. Selection of a medium appropriate for the particular cell line used is within the level of ordinary skill in the art.

The culture medium from appropriately grown transformed or transfected host cells is separated from the cell material, and the presence of dimerized polypeptide fusions or secreted receptor analogs is demonstrated. A preferred method of detecting receptor analogs, for example, is by the binding of the receptors or portions of receptors to a receptor-specific antibody. An anti-receptor antibody may be a monoclonal or polyclonal antibody raised against the receptor in question, for example, an anti-PDGF receptor monoclonal antibody may be used to assay for the presence of PDGF receptor analogs. Another antibody, which may be used for detecting substance P-tagged peptides and proteins, is a commercially available rat anti-substance P monoclonal antibody which may be utilized to visualize peptides or proteins that are fused to the C-terminal amino acids of substance P. Ligand binding assays may also be used to detect the presence of receptor analogs. In the case of PDGF receptor analogs, it is preferable to use fetal foreskin fibroblasts, which express PDGF receptors, to compete against the PDGF receptor analogs of the present invention for labeled PDGF and PDGF isoforms.

Assays for detection of secreted, biologically active peptide dimers and receptor analogs may include Western transfer, protein blot or colony filter. A Western transfer filter may be prepared using the method described by Towbin et al. (*Proc. Natl. Acad. Sci. USA* 76: 4350–4354, 1979). Briefly, samples are electrophoresed in a sodium dodecyl-sulfate polyacrylamide gel. The proteins in the gel are electrophoretically transferred to nitrocellulose paper. Protein blot filters may be prepared by filtering supernatant samples or concentrates through nitrocellulose filters using, for example, a Minifold (Schleicher & Schuell, Keene, N.H.). Colony filters may be prepared by growing colonies on a nitrocellulose filter that has been laid across an appropriate growth medium. In this method, a solid medium is preferred. The cells are allowed to grow on the filters for at least 12 hours. The cells are removed from the filters by washing with an appropriate buffer that does not remove the proteins bound to the filters. A preferred buffer comprises 25 mM Tris-base, 19 mM glycine, pH 8.3, 20% methanol.

The dimerized polypeptide fusions and receptor analogs present on the Western transfer, protein blot or colony filters may be visualized by specific antibody binding using methods known in the art. For example, Towbin et al. (ibid.) describe the visualization of proteins immobilized on nitrocellulose filters with a specific antibody followed by a labeled second antibody, directed against the first antibody. Kits and reagents required for visualization are commercially available, for example, from Vector Laboratories, (Burlingame, Calif.), and Sigma Chemical Company (St. Louis, Mo.).

Secreted, biologically active dimerized polypeptide fusions and receptor analogs may be isolated from the medium of host cells grown under conditions that allow the secretion of the biologically active dimerized polypeptide fusions and receptor analogs. The cell material is removed from the culture medium, and the biologically active dimerized polypeptide fusions and receptor analogs are isolated using isolation techniques known in the art. Suitable isolation techniques include precipitation and fractionation by a variety of chromatographic methods, including gel filtration, ion exchange chromatography and immunoaffinity chromatography. A particularly preferred purification method is immunoaffinity chromatography using an antibody directed against the receptor analog or dimerized polypeptide fusion. The antibody is preferably immobilized or attached to a solid support or substrate. A particularly preferred substrate is CNBr-activated Sepharose (Pharmacia LKB Technologies, Inc., Piscataway, N.J.). By this method, the medium is combined with the antibody/substrate under conditions that will allow binding to occur. The complex may be washed to remove unbound material, and the receptor analog or peptide dimer is released or eluted through the use of conditions unfavorable to complex formation. Particularly useful methods of elution include changes in pH, wherein the immobilized antibody has a high affinity for the ligand at a first pH and a reduced affinity at a second (higher or lower) pH; changes in concentration of certain chaotropic agents; or through the use of detergents.

The secreted PDGF receptor analogs of the present invention can be used within a variety of assays for detecting the presence of and/or screening for native PDGF, PDGF isoforms or PDGF-like molecules. These assays will typically involve combining PDGF receptor analogs, which may be bound to a solid substrate such as polymeric microtiter plate wells, with a biological sample under conditions that permit the formation of receptor/ligand complexes. Screening assays for the detection of PDGF, PDGF isoforms or PDGF-like molecules will typically involve combining soluble PDGF receptor analogs with a biological sample and incubating the mixture with a PDGF isoform or mixture of PDGF isoforms bound to a solid substrate such as polymeric microtiter plates, under conditions that permit the formation of receptor/ligand complexes. Detection may be achieved through the use of a label attached to the receptor or through the use of a labeled antibody which is reactive with the receptor. Alternatively, the labeled antibody may be reactive with the ligand. A wide variety of labels may be utilized, such as radionuclides, fluorophores, enzymes and luminescers. Complexes may also be detected visually, i.e., in immunoprecipitation assays, which do not require the use of a label.

Secreted PDGF receptor analogs of the present invention may also be labeled with a radioisotope or other imaging agent and used for in vivo diagnostic purposes. Preferred radioisotope imaging agents include iodine-125 and technetium-99, with technetium-99 being particularly preferred. Methods for producing protein-isotope conjugates are well known in the art, and are described by, for example, Eckelman et al. (U.S. Pat. No. 4,652,440), Parker et al. (WO 87/05030) and Wilber et al. (EP 203,764). Alternatively, the secreted receptor analogs may be bound to spin label enhancers and used for magnetic resonance (MR) imaging. Suitable spin label enhancers include stable, sterically hindered, free radical compounds such as nitroxides. Methods for labeling ligands for MR imaging are disclosed by, for example, Coffman et al. (U.S. Pat. No. 4,656,026). For administration, the labeled receptor analogs are combined with a pharmaceutically acceptable carrier or diluent, such as sterile saline or sterile water. Administration is preferably by bolus injection, preferably intravenously. These imaging agents are particularly useful in identifying the locations of atherosclerotic plaques, PDGF-producing tumors, and receptor-bound PDGF.

The secreted PDGF receptor analogs of the present invention may also be utilized within diagnostic kits. Briefly, the subject receptor analogs are preferably provided in a lyophilized form or immobilized onto the walls of a suitable container, either alone or in conjunction with antibodies capable of binding to native PDGF or selected PDGF isoform(s) or specific ligands. The antibodies, which may be conjugated to a label or unconjugated, are generally included in the kits with suitable buffers, such as phosphate, stabilizers, inert proteins or the like. Generally, these materials are present in less than about 5% weight based upon the amount of active receptor analog, and are usually present in an amount of at least about 0.001% weight. It may also be desirable to include an inert excipient to dilute the active ingredients. Such an excipient may be present from about 1% to 99% weight of the total composition. In addition, the kits will typically include other standard reagents, instructions and, depending upon the nature of the label involved, reactants that are required to produce a detectable product. Where an antibody capable of binding to the receptor or receptor/ligand complex is employed, this antibody will usually be provided in a separate vial. The antibody is typically conjugated to a label and formulated in an analogous manner with the formulations briefly described above. The diagnostic kits, including the containers, may be produced and packaged using conventional kit manufacturing procedures.

As noted above, the secreted PDGF receptor analogs of the present invention may be utilized within methods for purifying PDGF from a variety of samples. Within a preferred method, the secreted PDGF receptor analogs are immobilized or attached to a substrate or support material, such as polymeric tubes, beads, polysaccharide particulates, polysaccharide-containing materials, polyacrylamide or other water insoluble polymeric materials. Methods for immobilization are well known in the art (Mosbach et al., U.S. Pat. No. 4,415,665; Clarke et al., *Meth. Enzymology* 68: 436–442, 1979). A common method of immobilization is CNBr activation. Activated substrates are commercially available from a number of suppliers, including Pharmacia (Piscataway, N.J.), Pierce Chemical Co. (Rockford, Ill.) and Bio-Rad Laboratories (Richmond, Calif.). A preferred substrate is CNBr-activated Sepharose (Pharmacia, Piscataway, N.J.). Generally, the substrate/receptor analog complex will be in the form of a column. The sample is then combined with the immobilized receptor analog under conditions that allow binding to occur. The substrate with immobilized receptor analog is first equilibrated with a buffer solution of a composition in which the receptor analog has been previously found to bind its ligand. The sample, in the solution used for equilibration, is then applied to the substrate/receptor analog complex. Where the complex is in the form of a column, it is preferred that the sample be passed over the column two or more times to permit full binding of ligand to receptor analog. The complex is then washed with the same solution to elute unbound material. In addition, a second wash solution may be used to minimize nonspecific binding. The bound material may then be released or eluted through the use of conditions unfavorable to complex formation. Particularly useful methods include changes in pH, wherein the immobilized receptor has a high affinity for PDGF at a first pH and reduced affinity at a second (higher or lower) pH; changes in concentration of certain chaotropic agents; or through the use of detergents.

The secreted PDGF receptor analogs fused to dimerizing proteins of the present invention may be used in pharmaceutical compositions for topical or intravenous application. The secreted PDGF receptor analogs of the present invention may be useful in the treatment of atherosclerosis by, for example, binding endogenous PDGF to prevent smooth muscle cell proliferation. The PDGF receptor analogs fused to dimerizing proteins are used in combination with a physiologically acceptable carrier or diluent. Preferred carriers and diluents include saline and sterile water. Pharmaceutical compositions may also contain stabilizers and adjuvants. The resulting aqueous solutions may be packaged for use or filtered under aseptic conditions and lyophilized, the lyophilized preparation being combined with a sterile aqueous solution prior to administration.

The following examples are offered by way of illustration and not by way of limitation.

EXAMPLES

Enzymes, including restriction enzymes, DNA polymerase I (Klenow fragment), T4 DNA polymerase, T4 DNA ligase and T4 polynucleotide kinase, were obtained from New England Biolabs (Beverly, Mass.), GIBCO-BRL (Gaithersburg, Md.) and Boerhinger-Mannheim Biochemicals (Indianapolis, Ind.) and were used as directed by the manufacturer or as described in Maniatis et al. (*Molecular Cloning: A Laboratory Manual*, Cold Spring Harbor Laboratory, N.Y., 1982) and Sambrook et al. (*Molecular Cloning: A Laboratory Manual*/Second Edition, Cold Spring Harbor Laboratory, N.Y., 1989).

EXAMPLE 1

Cloning PDGF Receptor cDNAs

A. Cloning the PDGF β-Receptor

A cDNA encoding the PDGF β-receptor was cloned as follows. Complementary DNA (cDNA) libraries were prepared from poly(A) RNA from diploid human dermal fibroblast cells, prepared by explant from a normal adult, essentially as described by Hagen et al. (*Proc. Natl. Acad. Sci. USA* 83: 2412–2416, 1986). Briefly, the poly(A) RNA was primed with oligo d(T) and cloned into λgt11 using Eco RI linkers. The random primed library was screened for the presence of human PDGF receptor cDNA's using three oligonucleotide probes complementary to sequences of the mouse PDGF receptor (Yarden et al., *Nature* 323: 226–232, 1986). Approximately one million phage from the random primed human fibroblast cell library were screened using oligonucleotides ZC904, ZC905 and ZC906 (Table 1; Sequence ID Numbers 5, 6 and 7, respectively). Eight positive clones were identified and plaque purified. Two clones, designated RP41 and RP51, were selected for further analysis by restriction enzyme mapping and DNA sequence analysis. RP51 was found to contain 356 bp of 5'-noncoding sequence, the ATG translation initiation codon and 738 bp of the amino terminal coding sequence. RP41 was found to overlap clone RP51 and contained 2649 bp encoding amino acids 43–925 of the β-receptor protein.

TABLE 1

Oligonucleotide Sequences

ZC871 (Sequence ID Number 3)

5' CTC TCT TCC TCA GGT AAA TGA GTG CCA GGG CCG GCA AGC CCC CGC TCC 3'

ZC872 (Sequence ID Number 4)

5' CCG GGG AGC GGG GGC TTG CCG GCC CTG GCA CTC ATT TAC CTG AGG AAG AGA GAG CT 3'

ZC904 (Sequence ID Number 5)

5' CAT GGG CAC GTA ATC TAT AGA TTC ATC CTT GCT CAT ATC CAT GTA 3'

ZC905 (Sequence ID Number 6)

5' TCT TGC CAG GGC ACC TGG GAC ATC TGT TCC CAC ATC ACC GG 3'

ZC906 (Sequence ID Number 7)

5' AAG CTG TCC TCT GCT TCA GCC AGA GGT CCT GGG CAG CC 3'

ZC1380 (Sequence ID Number 8)

5' CAT GGT GGA ATT CCT GCT GAT 3'

ZC1447 (Sequence ID Number 9)

5' TG GTT GTG CAG AGC TGA GGA AGA GAT GGA 3'

ZC1453 (Sequence ID Number 10)

5' AAT TCA TTA TGT TGT TGC AAG CCT TCT TGT TCC TGC TAG CTG GTT TCG CTG TTA A 3'

ZC1454 (Sequence ID Number 11)

5' GAT CTT AAC AGC GAA ACC AGC TAG CAG GAA CAA GAA GGC TTG CAA CAA CAT AAT G 3'

ZC1478 (Sequence ID Number 12)

5' ATC GCG AGC ATG CAG ATC TGA 3'

ZC1479 (Sequence ID Number 13)

TABLE 1-continued

5' AGC TTC AGA TCT GCA TGC TGC CGA T 3'

ZC1776 (Sequence ID Number 14)

5' AGC TGA GCG CAA ATG TTG TGT CGA GTG CCC ACC GTG CCC AGC TTA GAA TTC T 3'

ZC1777 (Sequence ID Number 15)

5' CTA GAG AAT TCT AAG CTG GGC ACG GTG GGC ACT CGA CAC AAC ATT TGC GCT C 3'

ZC1846 (Sequence ID Number 16)

5' GAT CGG CCA CTG TCG GTG CGC TGC ACG CTG CGC AAC GCT GTG GGC CAG GAC ACG CAG GAG GTC ATC GTG GTG CCA CAC TCC TTG CCC TTT AAG CA 3'

ZC1847 (Sequence ID Number 17)

5' AGC TTG CTT AAA GGG CAA GGA GTG TGG CAC CAC GAT GAC CTC CTG CGT GTC CTG GCC CAC AGC GTT GCG CAG CGT GCA GCG CAC CGA CAG TGG CC 3'

ZC1886 (Sequence ID Number 18)

5' CCA GTG CCA AGC TTG TCT AGA CTT ACC TTT AAA GGG CAA GGA G 3'

ZC1892 (Sequence ID Number 19)

5' AGC TTG AGC GT 3'

ZC1893 (Sequence ID Number 20)

5' CTA GAC GCT CA 3'

ZC1894 (Sequence ID Number 21)

5' AGC TTC CAG TTC TTC GGC CTC ATG TCA GTT CTT CGG CCT CAT GTG AT 3'

ZC1895 (Sequence ID Number 22)

5' CTA GAT CAC ATG AGG CCG AAG AAC TGA CAT GAG GCC GAA GAA CTG GA 3'

ZC2181 (Sequence ID Number 23)

5' AAT TCG GAT CCA CCA TGG GCA CCA GCC ACC GG CGT TCC TGG TGT TAG GCT GCC TGC TGA CCG GCC 3'

ZC2182 (Sequence ID Number 24)

5' TGA GCC TGA TCC TGT GCC AAC TGA GCC TGC CAT CGA TCC TGC CAA ACG AGA ACG AGA AGG TTG TGC AGC TA 3'

ZC2183 (Sequence ID Number 25)

5' AAT TTA GCT GCA CAA CCT TCT CGT TCT CGT TTG GCA GGA TCG ATG GCA GGC TCA GTT GGC ACA GGA TCA 3'

ZC2184 (Sequence ID Number 26)

5' GGC TCA GGC CGG TCA GCA GGC AGC CTA ACA CCA GGA ACG CCG GGT GGC TGG TGC CCA TGG TGG ATC CG 3'

ZC2311 (Sequence ID Number 27)

5' TGA TCA CCA TGG CTC AAC TG 3'

ZC2351 (Sequence ID Number 28)

5' CGA ATT CCA C 3'

TABLE 1-continued

ZC2352 (Sequence ID Number 29)

5' CAT GGT GGA ATT CGA GCT 3'

ZC2392 (Sequence ID Number 30)

5' ACG TAA GCT TGT CTA GAC TTA CCT TCA GAA CGC AGG GTG GG 3'

The 3'-end of the cDNA was not isolated in the first cloning and was subsequently isolated by screening $6 \times 10^5$ phage of the oligo d(T)-primed cDNA library with a 630 bp Sst I-Eco RI fragment derived from the 3'-end of clone RP41. One isolate, designated OT91, was further analyzed by restriction enzyme mapping and DNA sequencing. This clone was found to comprise the 3'-end of the receptor coding region and 1986 bp of 3' untranslated sequence.

Clones RP51, RP41 and OT91 were ligated together to construct a full-length cDNA encoding the entire PDGF β-receptor. RP41 was digested with Acc I and Bam HI to isolate the 2.12 kb fragment. RP51 was digested with Eco RI and Acc I to isolate the 982 bp fragment. The 2.12 kb RP41 fragment and the 982 bp RP51 fragment were joined in a three-part ligation with pUC13, which had been linearized by digestion with Eco RI and Bam HI. The resultant plasmid was designated 51/41. Plasmid 51/41 was digested with Eco RI and Bam HI to isolate the 3 kb fragment comprising the partial PDGF receptor cDNA. OT91 was digested with Bam HI and Xba I to isolate the 1.4 kb fragment containing the 3' portion of the PDGF receptor cDNA. The Eco RI-Bam HI 51/41 fragment, the Bam HI-Xba I OT91 fragment and the Eco RI-Xba I digested pUC13 were joined in a three-part ligation. The resultant plasmid was designated pR-RX1 (FIG. 2).

B. Cloning the PDGF-α Receptor

A cDNA encoding to PDGF α-receptor was cloned as follows. RNA was prepared by the method of Chirgwin et al. (Biochemistry 18: 5294, 1979) and twice purified on oligo d(T) cellulose to yield poly(A)+RNA. Complementary DNA was prepared in λgt10 phage using a kit purchased from Invitrogen (San Diego, Calif.). The resulting λ phage DNA was packaged with a coat particle mixture from Stratagene Cloning Systems (La Jolla, Calif.), infected into E. coli strain C600 Hfl⁻ and titered.

Approximately $1.4 \times 10^6$ phage recombinants were plated to produce plaques for screening. Nitrocellulose filter lifts were prepared according to standard methods and were hybridized to a radiolabeled PDGF β-receptor DNA fragment (Gronwald et al., ibid.) comprising the 1.9 kb Fsp I-Hind III fragment that encodes the transmembrane and cytoplasmic domains of the PDGF β-receptor cDNA. Hybridization was performed for 36 hours at 42° C. in a mixture containing 40% formamide, 5×SSCP (SSC containing 25 mM phosphate buffer, pH 6.5), 200 µg/ml denatured salmon sperm DNA, 3×Denhardt's, and 10% dextran sulfate. Following hybridization, the filters were washed extensively at room temperature in 2×SSC, then for 15 minutes at 47°–48° C. Following an exposure to X-ray film, the filters were treated to increasingly stringent wash conditions followed by film recording until a final wash with 0.1×SSC at 65° C. was reached. Film analysis showed that a "family" of plaques that hybridized at lower wash stringency but not at the highest stringency. This "family" was selected for further analysis.

Two λ phage clones from the "family" obtained from the initial screening were subcloned into the Not I site of the pUCtype plasmid vector pBluescript SK⁺ (obtained from Stratagene Cloning Systems, La Jolla, Calif.) and were analyzed by restriction mapping and sequence analysis. Restriction enzyme analysis of a phage clone, designated α1-1, revealed a restriction fragment pattern dissimilar from that of the PDGF β-receptor cDNA with the exception of a common Bgl II-Bgl II band of approximately 160 bp. The PDGF β-receptor cDNA contains two similarly spaced Bgl II sites within the region coding for the second tyrosine kinase domain.

Restriction analysis of a second plasmid subclone (designated α1-7) revealed an overlap of the 5' approximately 1.2 kb of clone α1-1, and an additional approximately 2.2 kb of sequence extending in the 5' direction. Sequence analysis revealed that the 3' end of this clone encodes the second tyrosine kinase domain, which contains regions of near sequence identity to the corresponding regions in the PDGF β-receptor. The 5' end of clone α1-7 contained non-receptor sequences. Two additional α-receptor clones were obtained by probing with α1-1 sequences. Clone α1-1 was digested with Not I and Spe I, and a 230 bp fragment was recovered. Clone α1-1 was also digested with Bam HI and Not I, and a 550 bp fragment was recovered. A clone that hybridized to the 230 bp probe was designated α5-1. This clone contained the 5'-most coding sequence for the PDGF α-receptor. Another clone, designated α6-3, hybridized to the 550 bp probe and was found to contain 3' coding and non-coding sequences, including the poly(A) tail.

Clone α1-1 was radiolabeled ($^{32}$P) and used to probe a northern blot (Thomas, Methods Enzymol. 100: 225–265, 1983) of the MG-63 poly(A)+RNA used to prepare the cDNA library. A single band of approximately 6.6 kb was observed. RNA prepared from receptor-positive cell lines including the human fibroblast SK4, WI-38 and 7573 cell lines; the mouse fibroblast line DI 3T3; the U2-OS human osteosarcoma cell line and baboon aortic smooth muscle cells, and RNA prepared from receptor-negative lines including A431 (an epithelial cell line) and VA 13 (SV40-transformed WI-38 cells) were probed by northern format with the α1-1 cDNA. In all cases, the amount of the 6.6 kb band detected in these RNA correlated well with the relative levels of α-receptor detected on the respective cell surfaces. The 6.6 kb RNA was not detected in RNA prepared from any tested cell line of hematopoietic origin, in agreement with a lack of PDGF α-receptor protein detected on these cell types.

Figure 12:
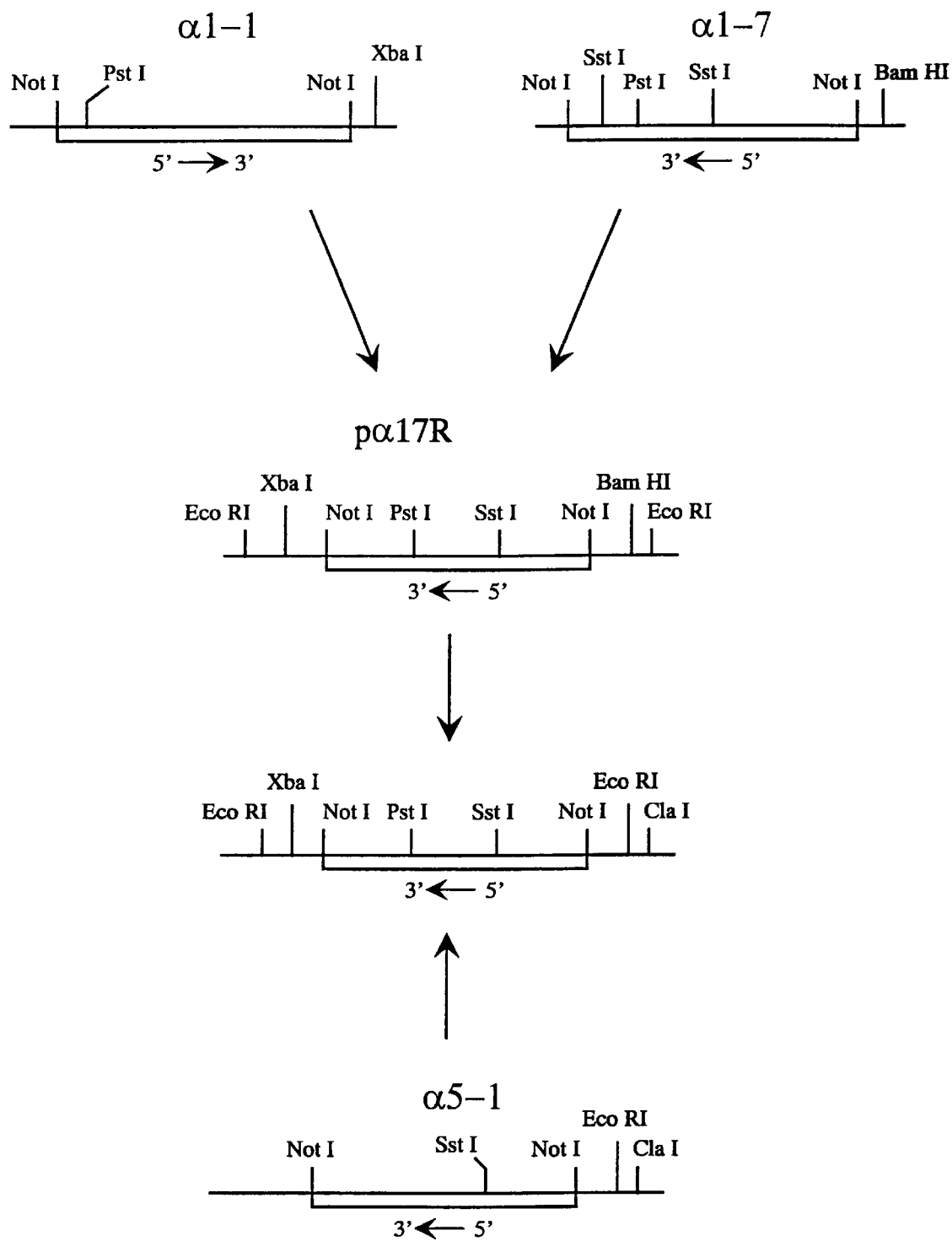
FIG. 12 illustrates the assembly of a cDNA molecule encoding a PDGF $\alpha$-receptor. Complementary DNA sequences are shown as lines. Only those portions of the vectors adjacent to the cDNA inserts are shown.

Clones α1-1 and α1-7 were joined at a unique Pst I site in the region encoding the transmembrane portion of the receptor. Clone α1-1 was digested with Xba I and Pst I and the receptor sequence fragment was recovered. Clone α1-7 was digested with Pst I and Bam HI and the receptor fragment was recovered. The two fragments were ligated with Xba I+Bam HI-digested pIC19R (Marsh et al. *Gene* 32: 481–486, 1984) to construct plasmid pα17R (FIG. 12).

The remainder of the 5'-most α-receptor sequence was obtained from clone α5-1 as an Sst I-Cla I fragment. This fragment was joined to the Eco RI-Sst I receptor fragment of pα17R and cloned into Eco RI+Cla I-digested pBluescript SK+plasmid to construct plasmid pα17B (FIG. 12). FIGS. 11A–D (Sequence ID Numbers 35 and 36) shows the nucleotide sequence and deduced amino acid sequence of the cDNA present in pα17B.

EXAMPLE 2

Construction of a SUC2 Signal Sequence-PDGF β-Receptor Fusion

To direct the PDGF β-receptor into the yeast secretory pathway, the PDGF β-receptor cDNA was joined to a sequence encoding the *Saccharomyces cerevisiae* SUC2 signal sequence. Oligonucleotides ZC1453 and ZC1454 (Sequence ID Numbers 10 and 11; Table 1) were designed to form an adapter encoding the SUC2 secretory signal flanked by a 5' Eco RI adhesive end and a 3' Bgl II adhesive end. ZC1453 and ZC1454 were annealed under conditions described by Maniatis et al. (ibid.). Plasmid pR-RX1 was digested with Bgl II and Sst II to isolate the 1.7 kb fragment comprising the PDGF β-receptor coding sequence from amino acids 28 to 596. Plasmid pR-RX1 was also cut with Sst II and Hind III to isolate the 1.7 kb fragment comprising the coding sequence from amino acids 597 through the translation termination codon and 124 bp of 3' untranslated DNA. The two 1.7 kb pR-RX1 fragments and the ZC1453/ ZC1454 adapter were joined with pUC19, which had been linearized by digestion with Eco RI and Hind III. The resultant plasmid, comprising the SUC2 signal sequence fused in-frame with the PDGF β-receptor cDNA, was designated pBTL10 (FIG. 2).

EXAMPLE 3

Construction of pCBS22

The BAR1 gene product, Barrier, is an exported protein that has been shown to have three domains. When used in conjunction with a first signal sequence, the third domain of Barrier protein has been shown to aid in the secretion of proteins into the medium (MacKay et al., U.S. patent application Ser. No. 104,316).

Figure 3:
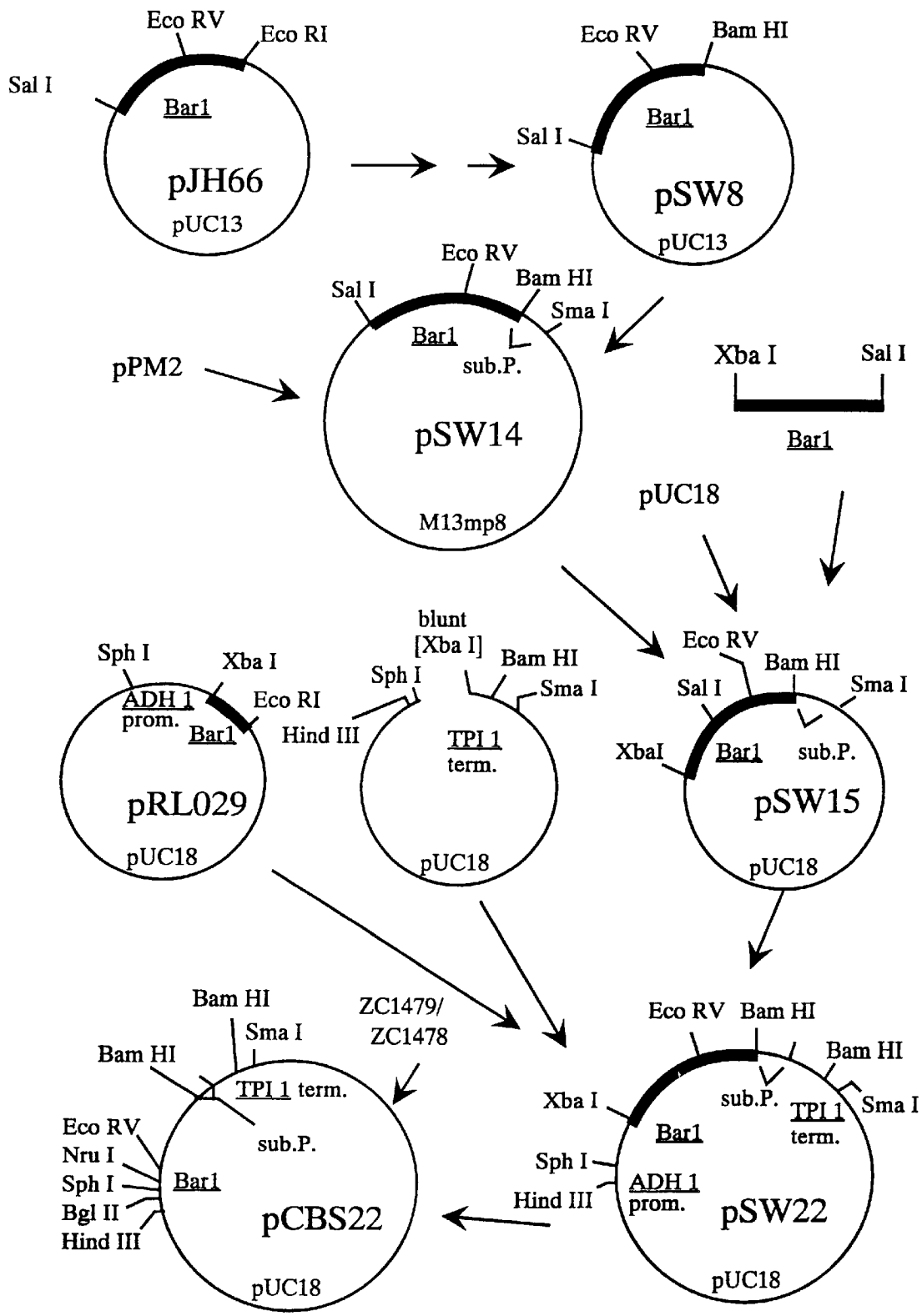
FIG. 3 illustrates the construction of pCBS22.

The portion of the BAR1 gene encoding the third domain of Barrier was joined to a sequence encoding the C-terminal portion of substance P (subp; Munro and Pelham, *EMBO J.* 3: 3087–3093, 1984). The presence of the substance P amino acids on the terminus of the fusion protein allowed the protein to be detected using commercially available anti-substance P antibodies. Plasmid pZV9 (deposited as a transformant in *E. coli* strain RR1, ATCC accession no. 53283), comprising the entire BAR1 coding region and its associated flanking regions, was cut with Sal I and Bam HI to isolate the 1.3 kb BAR1 fragment. This fragment was subcloned into pUC13, which had been cut with Sal I and Bam HI, to generate the plasmid designated pZV17. Plasmid pZV17 was digested with Eco RI to remove the 3'-most 0.5 kb of the BAR1 coding region. The vector-BAR1 fragment was religated to create the plasmid designated pJH66 (FIG. 3). Plasmid pJH66 was linearized with Eco RI and blunt-ended with DNA polymerase I (Klenow fragment). Kinased Bam HI linkers (5' CCG GAT CCG G 3') were added and excess linkers were removed by digestion with Bam HI before religation. The resultant plasmid was designated pSW8 (FIG. 3).

Plasmid pSW81, comprising the TPI1 promoter, the BAR1 coding region fused to the coding region of the C-terminal portion of substance P (Munro and Pelham, *EMBO J.* 3: 3087–3093, 1984) and the TPI1 terminator, was derived from pSW8. Plasmid pSW8 was cut with Sal I and Bam HI to isolate the 824 bp fragment encoding amino acids 252 through 526 of BAR1. Plasmid pPM2, containing the synthetic oligonucleotide sequence encoding the dimer form of the C-terminal portion of substance P (subP) in M13mp8, was obtained from Hugh Pelham (MRC Laboratory of Molecular Biology, Cambridge, England). Plasmid pPM2 was linearized by digestion with Bam HI and Sal I and ligated with the 824 bp BAR1 fragment from pSW8. The resultant plasmid, pSW14, was digested with Sal I and Sma I to isolate the 871 bp BAR1-substance P fragment. Plasmid pSW16, comprising a fragment of BAR1 encoding amino acids 1 through 250, was cut with Xba I and Sal I to isolate the 767 bp BAR1 fragment. This fragment was ligated with the 871 bp BAR1-substance P fragment in a three-part ligation with pUC18 cut with Xba I and Sma I. The resultant plasmid, designated pSW15, was digested with Xba I and Sma I to isolate the 1.64 kb BAR1-substance P fragment. The ADH1 promoter was obtained from pRL029. Plasmid pRL029, comprising the ADH1 promoter and the BAR1 5' region encoding amino acids 1 to 33 in pUC18, was digested with Sph I and Xba I to isolate the 0.42 kb ADH1 promoter fragment. The TPI1 terminator (Alber and Kawasaki, ibid.) was provided as a linearized fragment containing the TPI1 terminator and pUC18 with a Klenow-filled Xba I end and an Sph I end. This fragment was ligated with the 0.42 kb ADH1 promoter fragment and the 1.64 kb BAR1-substance P fragment in a three-part ligation to produce plasmid pSW22.

The ADH1 promoter and the coding region of BAR1, from the translation initiation ATG through the Eco RV site present in pSW22, were removed by digestion with Hind III and Eco RV. The 3.9 kb vector fragment, comprising the 401 bp between the Eco RV and the Eco RI sites of the BAR1 gene fused to subP and the TPI1 terminator, was isolated by gel electrophoresis. Oligonucleotide ZC1478 (Sequence ID Number 12; Table 1) was kinased and annealed with oligonucleotide ZC1479 (Sequence ID Number 13; Table 1) using conditions described by Maniatis et al. (ibid.). The annealed oligonucleotides formed an adapter comprising a Hind III adhesive end and a polylinker encoding Bgl II, Sph I, Nru I and Eco RV restriction sites. The ZC1479/ZC1478 adapter was ligated with the gel-purified pSW22 fragment. The resultant plasmid was designated pCBS22 (FIG. 3).

EXAMPLE 4

Construction of pBTL13

Figure 4:
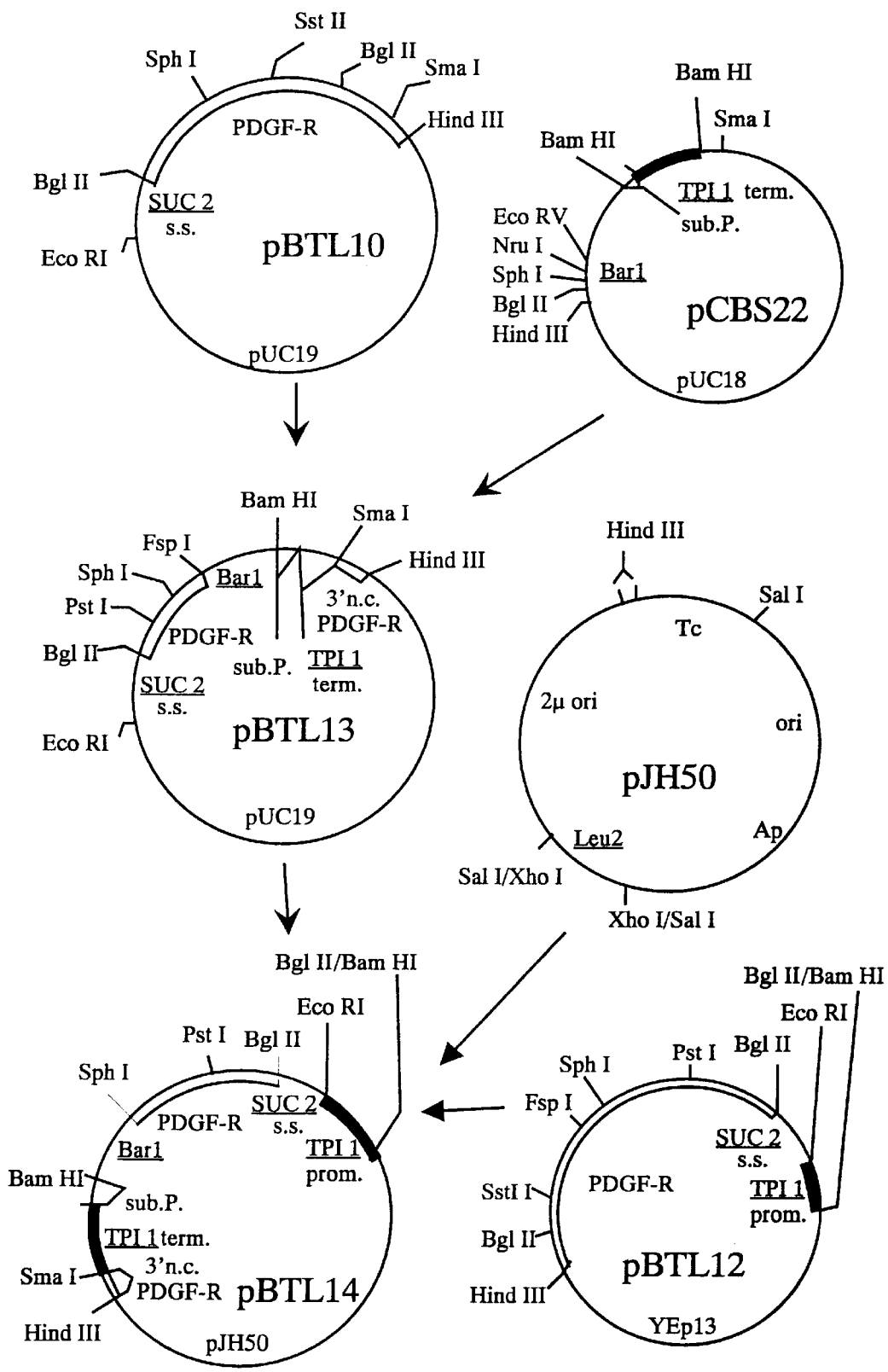
FIG. 4 illustrates the construction of pBTL13 and pBTL14.

In order to enhance the secretion of the PDGF β-receptor and to facilitate the identification of the secreted protein, a sequence encoding the third domain of BAR1 fused to the C-terminal amino acids of substance P was fused in frame with the 5' 1240 bp of the PDGF β-receptor. Plasmid pBTL10 (Example 2) was digested with Sph I and Sst I to isolate the 4 kb fragment comprising the SUC2 signal sequence, a portion of the PDGF β-receptor cDNA and the pUC19 vector sequences. Plasmid pCBS22 was digested with Sph I and Sst I to isolate the 1.2 kb fragment comprising the BAR1-subP fusion and the TPI1 terminator. These two fragments were ligated, and the resultant plasmid was designated pBTL13 (FIG. 4).

EXAMPLE 5

Construction of an Expression Vector Encoding the Entire PDGF β-Receptor

The entire PDGF β-receptor was directed into the secretory pathway by fusing a SUC2 signal sequence to the 5' end of the PDGF β-receptor coding sequence. This fusion was placed behind the TPI1 promoter and inserted into the vector YEp13 for expression in yeast.

The TPI1 promoter was obtained from plasmid pTPIC10 (Alber and Kawasaki, *J. Mol. Appl. Genet.* 1: 410–434, 1982), and plasmid pFATPOT (Kawasaki and Bell, EP 171,142; ATCC 20699). Plasmid pTPIC10 was cut at the unique Kpn I site, the TPI1 coding region was removed with Bal-31 exonuclease, and an Eco RI linker (sequence: GGA ATT CC) was added to the 3' end of the promoter. Digestion with Bgl II and Eco RI yielded a TPI1 promoter fragment having Bgl II and Eco RI sticky ends. This fragment was then joined to plasmid YRp7' (Stinchcomb et al., *Nature* 282: 39–43, 1979) that had been cut with Bgl II and Eco RI (partial). The resulting plasmid, TE32, was cleaved with Eco RI (partial) and Bam HI to remove a portion of the tetracycline resistance gene. The linearized plasmid was then recircularized by the addition of an Eco RI-Bam HI linker to produce plasmid TEA32. Plasmid TEA32 was digested with Bgl II and Eco RI, and the 900 bp partial TPI1 promoter fragment was gel-purified. Plasmid pIC19H (Marsh et al., *Gene* 32:481–486, 1984) was cut with Bgl II and Eco RI and the vector fragment was gel purified. The TPI1 promoter fragment was then ligated to the linearized pIC19H and the mixture was used to transform *E. coli* RR1. Plasmid DNA was prepared and screened for the presence of a -900 bp Bgl II-Eco RI fragment. A correct plasmid was selected and designated pICTPIP.

The TPI1 promoter was then subcloned to place convenient restriction sites at its ends. Plasmid pIC7 (Marsh et al., ibid.) was digested with Eco RI, the fragment ends were blunted with DNA polymerase I (Klenow fragment), and the linear DNA was recircularized using T4 DNA ligase. The resulting plasmid was used to transform *E. coli* RR1. Plasmid DNA was prepared from the transformants and was screened for the loss of the Eco RI site. A plasmid having the correct restriction pattern was designated pIC7RI*. Plasmid pIC7RI* was digested with Hind III and Nar I, and the 2500 bp fragment was gel-purified. The partial TPI1 promoter fragment (ca. 900 bp) was removed from pICTPIP using Nar I and Sph I and was gel-purified. The remainder of the TPI1 promoter was obtained from plasmid pFATPOT by digesting the plasmid with Sph I and Hind III, and a 1750 bp fragment, which included a portion of the TPI1 promoter fragment from pICTPIP, and the fragment from PFATPOT were then combined in a triple ligation to produce pMVR1 (FIG. 2).

The TPI1 promoter was then joined to the SUC2-PDGF β-receptor fusion. Plasmid pBTL10 (Example 2) was digested with Eco RI and Hind III to isolate the 3.4 kb fragment comprising the SUC2 signal sequence and the entire PDGF β-receptor coding region. Plasmid pMVR1 was digested with Bgl II and Eco RI to isolate the 0.9 kb TPI1 promoter fragment. The TPI1 promoter fragment and the fragment derived from pBTL10 were joined with YEp13, which had been linearized by digestion with Bam HI and Hind III, in a three-part ligation. The resultant plasmid was designated pBTL12 (FIG. 2).

EXAMPLE 6

Construction of an Expression Vector Encoding the 5' Extracellular Portion of the PDGF β-Receptor The extracellular portion of the PDGF β-receptor was directed into the secretory pathway by fusing the coding sequence to the SUC2 signal sequence. This fusion was placed in an expression vector behind the TPI1 promoter.

Plasmid pBTL10 (Example 2) was digested with Eco RI and Sph I to isolate the approximately 1.3 kb fragment comprising the SUC2 signal sequence and the PDGF β-receptor extracellular domain coding sequence. Plasmid pMVR1 (Example 5) was digested with Bgl II and Eco RI to isolate the 0.9 kb TPI1 promoter fragment. The TPI1 promoter fragment was joined with the fragment derived from pBTL10 and YEp13, which had been linearized by digestion with Bam HI and Sph I, in a three-part ligation. The resultant plasmid was designated pBTL11 (FIG. 2).

EXAMPLE 7

Construction of Yeast Expression Vectors pBTL14 and pBTL15, and The Expression of PDGF β-Receptor-BAR1-subP Fusions A. Construction of pBTL14

The SUC2-PDGFβ-R fusion was joined with the third domain of BAR1 to enhance the secretion of the receptor, and the expression unit was cloned into a derivative of YEp13 termed pJH50. YEp13 was modified to destroy the Sal I site near the LEU2 gene. This was achieved by partially digesting YEp13 with Sal I followed by a complete digestion with Xho I. The 2.0 kb Xho I-Sal I fragment comprising the LEU2 gene and the 8.0 kb linear YEp13 vector fragment were isolated and ligated together. The ligation mixture was transformed into *E. coli* strain RR1. DNA was prepared from the transformants and was analyzed by digestion with Sal I and Xho I. A clone was isolated which showed a single Sal I site and an inactive Xho I site indicating that the LEU2 fragment had inserted in the opposite orientation relative to the parent plasmid YEp13. The plasmid was designated pJH50.

Referring to FIG. 4, plasmid pBTL12 (Example 5) was digested with Sal I and Pst I to isolate the 2.15 kb fragment comprising 270 bp of YEp13 vector sequence, the TPI1 promoter, the SUC2 signal sequence, and 927 bp of PDGF β-receptor cDNA. Plasmid pBTL13 (Example 4) was digested with Pst I and Hind III to isolate the 1.48 kb fragment comprising 313 bp of PDGF β-receptor cDNA, the BAR1-subP fusion and the TPI1 terminator. The fragments derived from pBTL12 and pBTL13 were joined with pJH50, which had been linearized by digestion with Hind III and Sal I, in a three-part ligation. The resultant plasmid was designated pBTL14.

B. Construction of pBTL15

Figure 5:
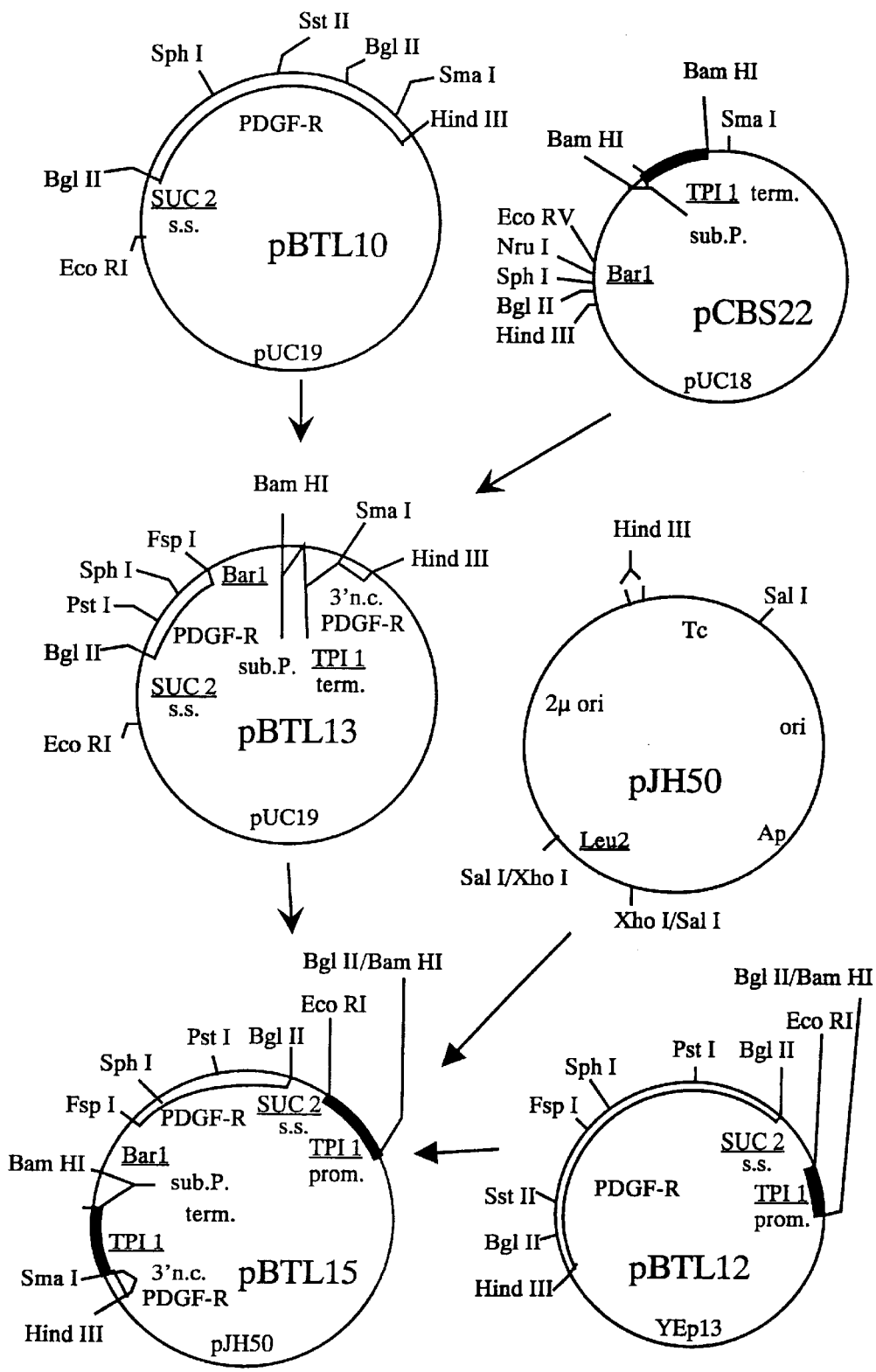
FIG. 5 illustrates the construction of pBTL15.

Referring to FIG. 5, a yeast expression vector was constructed comprising the TPI1 promoter, the SUC2 signal sequence, 1.45 kb of PDGF β-receptor cDNA sequence fused to the BAR1-subP fusion and the TPI1 terminator. Plasmid pBTL12 (Example 5) was digested with Sal I and Fsp I to isolate the 2.7 kb fragment comprising the TPI1 promoter, the SUC2 signal sequence, the PDGFβ-R coding sequence, and 270 bp of YEp13 vector sequence. Plasmid pBTL13 (Example 4) was digested with Nru I and Hind III to isolate the 1.4 kb fragment comprising the BAR1-subP fusion, the TPI1 terminator and 209 bp of 3' PDGF β-receptor cDNA sequence. The fragments derived from pBTL12 and pBTL13 were joined in a three-part ligation with pJH50, which had been linearized by digestion with Hind III and Sal I. The resultant plasmid was designated pBTL15.

C. Expression of PDGFβ-R-subP fusions from pBTL14 and pBTL15

Yeast expression vectors pBTL14 and pBTL15 were transformed into *Saccharomyces cerevisiae* strains ZY100 (MATa leu2-3,112 ade2-101 suc2-Δ9 gal2 pep4::TPI1prom-CAT) and ZY400 (MATa leu2-3,112 ade2-101 suc2-Δ9 gal2 pep4::TPI1prom-CAT Δmnn9::URA3). Transformations were carried out using the method essentially described by Beggs (ibid.). Transformants were selected for their ability to grow on -LEUDS (Table 2).

TABLE 2

Media Recipes

-LeuThrTrp Amino Acid Mixture
4 g adenine
3 g L-arginine
5 g L-aspartic acid
2 g L-histidine free base
6 g L-isoleucine
4 g L-lysine-mono hydrochloride
2 g L-methionine
6 g L-phenylalanine
5 g L-serine
5 g L-tyrosine
4 g uracil
6 g L-valine
Mix all the ingredients and grind with a mortar and pestle until the mixture is finely ground.
-LEUDS
20 g glucose
6.7 g Yeast Nitrogen Base without amino acids (DIFCO Laboratories Detroit, Mich.)
0.6 g -LeuThrTrp Amino Acid Mixture
182.2 g sorbitol
18 g Agar
Mix all the ingredients in distilled water. Add distilled water to a final volume of 1 liter. Autoclave 15 minutes. After autoclaving add 150 mg L-threonine and 40 mg L-tryptophan. Pour plates and allow to solidify.
-LEUDS+sodium succinate, pH 6.5
20 g Yeast Nitrogen Base without amino acids
0.6 g -LeuTrpThr Amino Acid Mixture
182.2 g sorbitol
11.8 g succinic acid
Mix all ingredients in distilled water to a final volume of 1 liter. Adjust the pH of the solution to pH 6.5. Autoclave 15 minutes. After autoclaving add 150 mg L-threonine and 40 mg L-tryptophan.
Fermentation Medium
7 g/l yeast nitrogen base without amino acids or ammonium sulfate (DIFCO Laboratories)
0.6 g/l ammonium sulfate
0.5M sorbitol
0.39 g/l adenine sulfate
0.01% polypropylene glycol
Mix all ingredients in distilled water. Autoclave 15 minutes. Add 80 ml 50% glucose for each liter of medium.
Super Synthetic -LEUD. pH 6.5 (liquid or solid medium)
6.7 g Yeast Nitrogen Base without amino acids or ammonium sulfate (DIFCO)
6 g ammonium sulfate
160 g adenine
0.6 g -LeuThrTrp Amino Acid Mixture
20 g glucose
11.8g succinic acid
Mix all ingredients and add distilled water to a final volume of 800 ml. Adjust the pH of the solution to pH 6.4. Autoclave 15 minutes. For solid medium, add 18 g agar before autoclaving, autoclave and pour plates.
Super Synthetic-LEUDS, pH 6.4 (liquid or solid medium)
Use the same recipe as Super Synthetic -LEUD, pH 6.4, but add 182.2 g sorbitol before autoclaving.

YEPD
20 g glucose
20 g Bacto Peptone (DIFCO Laboratories)
10 g Bacto Yeast Extract (DIFCO Laboratories)
18 g agar
4 ml adenine 1%
8 ml 1% L-leucine
Mix all ingredients in distilled water, and bring to a final volume of 1 liter. Autoclave 25 minutes and pour plates.

The transformants were assayed for binding to an anti-PDGF β-receptor monoclonal antibody (PR7212) or an anti-substance P antibody by protein blot assay. ZY100 [pBTL14] and ZY100[pBTL15] transformants were grown overnight at 30° 0C. in 5 ml Super Synthetic -LEUD, pH 6.4 (Table 2). ZY400[pBTL14] and ZY400[pBTL15] transformants were grown overnight at 30° C. in 5 ml Super Synthetic-LEUDS, pH 6.4 (Table 2). The cultures were pelleted by centrifugation and the supernatants were assayed for the presence of secreted PDGF β-receptor anlogs by protein blot assay using methods described in Example 18. Results of assays using PR7212 are shown in Table 3.

TABLE 3

Results of a protein blot probed with PR7212

Transformant:

| | |
|---|---|
| ZY100[pBTL14] | + |
| ZY400[pBTL14] | ++ |
| ZY100[pBTL15] | + |
| ZY400[pBTL15] | + |

EXAMPLE 8

Construction of a SUC2-PDGFβ-R Fusion Comprising the Complete PDGFβ-R Extracellular Domain A. Construction of pBTL22

Figure 6:
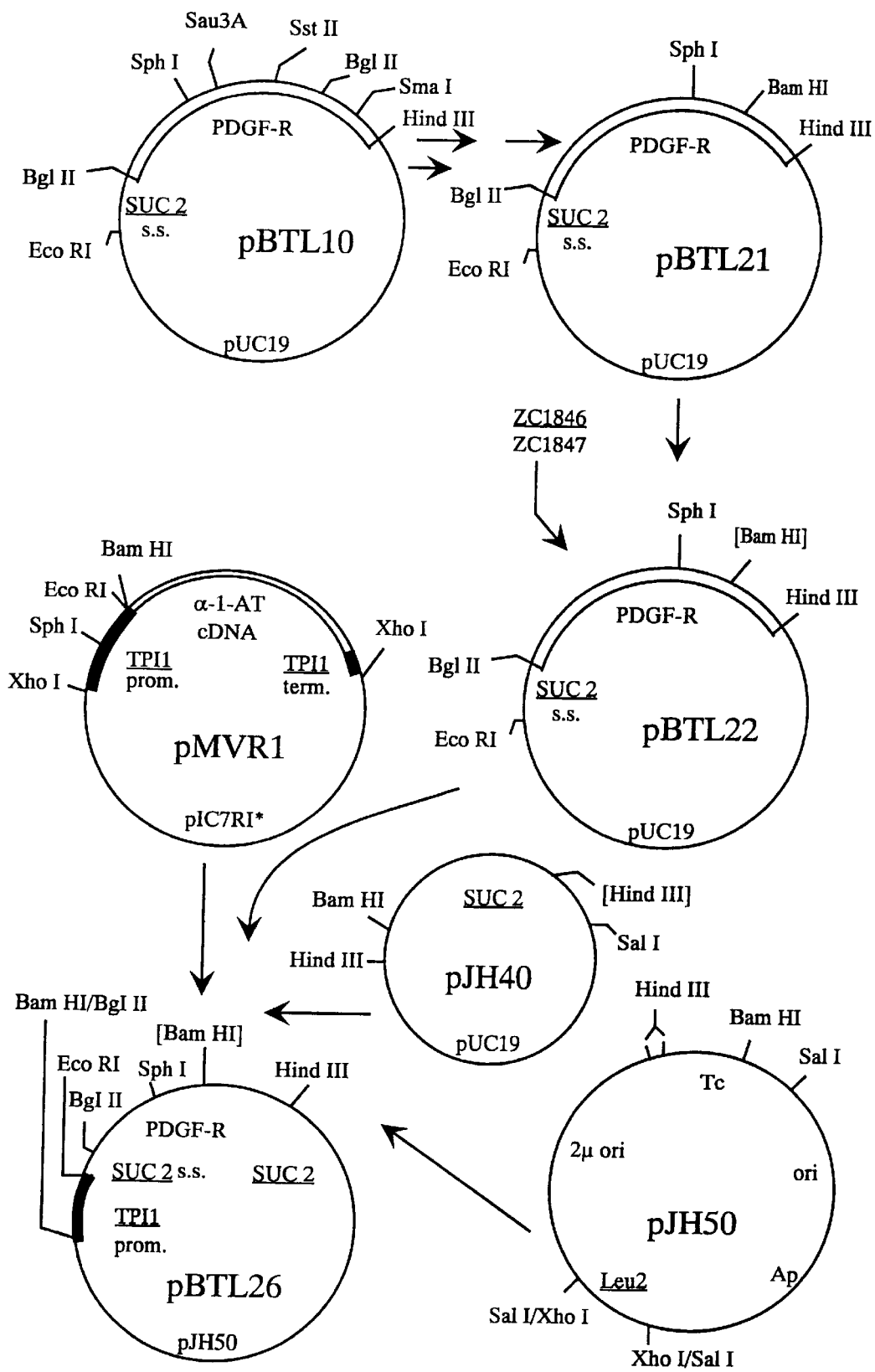
FIG. 6 illustrates the construction of pBTL22 and pBTL26.

The PDGFβ-R coding sequence present in pBTL10 was modified to delete the coding region 3' to the extracellular PDGFβ-R domain. As shown in FIG. 6, plasmid pBTL10 was digested with Sph I and Bam HI and with Sph I and Sst II to isolate the 4.77 kb fragment and the 466 bp fragment, respectively. The 466 bp fragment was then digested with Sau 3A to isolate the 0.17 kb fragment. The 0.17 kb fragment and the 4.77 kb were joined by ligation. The resultant plasmid was designated pBTL21.

Plasmid pBTL21, containing a Bam HI site that was regenerated by the ligation of the Bam HI and Sau 3A sites, was digested with Hind III and Bam HI to isolate the 4.2 kb fragment. Synthetic oligonucleotides ZC1846 (Sequence ID Number 16; Table 1) and ZC1847 (Sequence ID Number 17; Table 1) were designed to form an adapter encoding the PDGFβ-R from the Sau 3A site after bp 1856 (FIG. 1B; (Sequence ID Number 1)) to the end of the extracellular domain at 1958 bp (FIG. 1B; Sequence ID Number 1), having a 5' Bam HI adhesive end that destroys the Bam HI site and a 3' Hind III adhesive end. Oligonucleotides ZC1846 and ZC1847 were annealed under conditions described by Maniatis et. al. (ibid.). The 4.2 pBTL21 fragment and the ZC1846/ZC1847 adapter were joined by ligation. The resultant plasmid, designated pBTL22, comprises the SUC2 signal sequence fused in proper reading frame to the extracellular domain of PDGFβ-R in the vector pUC19 (FIG. 6).

B. Construction of pBTL28

An in-frame translation stop codon was inserted immediately after the coding region of the PDGFβ-R in pBTL22 using oligonucleotides ZC1892 (Sequence ID Number 19; Table 1) and ZC1893 (Sequence ID Number 20; Table 1). These oligonucleotides were designed to form an adapter encoding a stop codon in-frame with the PDGFβ-R coding sequence from pBTL22 flanked by a 5' Hind III adhesive end and a 3' Xba I adhesive end. Plasmid pBTL22 was digested with Eco RI and Hind III to isolate the 1.6 kb SUC2-PDGFβ-R fragment. Plasmid pMVR1 was digested with Eco RI and Xba I to isolate the 3.68 kb fragment comprising the TPI1 promoter, pIC7RI* vector sequences and the TPI1 terminator. Oligonucleotides ZC1892 and ZC1893 were annealed to form a Hind III-Xba I adapter. The 1.6 kb SUC2-PDGFβ-R fragment, the 3.86 kb pMVR1 fragment and the ZC1892/ZC1893 adapter were joined in a three-part ligation. The resultant plasmid was designated pBTL27.

The expression unit present in pBTL27 was inserted into the yeast expression vector pJH50 by first digesting pJH50 with Bam HI and Sal I to isolate the 10.3 kb vector fragment. Plasmid pBTL27 was digested with Bgl II and Eco RI and with Xho I and Eco RI to isolate the 0.9 kb TPI1 promoter fragment and the 1.65 kb fragment, respectively. The 10.3 kb pJH50 vector fragment, the 0.9 kb TPI1 promoter fragment and 1.65 kb fragment were joined in a three-part ligation. The resultant plasmid was designated pBTL28.

C. Construction of Plasmid pBTL30

The PDGFβ-R coding sequence present in plasmid pBTL22 was modified to encode the twelve C-terminal amino acids of substance P and an in-frame stop codon. Plasmid pBTL22 was digested with Eco RI and Hind III to isolate the 1.6 kb SUC2-PDGFβ-R fragment. Plasmid pMVR1 was digested with Eco RI and Xba I to isolate the 3.68 kb fragment comprising the TPI1 promoter, pIC7RI* and the TPI1 terminator. Synthetic oligonucleotides ZC1894 (Sequence ID Number 21; Table 1) and ZC1895 (Sequence ID Number 22; Table 1) were annealed to form an adapter containing the codons for the twelve C-terminal amino acids of substance P followed by an in-frame stop codon and flanked on the 5' end with a Hind III adhesive end and on the 3' end with an Xba I adhesive end. The ZC1894/ZC1895 adapter, the 1.6 kb SUC2-PDGFβ-R fragment and the pMVR1 fragment were joined in a three-part ligation. The resultant plasmid, designated pBTL29, was digested with Eco RI and Xho I to isolate the 1.69 kb SUC2-PDGFβ-R-subP-TPI1 terminator fragment. Plasmid pBTL27 was digested with Bgl II and Eco RI to isolate the 0.9 kb TPI1 promoter fragment. Plasmid pJH50 was digested with Bam HI and Sal I to isolate the 10.3 kb vector fragment. The 1.69 kb pBTL29 fragment, the 0.9 kb TPI1 promoter fragment and the 10.3 kb vector fragment were joined in a three-part ligation. The resulting plasmid was designated pBTL30.

EXAMPLE 9

Construction and Expression of a SUC2-PDGFβ-R-IgG Hinge Expression Vector

An expression unit comprising the TPI1 promoter, the SUC2 signal sequence, the PDGFβ-R extracellular domain, an immunoglobulin hinge region and the TPI1 terminator was constructed. Plasmid pBTL22 was digested with Eco RI and Hind III to isolate the 1.56 kb fragment. Plasmid pMVR1 was digested with Eco RI and Xba I to isolate the 3.7 kb fragment, comprising the TPI1 promoter, pIC7RI* vector sequences and the TPI1 terminator. Oligonucleotides ZC1776 (Sequence ID Number 14; Table 1) and ZC1777 (Sequence ID Number 15; Table 1) were designed to form, when annealed, an adapter encoding an immunoglobulin hinge region with a 5' Hind III adhesive end and a 3' Xba I adhesive end. Oligonucleotides ZC1776 and ZC1777 were annealed under conditions described by Maniatis et al. (ibid.). The 1.56 kb pBTL22 fragment, the 3.7 kb fragment and the ZC1776/ZC1777 adapter were joined in a three-part ligation, resulting in plasmid pBTL24.

The expression unit of pBTL24, comprising the TPI1 promoter, SUC2 signal sequence, PDGFβ-R extracellular domain sequence, hinge region sequence, and TPI1 terminator, was inserted into pJH50. Plasmid pBTL24 was digested with Xho I and Hind III to isolate the 2.4 kb expression unit. Plasmid pJH50 was digested with Hind III and Sal I to isolate the 9.95 kb fragment. The 2.4 kb pBTL24 fragment and 9.95 kb pJH50 vector fragment were joined by ligation. The resultant plasmid was designated pBTL25.

Plasmid pBTL25 was transformed into *Saccharomyces cerevisiae* strain ZY400 using the method essentially described by Beggs (ibid.). Transformants were selected for their ability to grow on -LEUDS (Table 2). The transformants were tested for their ability to bind the anti-PDGFβ-R monoclonal antibody PR7212 using the colony assay method described in Example 18. Plasmid pBTL25 transformants were patched onto nitrocellulose filters that had been wetted and supported by YEPD solid medium. Antibody PR7212 was found to bind to the PDGFβ-R-IgG hinge fusion secreted by ZY400[pBTL25] transformants.

EXAMPLE 10

Construction and Expression of a SUC2 signal sequence-PDGFβ-R Extracellular Domain-SUC2 Fusion As shown in FIG. 6, an expression unit comprising the TPI1 promoter, SUC2 signal sequence, PDGFβ-R extracellular domain sequence, and SUC2 coding sequence was constructed as follows. Plasmid pBTL22 was digested with Eco RI and Hind III to isolate the 1.6 kb SUC2-PDGFβ-R fragment. Plasmid pMVR1 was digested with Bgl II and Eco RI to isolate the 0.9 kb TPI1 promoter fragment. The SUC2 coding region was obtained from pJH40. Plasmid pJH40 was constructed by inserting the 2.0 kb Hind III-Hind III SUC2 fragment from pRB58 (Carlson et al., *Cell* 28:145–154, 1982) into the Hind III site of pUC19 followed by the destruction of the Hind III site 3' to the coding region. Plasmid pJH40 was digested with Hind III and Sal I to isolate the 2.0 kb SUC2 coding sequence. Plasmid pJH50 was digested with Sal I and Bam HI to isolate the 10.3 kb vector fragment. The 0.9 kb Bgl II-Eco RI TPI1 promoter fragment, the 1.6 kb Eco RI-Hind III SUC2-PDGFβ-R, the 2.0 kb Hind III-Sal I SUC2 fragment and the 10.3 kb Bam HI-Sal I vector fragment were joined in a four-part ligation. The resultant plasmid was designated pBTL26 (FIG. 6).

Plasmid pBTL26 was transformed into *Saccharomyces cerevisae* strain ZY400 using the method essentially described by Beggs (ibid.). Transformants were selected for their ability to grow on -LEUDS (Table 2). ZY400 transformants (ZY400[pBTL26]) were assayed by protein blot (Example 18), colony blot (Example 18) and competition assay.

Protein blot assays were carried out on ZY400[pBTL26] and ZY400[pJH50] (control) transformants that had been grown in flasks. Two hundred-fifty microliters of a 5 ml overnight cultures of ZY400[pBTL26] and ZY400 [pJH50] in -LEUDS+sodium succinate, pH 6.5 (Table 2) were inoculated into 50 ml of -LEUDS+sodium succinate, pH 6.5. The cultures were incubated for 35 hours in an airbath shaker at 30° C. The culture supernatants were harvested by centrifugation. The culture supernatants were assayed as described in Example 18 and were found to bind PR7212 antibody.

Colony assays were carried out on ZY400[pBTL26] transformants. ZY400[pBTL26] transformants were patched onto wetted nitrocellulose filters that were supported on a YEPD plate. The colony assay carried out as described in Example 8.A. showed that ZY400[pBTL26] antibodies bound PR7212 antibodies.

Competition binding assays were carried out on ZY400 [pBTL26] and ZY400[pJH50] transformants. The transformants were grown in two liters of fermentation medium (Table 2) in a New Brunswick Bioflo2 fermentor (New Brunswick, Philadelphia, Pa.) with continuous pH control at pH 6.4. The cultures were adjusted to pH 7.5 immediately prior to harvesting. Culture supernatants were concentrated in an Amicon concentrator (Amicon, San Francisco, Calif.) using an Amicon $10^4$ mw spiral filter cartridge. The concentrated supernatants were further concentrated using Amicon Centriprep 10's. Fifteen milliliters of the concentrated supernatant samples were added to the Centripreps, and the Centripreps were spun in a Beckman GRP centrifuge (Beckman Instruments Inc., Carlsbad, Calif.) at setting 5 for a total of 60 minutes. The concentrates were removed from the Centripreps and were assayed in the competition assay.

The competition binding assay measured the amount of $^{125}$I-PDGF left to bind to fetal foreskin fibroblast cells after preincubation with the concentrate containing the PDGFβ-R-SUC2 fusion protein. PDGF-AA and PDGF-AB were iodinated using the Iodopead method (Pierce Chemical). PDGF-BB$_{Tyr}$ was iodinated and purified as described in Example 18.F. The concentrate was serially diluted in binding medium (Table 4). The dilutions were mixed with 0.5 ng of iodinated PDGF-AA, PDGF-BB$_{Tyr}$ or PDGF-AB, and the mixtures were incubated for two hours at room temperature. Three hundred micrograms of unlabeled PDGF-BB was added to each sample mixture. The sample mixtures were added to 24-well plates containing confluent fetal foreskin fibroblast cells (AG1523, available from the Human Genetic Mutant Cell Repository, Camden, N.J.). The cells were incubated with the mixture for four hours at 4° C. The supernatants were aspirated from the wells, and the wells were rinsed three times with phosphate buffered saline that was held at 4° C. (PBS; Sigma, St. Louis, Mo.). Five hundred microliters of PBS+1% NP-40 was added to each well, and the plates were shaken on a platform shaker for five minutes. The cells were harvested and the amount of iodinated PDGF was determined. The results of the competition binding assay showed that the PDGFβ-R-SUC2 fusion protein was able to competitively bind all three isoforms of PDGF.

The PDGFβ-R produced from ZY400 [pBTL26] transformants was tested for cross reactivity to fibroblast growth factor (FGF) and transforming growth factor-β(TGF-β) using the competition assay essentially described above. Supernatant concentrates from ZY400[pBTL26] and ZY400 [JH50] (control) transformants were serially diluted in binding medium (Table 4). The dilutions were mixed with 7.9 ng of iodinated FGF or 14 ng of iodinated TGF-β, and the mixtures were incubated for two hours at room temperature. Fourteen micrograms of unlabeled FGF was added to each mixture containing labeled FGF, and 7 μg of unlabeled TGF-β was added to each mixture containing labeled TGF-β. The sample mixtures were added to 24-well plates containing confluent human dermal fibroblast cells. (Human dermal fibroblast cells express both FGF receptors and TGFβ receptors.) The cells were incubated with the mixtures for four hours at 4° C. Five hundred microliters of PBS+1% NP-40 was added to each well, and the plates were shaken on a platform shaker for five minutes. The cells were harvested and the amount of iodinated FGF or TGF-β bound to the cells was determined. The results of these assays showed that the PDGFβ-R-SUC2 fusion protein did not cross react with FGF or TGF-β.

TABLE 4

Reagent Recipes

Binding Medium
500 ml Ham's F-12 medium
12 ml 1M HEPES, pH 7.4
5 ml 100×PSN (Penicillin/Streptomycin/Neomycin, Gibco)
1 g rabbit serum albumin
Western Transfer Buffer
25 mM Tris, pH 8.3
19 mM glycine, pH 8.3
20% methanol
Western Buffer A
50 ml 1M Tris, pH 7.4
20 ml 0.25 mM EDTA, pH 7.0
5 ml 10% NP-40
37.5 ml 4M NaCl
2.5 g gelatin The Tris, EDTA, NP-40 and NaCl were diluted to a final volume of one liter with distilled water. The gelatin was added to 300 ml of this solution and the solution was heated in a microwave until the gelatin was in solution. The gelatin solution was added back to the remainder of the first solution and stirred at 4° C. until cool. The buffer was stored at 4° C.

Western Buffer B
50 ml 1M Tris, pH 7.4
20 ml 0.25M EDTA, pH 7.0
5 ml 10% NP-40
58.4 g NaCl
2.5 g gelatin
4 g N-lauroyl sarcosine The Tris, EDTA, NP-40, and the NaCl were mixed and diluted to a final volume of one liter. The gelatin was added to 300 ml of this solution and heated in a microwave until the gelatin was in solution. The gelatin solution was added back to the original solution and the N-lauroyl sarcosine was added. The final mixture was stirred at 4° C. until the solids were completely dissolved. This buffer was stored at 4° C.

2×Loading Buffer
36 ml 0.5M Tris-HCl, pH 6.8
16 ml glycerol
16 ml 20% SDS
4 ml 0.5% Bromphenol Blue in 0.5M Tris-HCl, pH 6.8

Mix all ingredients. Immediately before use, add 100 μl β-mercaptoethanol to each 900 μl dye mix

EXAMPLE 11

Construction and Expression of PDGF Receptor Analogs From BHK Cells

A. Construction of pBTL114 and pBTL115

The portions of the PDGF α-receptor extracellular domain present in pBTL14 and pBTL15 were placed in a mammalian expression vector. Plasmids pBTL14 and pBTL15 were digested with Eco RI to isolate the 1695 bp and 1905 bp SUC2 signal-PDGFβ-R-BAR1 fragments. The 1695 bp fragment and the 1905 bp fragment were each ligated to Zem229R that had been linearized by digestion with Eco RI.

Figure 10:
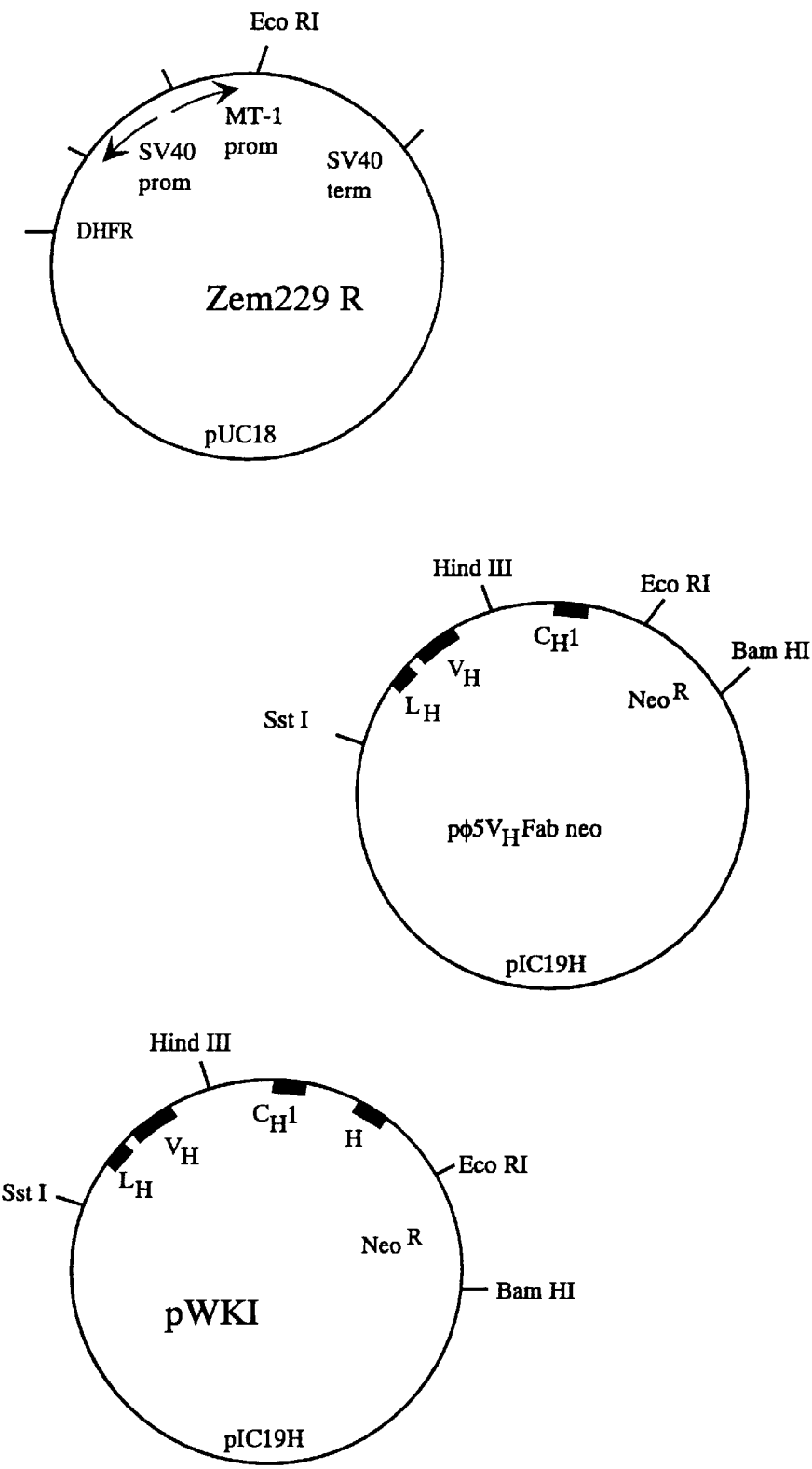
FIG. 10 illustrates the constructions Zem229R, p$\phi$5V$_H$Fab-neo and pWKI. Symbols used are set forth in FIG. 9.

The vector Zem229R was constructed as shown in FIG. 10 from Zem229. Plasmid Zem229 is a pUC18-based expression vector containing a unique Bam HI site for insertion of cloned DNA between the mouse metallothionein-1 promoter and SV40 transcription terminator and an expression unit containing the SV40 early promoter, mouse dihydrofolate reductase gene, and SV40 transcription terminator. Zem229 was modified to delete the Eco RI sites flanking the Bam HI cloning site and to replace the Bam HI site with a single Eco RI cloning site. The plasmid was partially digested with Eco RI, treated with DNA polymerase I (Klenow fragment) and dNTPs, and religated. Digestion of the plasmid with Bam HI followed by ligation of the linearized plasmid with a Bam HI-Eco I adapter resulted in a unique Eco RI cloning site. The resultant plasmid was designated Zem229R.

Figure 9:
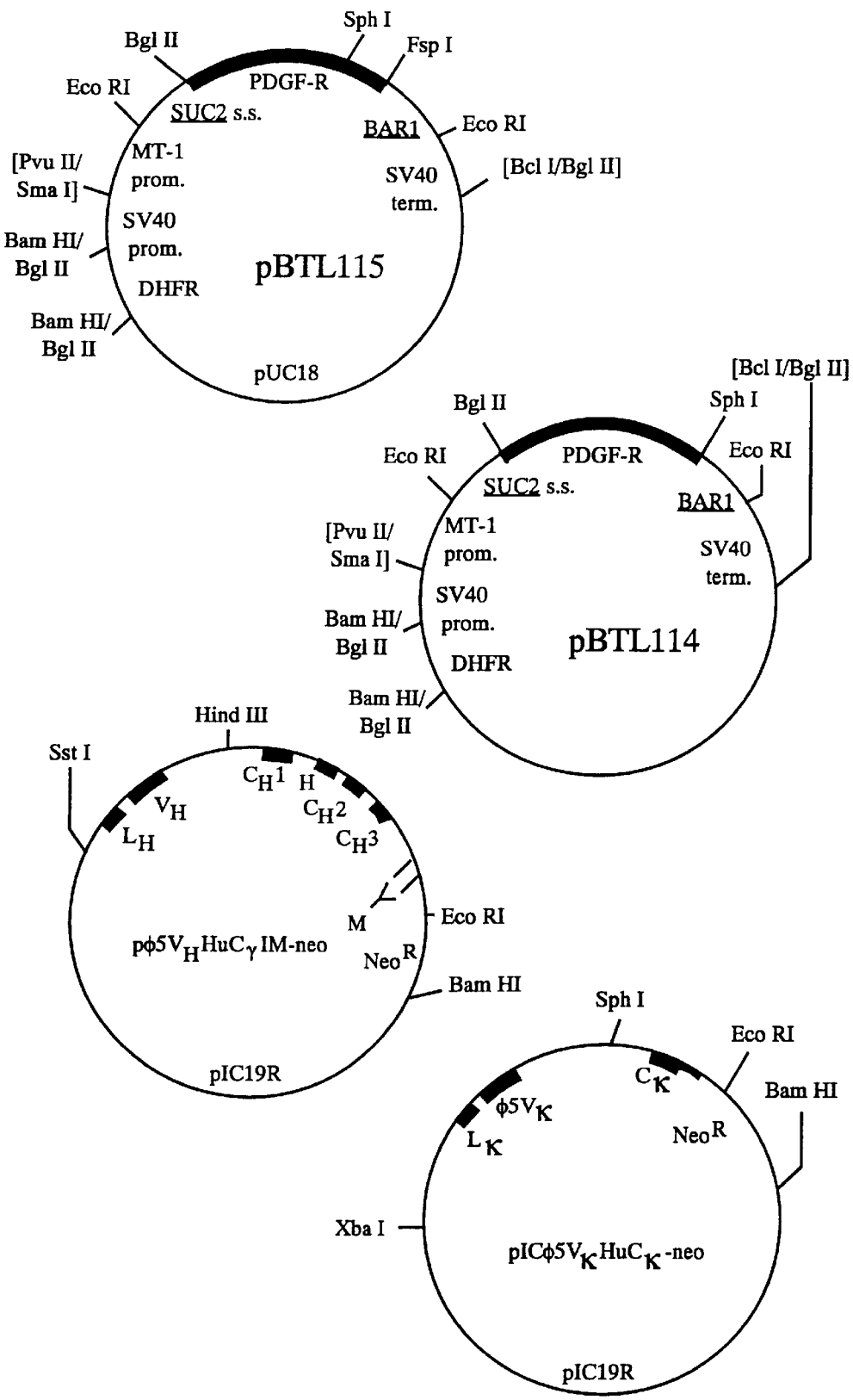
FIG. 9 illustrates the constructions pBTL115, pBTL114, p$\phi$5V$_H$HuC$_\gamma$1M-neo, plC$\phi$5V$_\kappa$HuC$_\kappa$-neo. Symbols used are set forth in FIGS. 7 and 8, and also include L$_H$, mouse immunoglobulin heavy chain signal sequence; V$_H$, mouse immunoglobulin heavy chain variable region sequence; E, mouse immunoglobulin heavy chain enhancer sequence; L$_\kappa$, mouse immunoglobulin light chain signal sequence; $\phi$5V$_\kappa$, mouse immunoglobulin light chain variable region sequence; Neo$^R$, *E. coli* neomycin resistance gene.

The ligation mixtures were transformed into *E. coli* strain RR1. Plasmid DNA was prepared and the plasmids were subjected to restriction enzyme analysis. A plasmid having the 1695 bp pBTL14 fragment inserted into Zem229R in the correct orientation was designated pBTL14 (FIG. 9). A plasmid having the 1905 bp pBTL15 fragment inserted into Zem229R in the correct orientation was designated pBTL115 (FIG. 9).

B. Expression of Secreted PDGF α-Receptor Analogs in tk$^{13}$ tsl3 BHK Cells

Plasmids pBTL114 and pBTL115 were each transfected into tk$^{13}$-tsl3 cells using calcium phosphate precipitation (essentially as described by Graham and van der Eb, *J. Gen. Virol.* 36: 59–72, 1977). The transfected cells were grown in Dulbecco's modified Eagle's medium (DMEM) containing 10% fetal calf serum, 1×PSN antibiotic mix (Gibco 600-5640), 2.0 mM L-glutamine. The cells were selected in 250 nM methotrexate (MTX) for 14 days, and the resulting colonies were screened by the immunofilter assay (McCracken and Brown, *Biotechniques*, 82–87, March/April 1984). Plates were rinsed with PBS or No Serum medium (DMEM plus 1×PSN antibiotic mix). Teflon® mesh (Spectrum Medical Industries, Los Angeles, Calif.) was then placed over the cells. Nitrocellulose filters were wetted with PBS or No Serum medium, as appropriate, and placed over the mesh. After six hours incubation at 37° C., filters were removed and placed in Wester buffer A (Table 4) overnight at room temperature. The filters were developed using the antibody PR7212 and the procedure described in Example 8. The filters showed that conditioned media from pBTL114-transfected and pBTL115-transfected BHK cells bound the PR7212 antibody indicating the presence of biologically active secreted PDGFβ-R.

EXAMPLE 12

Expression of PDGF β-receptor Analogs in Cultured Mouse Myeloma Cells

A. Construction of pICμPRE8

The immunoglobulin μ heavy chain promoter and enhancer were subcloned into pIC19H to provide a unique Hind III site 3' to the promoter. Plasmid pμ (Grosschedl and Baltimore, *Cell* 41: 885–897, 1985) was digested with Sal I and Eco RI to isolate the 3.1 kb fragment comprising the μ promoter. Plasmid pIC19H was linearized by digestion with Eco RI and Xho I. The μ promoter fragment and the linearized pIC19H vector fragment were joined by ligation. The resultant plasmid, designated pICμ3, was digested with Ava II to isolate the 700 bp μ promoter fragment. The 700 bp fragment was blunt-ended by treatment with DNA polymerase I (Klenow fragment) and deoxynucleotide triphosphates. Plasmid pIC19H was linearized by digestion with Xho I, and the adhesive ends were filled in by treatment with DNA polymerase I (Klenow fragment) and deoxynucleotide triphosphates. The blunt-ended Ava II fragment was ligated with the blunt-ended, linearized pIC19H, and the ligation mixture was transformed into *E. coli* JM83. Plasmid DNA was prepared from the transformants and was analyzed by restriction digest. A plasmid with a Bgl II site 5' to the promoter was designated pICμPR1(−). Plasmid pICμPR1(−) was digested with Hind III and Bgl II to isolate the 700 bp μ promoter fragment. Plasmid pIC19R was linearized by digestion with Hind III and Bam HI. The 700 bp promoter fragment was joined with the linearized pIC19R by ligation. The resultant plasmid, designated pICμPR7, comprised the μ promoter with an unique Sma I site 5' to the promoter and a unique Hind III site 3' to the promoter.

Figure 7:
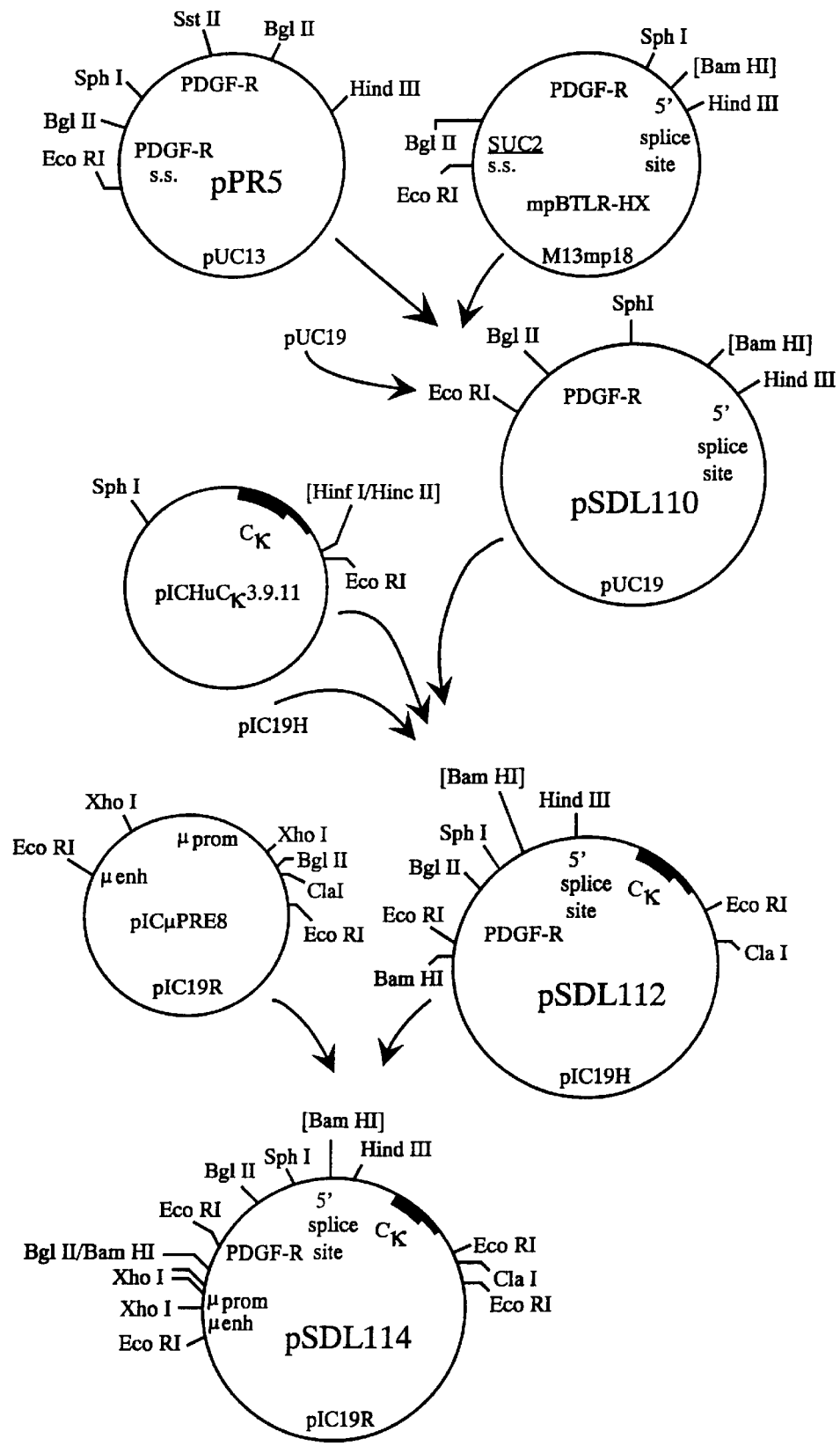
FIG. 7 illustrates the construction of pSDL114. Symbols used are S.S., signal sequence, $C_k$, immunoglobulin light chain constant region sequence; $\mu$prom, $\mu$ promoter, $\mu$ enh; $\mu$ enhancer.

The immunoglobulin heavy chain μ enhancer (Gillies et al., *Cell* 33: 717–728, 1983) was inserted into the unique Sma I site to generate plasmid pICμPRE8. Plasmid pJ4 (obtained from F. Blattner, Univ. Wisconsin, Madison, Wis.), comprising the 1.5 kb Hind III-Eco RI μ enhancer fragment in the vector pAT153 (Amersham, Arlington Heights, Ill.), was digested with Hind III and Eco RI to isolate the 1.5 kb enhancer fragment. The adhesive ends of the enhancer fragment were filled in by treatment with T4 DNA polymerase and deoxynucleotide triphosphates. The blunt-ended fragment and pICμPR7, which had been linearized by digestion with Sma I, were joined by ligation. The ligation mixture was transformed into *E. coli* RR1. Plasmid DNA was prepared from the transformants, and the plasmids were analyzed by restriction digests. A plasmid comprising the μ enhancer and the A promoter was designated pICμPRE8 (FIG. 7).

B. Construction of pSDL114

The DNA sequence encoding the extracellular domain of the PDGF α-receptor was joined with the DNA sequence encoding the human immunoglobulin light chain constant region. The PDGF β-receptor extracellular domain was obtained from mpBTL22, which comprised the Eco RI-Hind III fragment from pBTL22 (Example 8.A.) cloned into Eco RI-Hind III cut M13mpl8. Single stranded DNA was prepared from a mpBTL22 phage clone, and the DNA was subjected to in vitro mutagenesis using the oligonucleotide ZC1886 (Table 1) and the method described by Kunkel (*Proc. Natl. Acad. Sci. USA* 82: 488–492, 1985). A phage clone comprising the mutagenized PDGFβ-R with a donor splice site (5' splice site) at the 3' end of the PDGFβ-R extracellular domain was designated pBTLR-HX (FIG. 7).

The native PDGFβ-R signal sequence was obtained from pPR5. Plasmid pPR5, comprising 738 bp of 5' coding sequence with an Eco RI site immediately 5' to the translation initiation codon, was constructed by in vitro mutagenesis of the PDGFβ-R cDNA fragment from RP51 (Example 1). Replicative form DNA of RP51 was digested with Eco RI to isolate the 1.09 kb PDGFβ-R fragment. The PDGFβ-R fragment was cloned into the Eco RI site of M13mp18. Single stranded template DNA was prepared from a phage clone containing the PDGFβ-R fragment in the proper orientation. The template DNA was subjected to in vitro mutagenesis using oligonucleotide ZC1380 (Sequence ID Number 8; Table 1) and the method described by Zoller and Smith (*Meth. Enzymol.* 100: 468–500, 1983). The mutagenesis resulted in the placement of an Eco RI site immediately 5' to the translation initiation codon. Mutagenized phage clones were analyzed by dideoxy sequence analysis. A phage clone containing the ZC1380 mutation was selected, and replicative form (Rf) DNA was prepared from the phage clone. The Rf DNA was digested with Eco RI and Acc I to isolate the 0.63 kb fragment. Plasmid pR-RXI (Example 1) was digested with Acc I and Eco RI to isolate the 3.7 kb fragment. The 0.63 kb fragment and the 3.7 kb fragment were joined by ligation resulting in plasmid pPR5 (FIG. 7).

As shown in FIG. 7, the PDGFβ-R signal peptide and part of the extracellular domain were obtained from plasmid pPR5 as a 1.4 kb Eco RI-Sph I fragment. Replicative form DNA from phage clone pBTLR-HX was digested with Sph I and Hind III to isolate the approximately 0.25 kb PDGFβ-R fragment. Plasmid pUC19 was linearized by digestion with Eco RI and Hind III. The 1.4 kb Eco RI-Sph I PDGFβ-R fragment, the 0.25 kb Sph I-Hind III fragment from PBTLR-HX and the Eco RI-Hind III cut pUC19 were joined in a three-part ligation. The resultant plasmid, pSDL110, was digested with Eco RI and Hind III to isolate the 1.65 kb PDGFβ-R fragment.

Plasmid pICHuCκ3.9.11 was used as the source of the human immunoglobulin light chain gene (FIG. 7). The human immunoglobulin light chain gene was isolated from a human genomic library using an oligonucleotide probe (5'TGT GAC ACT CTC CTG GGA GTT A 3'; Sequence ID Number 32), which was based on a published human kappa C gene sequence (Hieter et al., *Cell* 22: 197–207, 1980). The human light chain (kappa) constant region was subcloned as a 1.1 kb Sph I-Hinf I genomic fragment of the human kappa gene, which has been treated with DNA polymerase DNA I (Klenow Fragment) to fill in the Hinf I adhesive end, into Sph I-Hinc II cut pUC19. The 1.1 kb human kappa constant region was subsequently isolated as a 1.1 kb Sph I-Bam HI fragment that was subcloned into Sph I-Bgl II cut pIC19R (Marsh et al., ibid.). The resultant plasmid was designated pICHuCλ3.9.11. Plasmid pICHuC$_K$3.9.11 was digested with Hind III and Eco RI to isolate the 1.1 kb kappa constant region gene. Plasmid pIC19H was linearized by digestion with Eco RI. The 1.65 kb PDGFβ-R fragment, the 1.1 kb human kappa constant region fragment and the linearized pIC19H were joined in a three part ligation. The resultant plasmid, pSDL112, was digested with Bam HI and Cla I to isolate the 2.75 kb fragment. Plasmid pμPRE8 was linearized with Bgl II and Cla I. The 2.75 kb fragment and the linearized pμPRE8 were joined by ligation. The resultant plasmid was designated pSDL114 (FIG. 7).

Plasmid pSDL114 was linearized by digestion with Cla I and was cotransfected with Pvu I-digested p416 into SP2/0-Ag14 (ATCC CRL 1581) by electroporation using the method essentially described by Neumann et al. (*EMBO J.* 1: 841–845, 1982). (Plasmid p416 comprises the Adenovirus 5 70 ori, SV40 enhancer, Adenovirus 2 major late promoter, Adenovirus 2 tripartite leader, 5' and 3' splice sites, the DHFR$^r$ cDNA, the SV40 polyadenylation signal and pML-1 (Lusky and Botchan, *Nature* 293: 79–81, 1981) vector sequences.) Transfectants were selected in growth medium containing methotrexate.

Media from drug resistant clones were tested for the presence of secreted PDGF β-receptor analogs by enzyme-linked immunosorbant assay (ELISA). Ninety-six well assay plates were prepared by incubating 100 μl of 1 μg/ml polyclonal goat anti-human kappa chain (Cappel Laboratories, Melvern, Pa.) diluted in phosphate buffered saline (PBS; Sigma) overnight at 4° C. Excess antibody was removed by three washes with 0.5% Tween 20 in PBS. One hundred microliters of spent media was added to each well, and the well were incubated for one hour at 4° C. Unbound proteins were removed by eight washes with 0.5% Tween 20 in PBS. One hundred microliters of peroxidase-conjugated goat anti-human kappa antibody (diluted 1:1000 in a solution containing 5% chicken serum (GIBCO-BRL)+0.5% Tween 20 in PBS) was added to each well and the wells were incubated for one hour at 4° C. One hundred microliters of chromophore (100 μl ABTS (2,2'-Azinobis(3-ethylbenzthiazoline sulfonic acid) diammonium salt; Sigma)+1 μl 30% $H_2O_2$+12.5 ml citrate/phosphate buffer (9.04 g/l citric acid, 10.16 g/l $Na_2HPO_4$)) was added to each well, and the wells were incubated to thirty minutes at room temperature. The samples were measured at 405 nm. The results of the assay showed that the PDGFβ-R analog secreted by the transfectants contained an immunoglobulin light chain.

Spent media from drug resistant clones was also tested for the presence of secreted PDGF β-receptor analogs by immunoprecipitation. Approximately one million drug resistant transfectants were metabolically labeled by growth in DMEM medium lacking cysteine+2% calf serum for 18 hours at 37° C. in the presence of 50 μCI $^{35}$S-cysteine.

Media was harvested from the labeled cells and 250 Al of the spent media was assayed by immunoprecipitation with the anti-PDGF β-receptor antibody PR7212 to detect the presence of metabolically labeled PDGF β-receptor analogs. PR7212, diluted in PBS, was added to the media to a final concentration of 2.5 μg per 250 μl spent media. Five microliters of rabbit anti-mouse Ig diluted in PBS was added to the PR7212/media mixtures. The immunocomplexes were precipitated by the addition of 50 Al 10% fixed Staph A (weight/volume in PBS). The immunocomplexes were analyzed on 8% SDS-polyacrylamide gels followed by autoradiography overnight at −70° C. The results of the immunoprecipitation showed that the PDGF β-receptor analog secreted by the transfectants was bound by the anti-PDGF β-receptor antibody. The combined results of the ELISA and immunoprecipitation assays showed that the PDGF β-receptor analog secreted by the transfectants contained both the PDGF β-receptor ligand-binding domain and the human light chain constant region.

C. Cotransfection of pSDL114 With an Immunoglobulin Heavy Chain

Plasmid pSDL114 was cotransfected with pϕ5V$_H$huC$_γ$1M-neo, which encodes a neomycin resistance gene expression unit and a complete mouse/human chimeric immunoglobulin heavy chain gene expression unit.

Plasmid pϕ5V$_H$huC$_γ$1M-neo was constructed as follows. The mouse immunoglobulin heavy chain gene was isolated from a lambda genomic DNA library constructed from the murine hybridoma cell line NR-ML-05 (Serafini et al., *Eur. J. Nucl. Med.* 14: 232, 1988) using an oligonucleotide probe designed to span the V$_H$/D/J$_H$ junction (5' GCA TAG TAG TTA CCA TAT CCT CTT GCA CAG 3'; Sequence ID Number 33). The human immunoglobulin gamma-1 C gene was isolated from a human genomic library using a cloned human gamma-4 constant region gene (Ellison et al., *DNA* 1: 11–18, 1981). The mouse immunoglobulin variable region was isolated as a 5.3 kb Sst I-Hind III fragment from the original phage clone and the human gamma-i C gene was obtained from the original phage clone as a 6.0 kb Hind III-Xho I fragment. The chimeric gamma-1 C gene was created by joining the VH and CH fragments via the common Hind III site and incorporating them with the *E. coli* neomycin resistance gene expression unit into pIC19H to yield pϕ5V$_H$huC$_γ$1M-neo.

Plasmid pSDL114 was linearized by digestion with Cla I and was co-transfected into SP2/0-Ag14 cells with Asp 718 linearized pϕ5V$_H$huC$_{651}$M-neo. The transfectants were selected in growth medium containing methotrexate and neomycin. Media from drug-resistant clones were tested for their ability to bind PDGF in a competition binding assay.

The competition binding assay measured the amount of $^{125}$I-PDGF left to bind to human dermal fibroblast cells after preincubation with the spent media from pSDL114- pφ5V$_H$huC$_γ$1M-neo transfected cells. The media were serially diluted in binding medium (Table 4). The dilutions were mixed with 0.5 ng of iodinated PDGF-BB or iodinated PDGF-AA, and the mixtures were incubated for two hours at room temperature. Three hundred micrograms of unlabeled PDGF-BB or unlabeled PDGF-AA was added to one tube from each series. The sample mixtures were added to 24 well plates containing confluent human dermal fibroblast cells. The cells were incubated with the mixture for four hours at 4° C. The supernatants were aspirated from the wells, and the wells were rinsed three times with phosphate buffered saline that was held a 4° C. (PBS; Sigma, St. Louis, Mo.). Five hundred microliters of PBS+1% NP-40 was added to each well, and the plates were shaken on a platform shaker for five minutes. The cells were harvested and the amount of iodinated PDGF was determined. The results of the competition binding assay showed that the protein produced from pSDL114-pφ5V$_H$huC$_γ$1M-neo transfected cells was able to competitively bind PDGF-BB but did not bind PDGF-AA.

The PDGF β-receptor analog produced from a pSDL114-pφ5V$_H$huC$_γ$1M-neo transfectant was assayed to determine if the receptor analog was able to bind PDGF-BB with high affinity. Eight and one half milliliters of spent media containing the PDGFβ-R analogs from a pSDL114-p5V$_H$huC$_{65}$1M-neo transfectant was added to 425 μl of Sepharose Cl-4B-Protein A beads (Sigma, St. Louis, Mo.), and the mixture was incubated for 10 minutes at 4° C. The beads were pelleted by centrifugation and washed with binding medium (Table 4). Following the wash the beads were resuspended in 8.5 ml of binding media, and 0.25 ml aliquots were dispensed to 1.5 ml tubes. Binding reactions were prepared by adding iodinated PDGF-BB$_{Tyr}$ (Example 18.F.) diluted in DMEM+10% fetal calf serum to the identical aliquots of receptor-bound beads to final PDGF-BB$_{Tyr}$ concentrations of between 4.12 pM and 264 pM. Nonspecific binding was determined by adding a 100 fold excess of unlabeled BB to an identical set of binding reactions. Mixtures were incubated overnight at 4° C.

The beads were pelleted by centrifugation, and unbound PDGF-BB was removed with three washes in PBS. The beads were resuspended in 100 μl of PBS and were counted. Results of the assay showed that the PDGFβ-R analog was able to bind PDGF-BB with high affinity.

D. Construction of pSDL113

Figure 8:
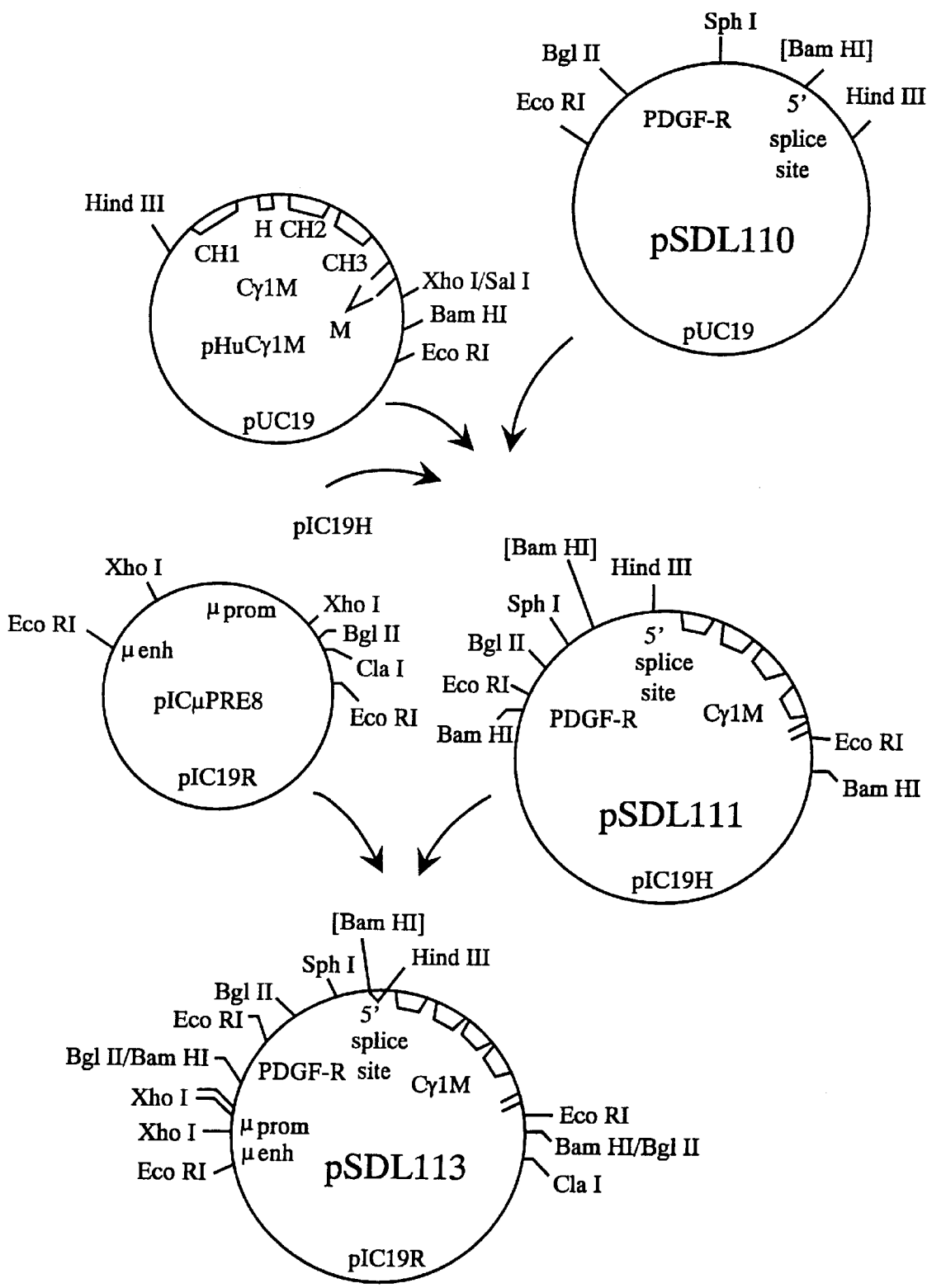
FIG. 8 illustrates the construction of pSDLB113. Symbols used are S.S., signal sequence; $C_H1$, $C_H2$, $C_H3$, immunoglobulin heavy chain constant region domain sequences; H, immunoglobulin heavy chain hinge region sequence; M, immunoglobulin membrane anchor sequences; C$\gamma$1M, immunoglobulin heavy chain constant region and membrane anchor sequences.

As shown in FIG. 8, the DNA sequence encoding the extracellular domain of the PDGF β-receptor was joined with the DNA sequence encoding a human immunoglobulin heavy chain constant region joined to a hinge sequence. Plasmid pSDL110 was digested with Eco RI and Hind III to isolate the 1.65 kb PDGFβ-R fragment. Plasmid pICHu$_γ$-1M was used as the source of the heavy chain constant region and hinge region. Plasmid pICHu$_γ$-1M comprises the approximately 6 kb Hind III-Xho I fragment of a human gamma-1 C gene subcloned into pUC19 that had been linearized by digestion with Hind III and Sal I. Plasmid pICu$_γ$-1M was digested with Hind III and Eco RI to isolate the 6 kb fragment encoding the human heavy chain constant region. Plasmid pIC19H was linearized by digestion with Eco RI. The 1.65 kb PDGFβ-R fragment, the 6 kb heavy chain constant region fragment and the linearized pIC19H were joined in a three part ligation. The resultant plasmid, pSDL111, was digested with Bam HI to isolate the 7.7 kb fragment. Plasmid pμPRE8 was linearized with Bgl II and was treated with calf intestinal phosphatase to prevent self-ligation. The 7.7 kb fragment and the linearized pμPRE8 were joined by ligation. A plasmid containing the insert in the proper orientation was designated pSDL113 (FIG. 8).

Plasmid pSDL113 is linearized by digestion with Cla I and is cotransfected with Pvu I-digested p416 into SP2/0-Ag14 by electroporation. Transfectants are selected in growth medium containing methotrexate.

Media from drug resistant clones are tested for the presence of secreted PDGFβ-R analogs by immunoprecipitation using the method described in Example 12.B.

E. Cotransfection of pSDL113 With an Immunoglobulin Light Chain Gene

Plasmid pSDL113 is linearized by digestion with Cla I and was cotransfected with pICφ5V$_κ$HuC$_κ$-Neo, which encodes a neomycin resistance gene and a mouse/human chimeric immunoglobulin light chain gene. The mouse immunoglobulin light chain gene was isolated from a lambda genomic DNA library constructed from the murine hybridoma cell line NR-ML-05 (Woodhouse et al., ibid.) using an oligonucleotide probe designed to span the V$_κ$/J$_κ$ junction (5' ACC GAA CGT GAG AGG AGT GCT ATA A 3'; Sequence ID Number 34). The human immunoglobulin light chain constant region gene was isolated as described in Example 12.B. The mouse NR-ML-05 immunoglobulin light chain variable region gene was subcloned from the original mouse genomic phage clone into pIC19R as a 3 kb Xba I-Hinc II fragment. The human kappa C gene was subcloned from the original human genomic phage clone into pUC19 as a 2.0 kb Hind III-Eco RI fragment. The chimeric kappa gene was created by joining the NR-ML-05 light chain variable region gene and human light chain constant region gene via the common Sph I site and incorporating them with the E. coli neomycin resistance gene into pIC19H to yield pICφ5V$_κ$HuC$_κ$-Neo (FIG. 9).

The linearized pSDL113 and pICφ5V$_κ$HuC$_κ$-Neo are transfected into SP2/0-Ag14 cells by electroporation. The transfectants are selected in growth medium containing methotrexate and neomycin.

F. Cotransfection of pSDL113 and pSDL114

A clone of SP2/0-Ag14 stably transfected with pSDL114 and p416 was co-transfected with Cla I-digested pSDL113 and Bam HI-digested pICneo by electroporation. (Plasmid pICneo comprises the SV40 promoter operatively linked to the E. coli neomycin resistance gene and pIC19H vector sequences.) Transfected cells were selected in growth medium containing methotrexate and G418. Media from drug-resistant clones were tested for their ability to bind PDGF-BB or PDGF-AA in a competition binding assay as described in Example 12.C. The results of the assay showed that the transfectants secreted a PDGF β-receptor analog which was capable of competitively binding PDGF-BB but did not detectably bind to PDGF-AA.

G. Cotransfection of pSDL114 With Fab

A clone of SP2/0-AG14 stably transfected with pSDL114 and p416 was transfected with the Fab region of the human gamma-4 gene ($γ_4$) in plasmid pφ5V$_H$Fab-neo.

Plasmid pφ5V$_H$Fab-neo was constructed by first digesting plasmid p24BRH (Ellison et al., *DNA* 1: 11, 1988) was digested with Xma I and Eco RI to isolate the 0.2 kb fragment comprising the immunoglobulin 3' untranslated region. Synthetic oligonucleotides ZC871 (Sequence ID Number 3; Table 1) and ZC872 (Sequence ID Number 4; Table 1) were kinased and annealed using essentially the methods described by Maniatis et al. (ibid.). The annealed oligonucleotides ZC871/ZC872 formed an Sst I-Xma I adapter. The ZC871/ZC872 adapter, the 0.2 kb p24BRH fragment and Sst I-Eco RI linearized pUC19 were joined in a three-part ligation to form plasmid pγ$_4$3'. Plasmid pγ$_4$3' was linearized by digestion with Bam HI and Hind III. Plasmid p24BRH was cut with Hind III and Bgl II to isolate the 0.85 kb fragment comprising the $C_H1$ region. The $p\gamma_43'$ fragment and the Hind III-Bgl II p24BRH fragment were joined by ligation to form plasmid $p\gamma_4Fab$. Plasmid $p\gamma_4Fab$ was digested with Hind III and Eco RI to isolate the 1.2 kb fragment comprising $\gamma_4Fab$. Plasmid pICneo, comprising the SV40 promoter operatively linked to the *E. coli* neomycin resistance gene and pIC19H vector sequences, was linearized by digestion with Sst I and Eco RI. Plasmid $p\phi5V_H$, comprising the mouse immunoglobulin heavy chain gene variable region and pUC18 vector sequences, was digested with Sst I and Hind III to isolate the 5.3 kb $V_H$ fragment. The linearized pICneo was joined with the 5.3 kb Sst I-Hind III fragment and the 1.2 kb Hind III-Eco RI fragment in a three-part ligation. The resultant plasmid was designated $p\phi5V_H$Fab-neo (FIG. 10).

A pSDL114/p416-transfected SP2/0-AG14 clone was transfected with Sca I-linearized $p\phi5V_H$Fab-neo. Transfected cells were selected in growth medium containing methotrexate and G418. Media from drug-resistant clones were tested for their ability to bind PDGF in a competition binding assay as described in Example 12.C. The results of the assay showed that the PDGF β-receptor analog secreted from the transfectants was capable of competitively binding PDGF-BB.

H. Cotransfection of pSDL114 with Fab'

A stably transfected SP2/0-AG14 isolate containing pSDL114 and p416 was transfected with plasmid pWKI, which contained the Fab' portion of an immunoglobulin heavy chain gene. Plasmid pWKI was constructed as follows.

The immunoglobulin gamma-1 Fab' sequence, comprising the $C_H1$ and hinge regions sequences, was derived from the gamma-1 gene clone described in Example 12.C. The gamma-1 gene clone was digested with Hind III and Eco RI to isolate the 3.0 kb fragment, which was subcloned into Hind III-Eco RI linearized M13mpl9. Single-stranded template DNA from the resultant phage was subjected to site-directed mutagenesis using oligonucleotide ZC1447 (Sequence ID Number 9; Table 1) and essentially the method of Zoller and Smith (ibid.). A phage clone was identified having a ZC1447 induced deletion resulting in the fusion of the hinge region to a DNA sequence encoding the amino acids Ala-Leu-His-Asn-His-Tyr-Thr-Glu-Lys-Ser-Leu-Ser-Leu-Ser-Pro-Gly-Lys (Sequence ID Number 31) followed in-frame by a stop codon. Replicative form DNA from a positive phage clone was digested with Hind III and Eco RI to isolate the 1.9 kb fragment comprising the $C_H1$ and hinge regions. Plasmid $p\phi5V_H$ was digested with Sst I and Hind III to isolate the 5.3 kb fragment comprising the mouse immunoglobulin heavy chain gene variable region. Plasmid pICneo was linearized by digestion with Sst I and Eco RI. The linearized pICneo was joined with the 5.3 kb Hind III-Sst I fragment and the 1.9 kb Hind III-Eco RI fragment in a three-part ligation. The resultant plasmid was designated pWKI (FIG. 10).

An SP2/0-AG14 clone stably transfected with pSDL114 and p416 was transfected with Asp 718-linearized pWKI. Transfected cells were selected by growth in medium containing methotrexate and G418. Media samples from transfected cells were assayed using the competition assay described in Example 12.C. Results from the assays showed that the transfected cells produced a PDGF β-receptor analog capable of competitively binding PDGF-BB.

EXAMPLE 13

Purification and Characterization of PDGF β-Receptor Analogs from Mammalian cells Co-transfected With pSDL113 and pSDL114

A. Purification of PDGF β-Receptor Analogs

The PDGF β-receptor analog was purified from conditioned culture media from a clone of transfected cells grown in a hollow fiber system. The media was passed over a protein-A sepharose column, and the column was washed sequentially with phosphate buffered saline, pH 7.2 (PBS; Sigma, St. Louis, Mo.) and 0.1M citrate, pH 5.0. The PDGF β-receptor analog was eluted from the protein-A column with 0.1M citrate pH 2.5 and immediately neutralized by the addition of Tris-base, pH 7.4. The eluate fractions containing PDGF β-receptor analog, as determined by silver stain, were pooled and chromatographed over an S-200 column (Pharmacia LKB Technologies, Inc., Piscataway, N.J.) equilibrated with PBS. The peak fractions from the S-200 column were pooled and concentrated on a centriprep-10 concentrator (Amicon). Glycerol (10% final volume) was added to the preparation and the sample frozen at −80° C. PDGF β-receptor analogs purified from pSDL114 +pSDL113 co-transfected cells were termed "tetrameric PDGF α-receptors".

B. Measurement of the Relative Binding Affinity of Tetrameric PDGF β-Receptor Analog by Soluble Receptor Assay Purified tetrameric PDGF β-receptor analog was compared to detergent solubilized extracts of human dermal fibroblasts for $^{125}$I-labeled PDGF-BB binding activity in a soluble receptor assay essentially as described by Hart et al. (*J. Biol. Chem.* 262: 10780–10785, 1987). Human dermal fibroblast cells were extracted at $20\times10^6$ cell equivalents per ml in TNEN extraction buffer (20 mM Tris-HCl, pH 8.0, 100 mM NaCl, 1 mM EDTA, 0.5% Nonidet P-40, 1 mM PMSF, 10% glycerol). Two hundred and fifty thousand PDGF β-receptor-subunits per cell was used to calculate the tetrameric PDGF β-receptor analog number per volume of extract. This value has been previously published by Seifert et al. (*J. Biol Chem.* 264: 8771–8778, 1989). The PDGF β-receptor analog number was determined from the protein concentration of the PDGF β-receptor analog assuming an average molecular weight of 140 kDa for each immunoglobulin-PDGF β-receptor monomer, and four monomers per tetramer. Thus, each tetrameric molecule contains four receptor molecules.

Increasing amounts of either detergent solubilized extracts of human dermal fibroblast cells or purified PDGF β-receptor analog were incubated with 1 ng of $^{125}$I-labeled PDGF-BB for one hour at 37° C. The sample was then diluted with 1 ml binding media and was added to monolayers of human dermal fibroblast cells grown in 24-well culture dishes. The samples were incubated for two hours at 4° C. The wells were washed to remove unbound, $^{125}$I-labeled PDGF-BB. On half of a milliliter of extraction buffer (PBS+1% Nonidet P-40) was added to each well followed by a 5 minute incubation. The extraction mixtures were harvested and counted in a gamma counter.

The results showed that the PDGF β-receptor analog had the same relative binding affinity as solubilized PDGF β-receptor-subunit from mammalian cells in a solution phase binding assay.

C. Determination of the Binding Affinity of the PDGF β-Receptor Analog in a Solid Phase Format The apparent dissociation constant KD(app) of the PDGF β-receptor analog was determined essentially as described by Bowen-Pope and Ross (*Methods in Enzymology* 109:

69–100, 1985), using the concentration of $^{125}$I-labeled PDGF-BB giving half-maximal specific $^{125}$I-labeled PDGF-BB binding. Saturation binding assays to determine the concentration of $^{125}$I-labeled PDGF-BB that gave half-maximal binding to immobilized PDGF β-receptor analog were conducted as follows.

Affinity purified goat anti-human IgG, H- and L-chain (Commercially available from Cappel Labs) was diluted into 0.1M Na$_2$HCO$_3$, pH 9.6 to a concentration of 2 µg/ml. One hundred microliters of the antibody solution was coated onto each well of 96-well microtiter plates for 18 hours at 4° C. The wells were washed once with ELISA C buffer (PBS+0.05% Tween-20) followed by an incubation with 175 µl/well of ELISA B buffer (PBS+1% BSA+0.05% Tween-20) to block the wells. The wells were washed once with ELISA B buffer. One hundred microliters of 12.1 ng/ml or 24.3 ng/ml of tetrameric PDGF β-receptor analog protein diluted in ELISA B was added to each well and the plates were incubated for 2 hours at 37° C. Unbound protein was removed from the wells by two washes with ELISA C. $^{125}$I-labeled PDGF-BB$_{Tyr}$ (Example 18.F.) was serially diluted into binding media (25 mM HEPES, pH 7.2, 0.25% rabbit serum albumin diluted in HAMs F-12 medium (GIBCO-BRL)), and 100 µl of the dilutions were added to the wells. The plates were incubated for two hours at room temperature. The unbound $^{125}$I-labeled PDGF-BB was removed, and the wells were washed three times with binding media. Following the last wash, 100 µl of 0.1M citrate, pH 2.5 was added to each well. After five minutes, the citrate buffer was removed, transferred to a tube and counted in a gamma counter. The counts reflect counts of $^{125}$I-labeled PDGF-BB$_{Tyr}$ bound by the receptor analog. Nonspecific binding for each concentration of $^{125}$I-labeled PDGF-BB$_{Tyr}$ was determined by a parallel assay wherein separate wells coated only with goat anti-human IgG were incubated with the $^{125}$I-labeled PDGF-BB concentrations. Nonspecific binding was determined to be 2.8% of the total input counts per well and averaged 6% of the total counts bound.

Saturation binding assay on 12.1 and 24.3 ng/ml of tetrameric PDGF β-receptor analog gave half-maximal binding at 0.8 and 0.82 ng/ml $^{125}$I-labeled PDGF-BB$_{Tyr}$, respectively. By Scatchard analysis (Scatchard, *Ann. NY Acad. Sci* 51: 660–667, 1949) these values were shown to correspond to a KD(app) of 2.7×10$^{-11}$ which agree with the published values for PDGF receptors on mammalian cells.

EXAMPLE 14

Solid Phase Ligand Binding Assay Using the PDGF β-Receptor Analog

A. Solid Phase Radioreceptor Competition Binding Assay

In a solid phase radioreceptor competition binding assay (RRA), the wells of 96-well microtiter plates were coated with 100 µl of 2 µg/ml affinity purified goat anti-human IgG (Cappel Labs) diluted in 0.1M Na$_2$HCO$_3$, pH 9.6. After an eighteen hour incubation at 4° C., the wells were washed once with ELISA C. The wells were blocked by incubation for 2 hours at 37° C. with 175 µl/well ELISA B. The wells were washed once with ELISA B then incubated for 2 hours at 37° C. with 50 ng/ml tetrameric PDGF β-receptor analog diluted in ELISA B. The unbound receptor was removed, and the test wells were incubated with increasing concentrations of serially diluted, unlabeled PDGF-BB (diluted in binding media. Following a two hour incubation at room temperature, the wells were washed three times with binding media. One hundred microliters of 5 ng/ml $^{125}$1-labeled PDGF-BB$_{Tyr}$ (Example 18.F.) was added to each well, and the plates were incubated for an additional two hours at room temperature. The wells were washed three times with binding media followed by a 5 minute incubation with 100 µl/well of 0.1M citrate, pH 2.5. The samples were harvested and counted in a gamma counter.

Radioreceptor assay (RRA) competition binding curves were generated for PDGF β-receptor analog protein plated at 48.6 ng/ml. The sensitivity of the assays is 1 ng/ml of PDGF-BB, with 8 ng/ml giving 50% inhibition in $^{125}$I-PDGF-BB binding, and a working range between 1 and 32 ng/ml of PDGF-BB. The values were similar to those obtained using monolayers of SK-5 cells in an RRA.

B. Use of Tetrameric PDGF β-Receptor Analogs As Antagonists for PDGF-Stimulated Mitogenesis.

A tetrameric PDGF β-receptor analog, purified as described in Example 13, was analyzed for the ability to neutralize PDGF-stimulated mitogenesis in mouse 3T3 cells. Increasing amounts of the purified tetrameric PDGF β-receptor analog were mixed with 5 ng of PDGF. The mixtures were then added to cultures of mouse 3T3 cells. The ability of the PDGF to stimulate a mitogenic response, as measured by the incorporation of $^3$H-thymidine, was determined essentially as described (Raines and Ross, *Methods in Enzymology* 109: 749–773, 1985, which is incorporated by reference herein). The tetrameric PDGF β-receptor analog demonstrated a dose response inhibition of PDGF-BB-stimulated $^3$H-thymidine incorporation, while having essentially no effect on PDGF-AA- and PDGF-AB-stimulated $^3$H-thymidine incorporation.

C. Binding of Tetrameric PDGF β-receptor Analog to Immobilized PDGF

A tetrameric PDGF β-receptor analog, purified as described in Example 13, was analyzed for its ability to bind to immobilized PDGF. PDGF-BB (100 ng/ml) was coated onto wells a 96-well microtiter plate, and the plates were incubated 18 hours at 4° C. followed by one wash with ELISA C buffer. The wells were incubated for 2 hours 37° C. with ELISA B buffer to block the wells. Increasing concentrations of $^{125}$I-labeled tetrameric PDGF β-receptor analog, diluted in binding media, was added to the wells for two hours at room temperature. The wells were washed four times with ELISA C buffer to remove unbound receptor analog. One hundred microliters of 1M H$_2$SO$_4$ was added to each well and the plates were incubated for five minutes at room temperature. The solution was then harvested and transferred to tubes to be counted in a gamma counter. Nonspecific binding was determined to be less than 10% of the total counts bound.

A receptor competition binding assay was developed using this assay format. The assay was carried out as described above, and simultaneous to the addition of the $^{125}$I-labeled tetrameric PDGF β-receptor analog, increasing amounts of PDGF-AA, AB or BB were added to the PDGF-BB coated wells. Under these conditions, only PDGF-BB was found to significantly block the binding of the labeled PDGF β-receptor analog to the immobilized PDGF-BB.

EXAMPLE 15

Construction and Expression of PDGFα-R Analogs in Cultured Mouse Myeloma Cells

A. Construction of an Optimized PDGFα-R cDNA

The PDGF αα-receptor coding region was optimized for expression in mammalian cells as follows. The 5' end of the cDNA was modified to include an optimized Kozak consensus translation initiation sequence (Kozak, *Nuc. Acids Res.* 12: 857–872, 1984) and Eco RI and Bam HI sites just 5' of the initiation methionine codon. Oligonucleotides ZC2181, ZC2182, ZC2183 and ZC2184 (Sequence ID Numbers 23, 24, 25 and 26, respectively; Table 1) were designed to form, when annealed, an adapter having an Eco RI adhesive end, a Bam HI restriction site, a sequence encoding a Kozak consensus sequence 5' to the initiation methionine codon, a mammalian codon optimized sequence encoding amino acids 1–42 of FIG. 11A, and an Eco RI adhesive end that destroys the Eco RI site within the PDGFα-R coding sequence. The adapter also introduced a diagnostic Cla I site 3' to the initiation methionine codon. Oligonucleotides ZC2181, ZC2182, ZC2183 and ZC2184 were kinased, annealed and ligated. Plasmid pα17B was linearized by partial digestion with Eco RI. The linearized pα17B was ligated with the ZC2181/ZC2182/ZC2183/ZC2184 oligonucleotide adapter, and the ligation mixture was transformed into E. coli. Plasmid DNA prepared from the transformants was analyzed by restriction analysis and a positive clone having the oligonucleotide adapter in the correct orientation was digested with Eco RI and Pst I to isolate the 1.6 kb fragment. This fragment was subcloned into Eco RI+Pst I-linearized M13mp19. The resultant phage clone was designated 792-8. Single-stranded 792-8 DNA was sequenced to confirm the orientation of the adapter.

A fragment encoding the ligand-binding domain of the PDGF α-receptor (PDGFα-R) was then generated as follows. Restriction sites and a splice donor sequence were introduced at the 3' end of the PDGFα-R extracellular domain by PCR amplification of the 792–8 DNA and oligonucleotides ZC2311 and ZC2392 (Sequence ID Numbers 27 and 30, Table 1). Oligonucleotide ZC2311 is a sense primer encoding nucleotides 1470 to 1489 of FIG. 11B. Oligonucleotide ZC2392 is an antisense primer that encodes nucleotides 1759 to 1776 of FIG. 11B followed by a splice donor and Xba I and Hind III restriction sites. The 792–8 DNA was amplified using manufacturer recommended (Perkin Elmer Cetus, Norwalk, Conn.) conditions and the GeneAmp™ DNA amplification reagent kit (Perkin Elmer Cetus), and blunt-ended 329 bp fragment was isolated. The blunt-end fragment was digested with Nco I and Hind III and ligated with Sma I-digested pUC18. A plasmid having an insert with the Nco I site distal to the Hind III site present in the pUC18 polylinker was designated pUC18 Sma-PCR Nco HIII #13. The Hind III site present in the insert was not regenerated upon ligation with the linearized pUC18. Plasmid pUC18 Sma-PCR Nco HIII #13 was digested with Nco I and Hind III to isolate the 355 bp PDGFα-R containing fragment encoding PDGFαR. Oligonucleotides ZC2351 and ZC2352 (Table 1; Sequence ID Numbers 28 and 29) were kinased and annealed to form an Sst I-Nco I adapter encoding an internal Eco RI site and a Kozak consensus translation initiation site. The 355 bp Nco I-Hind III fragment, the ZC2351/ZC2352 adapter and a 1273 bp Nco I fragment comprising the extracellular domain of PDGF α-R derived from 792–8 were ligated with Hind III+SstI-digested pUC18 and transformed into E. coli. Plasmid DNA was isolated from the transformants and analyzed by restriction analysis. None of the isolates contained the 1273 bp Nco I fragment. A plasmid containing the Nco I-Hind III fragment and the ZC2351/ZC2352 adapter was designated pUC18 Hin Sst A Nco #46. Plasmid pUC18 Hin Sst A Nco #46 was linearized by digestion and joined by ligation with the 1273 bp Nco I fragment comprising the extracellular domain of the PDGFβ-R from clone α18 R-19. The ligations were transformed into E. coli, and plasmid DNA was isolated from the transformants. Analysis of the plasmid DNA showed that only clones with the Nco I fragment in the wrong orientation were isolated. A clone having the Nco I fragment in the wrong orientation was digested with Nco I, religated and transformed into E. coli. Plasmid DNA was isolated from the transformants and was analyzed by restriction analysis. A plasmid having the Nco I insert in the correct orientation was digested to completion with Hind III and partially digested with Sst I to isolate the 1.6 kb fragment comprising the extracellular domain of the PDGFα-R preceded by a consensus initiation sequence (Kozak, ibid.) and followed by a splice donor site.

B. Construction of pPAB7

The DNA sequence encoding the extracellular domain of the PDGFα-R was joined to the immunoglobulin μ enhancer-promoter and to a DNA sequence encoding an immunoglobulin light chain constant region. The immunoglobulin μ enhancer-promoter was obtained from plasmid pJH1 which was derived from plasmid PICμPRE8 (Example 12.A.) by digestion with Eco RI and Sst I to isolate the 2.2 kb fragment comprising the immunoglobulin enhancer and heavy chain variable region promoter. The 2.2 kb Sst I-Eco RI fragment was ligated with Sst I+Eco RI-linearized pUC19. The resulting plasmid, designated pJH1, contained the immunoglobulin enhancer and heavy chain variable region promoter immediately 5' to the pUC19 linker sequences. Plasmid pJH1 was linearized by digestion with Sst I and Hind III and joined with the 1.6 kb partial Sst I-Hind III fragment containing the PDGFα-R extracellular domain sequences. The resulting plasmid having the immunoglobulin μ enhancer-promoter joined to the PDGFα-R extracellular domain was designated pPAB6. Plasmid pSDL112 was digested with Hind III to isolate the 1.2 kb fragment encoding the immunoglobulin light chain constant region (Cκ). The 1.2 kb Hind III fragment was ligated with Hind III-linearized pPAB6. A plasmid having the κ sequence in the correct orientation was designated pPAB7.

C. Construction of pPAB9

The partial Sst I-Hind III fragment encoding the extracellular domain of the PDGFα-R was joined to the immunoglobulin heavy chain constant region. For convenience, the internal Xba I site in plasmid pJH1 was removed by digestion with Xba I, blunt-ending with T4 DNA polymerase, and religation. A plasmid which did not contain the internal Xba I site, but retained the Xba I site in the polylinker was designated 11.28.3.6. Plasmid 11.28.3.6 was linearized by digestion with Sst I and Xba I. Plasmid pPAB6 was digested to completion with Hind III and partially digested with Sst I to isolate the 1.6 kb Sst I-Hind III fragment containing the PDGFα-R extracellular domain. Plasmid pϕ5V$_H$huC$_γ$1M-neo (Example 12.C.) was digested with Hind III and Xba I to isolate the 6.0 kb fragment encoding the immunoglobulin heavy chain constant region (huC$_γ$1M). The Sst I-Hind III-linearized 11.28.3.6, the 1.6 kb Sst I-Hind III PDGFα-R fragment and the 6.0 kb Hind III-Xba I huC$_γ$1M fragment were ligated to form plasmid pPAB9.

D. Expression of pPAB9 in Mammalian Cells

Bgl II-linearized pPAB7 and Pvu I-linearized pPAB9 were cotransfected with Pvu I-linearized p416 into SP2/0-Ag14 cells by electroporation. Transfected cells were initially selected in growth medium containing 50 nM methotrexate and were subsequently amplified in a growth medium containing 100 μM methotrexate. Media from drug resistant clones were tested for the presence of secreted PDGF α-receptor analogs by enzyme-linked immunosorbant assay (ELISA). Ninety-six well assay plates were prepared by incubating 100 μl of 1 μg/ml monoclonal antibody 292.1.8 which is specific for the PDGF α-receptor diluted in phosphate buffered saline (PBS; Sigma] overnight at 4° C. Excess antibody was removed by three washes with 0.5% Tween 20 in PBS. One hundred microliters of spent media was added to each well, and the plates were incubated for one hour at 4° C. Unbound proteins were removed by eight washes with 0.5% Tween 20 in PBS. One hundred microliters of peroxidase-conjugated goat anti-human IgG heavy chain antibody (diluted 1:1000 in a solution containing 5% chicken serum (GIBCO-BRL)+0.5% Tween 20 in PBS) was added to each well, and the plates were incubated for one hour at 4° C. One hundred microliters of chromophore (100 µl ABTS [2,2'-Azinobis(3-ethylbenz-thiazoline sulfonic acid] diammonium salt; Sigma]+1 µl 30% $H_2O_2$ +12.5 ml citrate/phosphate buffer [9.04 g/l citric acid, 10.16 g/l $Na_2HPO_4$]) was added to each well, and the wells were incubated for 30 minutes at room temperature. The samples were measured at 405 nm. The results of the assay showed that the PDGF α-receptor analogs secreted by the transfectants contained an immunoglobulin heavy chain.

Analysis of spent media from transfected cells by Northern analysis, Western analysis and by radioimmunoprecipitation showed that the transfectants did not express a PDGF α-receptor analog from the pPAB7 construction. Transfectants were subsequently treated as containing only pPAB9.

Drug resistant clones were also tested for the presence of secreted PDGF α-receptor analogs by immunoprecipitation. For each clone, approximately one million drug resistant transfectants were grown in DMEM lacking cysteine+2% calf serum for 18 hours at 37° C. in the presence of 50 µCi $^{35}$S-cysteine. The spent media was harvested from the labeled cells and 250 Al of medium from each clone was assayed for binding to the anti-PDGF α-receptor antibody 292.18. Monoclonal antibody 292.18 diluted in PBS was added to each sample to a final concentration of 2.5 µg per 250 Al spent media. Five microliters of rabbit anti-mouse Ig diluted in PBS was added to each sample, and the immunocomplexes were precipitated by the addition of 50 µl 10% fixed Staph A (weight/volume in PBS). The immunocomplexes were analyzed on 8% SDS-polyacrylamide gels followed by autoradiography overnight at -70 ° C. The results of the immunoprecipitation showed that the PDGF α-receptor analog secreted by the transfectants was bound by the anti-PDGF α-receptor antibody. The combined results of the ELISA and immunoprecipitation assays showed that the PDGF α-receptor analog secreted by the transfectants contained both the PDGF α-receptor ligand-binding domain and the human heavy chain.

Spent medium from drug-resistant clones were tested for their ability to bind PDGF in a competition binding assay essentially as described in Example 12.C. The results of the assay showed that the transfectants secreted a PDGF α-receptor analog capable of binding PDGF-AA. A clone containing the pPAB9 was designated 3.17.1.57.

E. Co-expression of pPAB7 and pPAB9 in Mammalian Cells

Bgl II-linearized pPAB7 and Bam HI-linearized pICneo were cotransfected into clone 3.17.1.57, and transfected cells were selected in the presence of neomycin. Media from drug resistant cells were assayed for the presence of immunoglobulin heavy chain, immunoglobulin light chain and the PDGF α-receptor ligand-binding domain by ELISA essentially as described above. Briefly, ninety-six well assay plates were prepared by incubating 100 µl of 1 µg/ml goat anti-human IgG Fc antibody (Sigma) or 100 µl of 1 µg/ml 292.18 overnight at 4° C. Excess antibody was removed by three washes with 0.5% Tween 20 in PBS. One hundred microliters of spent media was added to each well of each plate, and the plates were incubated for one hour at 4° C. Unbound proteins were removed by eight washes with 0.5% Tween 20 in PBS. One hundred microliters of peroxidase-conjugated goat anti-human IgG antibody (diluted 1:1000 in a solution containing 5% chicken serum (GIBCO-BRL)+ 0.5% Tween 20 in PBS) was added to each well of the plate coated with the anti-Fc antibody, and 100 µl of peroxidase-conjugated goat anti human kappa antibody (diluted 1:1000 in a solution containing 5% chicken serum (GIBCO-BRL) +0.5% Tween 20 in PBS) was added to each well of the plate coated with 292.18. The plates were incubated for one hour at 4° C. One hundred microliters of chromophore (100 µl ABTS [2,2'-Azinobis(3-ethylbenz-thiazoline sulfonic acid) diammonium salt; Sigma]+1 µl 30% $H_2O_2$+12.5 ml citrate/ phosphate buffer [9.04 g/l citric acid, 10.16 g/l $Na_2HPO_4$]) was added to each well of each plate, and the plates were incubated to 30 minutes at room temperature. The samples were measured at 405 nm, the wavelength giving maximal absorbance of the chromogenic substrate, to identify clones having absorbances higher than background indicating the presence of immunoglobulin heavy chain. Clones that gave positive results in both ELISA assays (showing that the clones produced proteins containing heavy chain regions, light chain constant regions and the PDGF α-receptor ligand-binding region) were selected for further characterization.

Drug resistant clones that were positive for both ELISA assays were subsequently tested for the presence of secreted PDGF α-receptor analogs by immunoprecipitation. For each positive clone, approximately one million drug resistant transfectants were grown in DMEM lacking cysteine+2% calf serum for 18 hours at 37° C. in the presence of 50 µgCI $^{35}$S-cysteine. The spent media was harvested from the labeled cells and 250 µl of medium from each clone was assayed for binding to monoclonal antibody 292.18. Monoclonal antibody 292.18 diluted in PBS was added to each sample to a final concentration of 2.5 µg. Five microliters of rabbit anti-mouse Ig diluted in PBS was added to each sample and the immunocomplexes were precipitated by the addition of 50 µl 10% fixed Staph A (weight/volume in PBS). The immunocomplexes were analyzed on 8% SDS-polyacrylamide gels followed by autoradiography overnight at −70° C. The results of the immunoprecipitation showed that the PDGF α-receptor analog secreted by the transfectants was bound by the anti-PDGF α-receptor antibody. The combined results of the ELISA and immunoprecipitation assays showed that the PDGF α-receptor analog secreted by the transfectants contained the PDGF α-receptor ligand-binding domain, the human heavy chain and the human light chain constant region. A clone that secreted a PDGF α-receptor analog that was positive for both the above-described ELISA assays and the immunoprecipitation assay was designated 5.6.2.1.

EXAMPLE 16

Purification and Characterization of PDGF α-Receptor Analogs

A. Purification of PDGF α-Receptor Analogs From Clone 3.17.1.57

The PDGF a-Receptor analog was purified from the conditioned culture media of clone 3.17.1.57 by cycling cell-conditioned medium over an immunoaffinity column composed of monoclonal antibody 292.18 bound to a CNBr-activated Sepharose 4B resin, which is specific for the PDGF α-receptor. The column was washed with PBA, then eluted with 0.1M citrate, pH 3.0. The peak column fractions containing the α-receptor were pooled, neutralized to pH 7.2 by the addition of 2M Tris, pH 7.4, then passed over a protein-A Sepharose column. This column was washed sequentially with PBS, then with 0.1M citrate, pH 5.0. The PDGF α-receptor analog was then eluted with 0.1M citrate, pH 3.0. The peak eluate fractions were pooled, and glycerol was added to a final concentration of 10%. The sample was concentrated on a centriprep 10 concentrator (Ainicon). The PDGF α-receptor analog purified from clone 3.17.1.57 was termed a "dimeric PDGF α-receptor analog".

B. Purification of PDGF α-Receptor Analogs From Clone 5.6.2.1

The PDGF α-receptor analog was purified from the conditioned culture media of clone 5.6.2.1 by cycling cell-conditioned medium over the immunoaffinity column described above. The column was washed with PBS then eluted with 0.1M citrate, pH 3.0. The peak column fractions containing the α-receptor were pooled, neutralized to pH 7.2 by the addition of 2M Tris (what pH 7.4), then passed over a protein-A sepharose column. This column was washed sequentially with PBS then with 0.1M citrate, pH 5.0. The PDGF α-receptor analog was then eluted with 0.1M citrate, pH 3.0. The peak eluate fractions were pooled and glycerol was added to a final concentration of 10%. The sample was concentrated on a centriprep 10 concentrator. The PDGF α-receptor analogs purified from clone 5.6.2.1 was termed a "tetrameric PDGF α-receptor analog".

EXAMPLE 17

A. Use of the PDGF α-receptor Analogs in Ligand Binding Studies

Purified tetrameric PDGF α-receptor analog and purified dimeric PDGF α-receptor analog were compared to monolayers of a control cell line of canine kidney epithelial cells, which do not naturally express the PDGF α-receptor, transfected with the human PDGF α-receptor cDNA for ligand binding activity. The dissociation constant (Kd) of the receptor preparations was determined by saturation binding and subsequent Scatchard analysis.

Ligand binding of the purified PDGF α-receptor analogs was determined using a solid phase binding assay. Affinity-purified goat anti-human IgG was diluted to a concentration of 2 μg/ml in 0.1M $Na_2HCO_3$, pH 9.6 and 100 μl/well of the solution was used to coat 96-well microtiter plates for 18 hours at 4° C. Excess antibody was removed from the wells with one wash with ELISA C buffer (PBS, 0.05% Tween-20). The plates were incubated with 175 μl/well of ELISA B buffer (PBS, 1% BSA, 0.05% Tween-20) to block the wells, followed by two washes with ELISA C buffer. One hundred microliters of 50 ng/ml PDGF α-receptor analog (dimeric or tetrameric) diluted in ELISA buffer B was added to each well and the plates were incubated over night at 4° C. Unbound protein was removed from the wells with two washes with ELISA buffer B. $^{125}$I-labeled PDGF-AA was serially diluted in binding media (Hams F-12, 25 mM HEPES pH 7.2, 0.25% rabbit serum albumin), and 100 μl of each dilution was added to the wells. The samples were incubated for two hours at room temperature. Unbound $^{125}$I-labeled PDGF-AA was removed with three washes with binding media. One hundred microliters of 0.1M citrate, pH 2.5 was added to each well, and the plates were incubated for five minutes. After the incubation, the citrate buffer was removed and transferred to a tube for counting in a gamma counter. Nonspecific binding for each concentration of $^{125}$I-labeled PDGF-AA was determined by a parallel assay wherein separate wells coated only with goat anti-human IgG were incubated with the $^{125}$I-labeled PDGF-AA samples.

A saturation binding assay was performed on alpha T-7 cells transfected with the PDGF α-receptor. The cells were grown to confluency in 24-well culture plates. The cells were washed one time with binding media. Iodinated PDGF-AA was serially diluted in binding media. One milliliter of each dilution was added to the wells, and the plates were incubated for 3 hours at 4° C. Unbound $^{125}$I-labeled PDGF-AA was removed and the cells were washed three times with binding media. PBS containing 1% Triton X-100 was added to the cells for 5 minutes. The extracts were harvested and counted in a gamma counter. Nonspecific binding was determined at a single concentration of $^{125}$I-labeled PDGF-AA using a 500-fold excess PDGF-BB.

The dissociation constants determined by Scatchard analysis (ibid.) of the saturation binding assays for the tetrameric PDGF α-receptor analog, dimeric PDGF α-receptor analog and the control cells (Table 5).

TABLE 5

Dissociation Constants for the Tetrameric PDGF α-Receptor, the Dimeric PDGF α-receptor and control cells Transfected with the PDGF α-receptor

| Receptor | kD |
| --- | --- |
| Tetrameric PDGF α-receptor analog | $1.6 \times 10^{-11}$ |
| Dimeric PDGF α-receptor analog | $8.51 \times 10^{-11}$ |
| Control cells[PDGF α-receptor] | $3.7 \times 10^{-11}$ |

A solid-phase competition binding assay was established using the tetrameric PDGF α-receptor analog. Ninety six-well microtiter plates were coated with goat anti-human IgG (2 μg/ml), the wells blocked with ELISA B buffer, 50 ng/ml of purified tetrameric PDGF α-receptor analog diluted in binding media was added, and the plates were incubated two hours at room temperature. Unbound receptor was removed and the wells were washed with binding media. The plates were incubated for two hours at room temperature with increasing concentrations of either PDGF-AA or PDGF-BB diluted in binding media. The wells were washed, then incubated for two hours at room temperature with 3 ng/ml $^{125}$I-labeled PDGF-AA diluted in binding media. Unbound labeled PDGF-AA was removed, the wells were subsequently washed with binding media, and the bound, labeled PDGF-AA was harvested by the addition of 0.1M citrate, pH 2.5, as described for the saturation binding studies. PDGF-AB, PDGF-AA and PDGF-BB were found to compete for receptor binding with $^{125}$I-PDGF-AA.

B. Use of Tetrameric PDGF α-Receptor Analogs as Antagonists for PDGF-Stimulated Mitogenesis.

A tetrameric PDGF α-receptor analog, purified as described in Example 16.B., was analyzed for the ability to neutralize PDGF-stimulated mitogenesis in mouse 3T3 cells. Increasing amounts of the purified tetrameric PDGF α-receptor analog were mixed with PDGF-AA, -AB or -BB ranging .6 to 5 ng. The mixtures were then added to cultures of confluent mouse 3T3 cells. The ability of the PDGF to stimulate a mitogenic response, as measured by the incorporation of $^3$H-thymidine, was determined essentially as described (Raines and Ross, *Methods in Enzymology* 109: 749–773, 1985, which is incorporated by reference herein). The tetrameric PDGF α-receptor analog demonstrated a dose response inhibition of PDGF-stimulated $^3$H-thymidine incorporation for all three isoforms of PDGF.

C. Inverse Ligand-Receptor Radioreceptor Assay

An inverse ligand-receptor radioreceptor assay was designed to screen for the presence of PDGF-BB, PDGF-BB binding proteins, PDGF-BB related molecules, and PDGF-β receptor antagonists in test samples. PDGF-BB (100 ng/ml) was coated onto the walls of 96-well microtiter plates, and the plates were incubated at 4° C. for 16 hours. The wells were washed once with ELISA C buffer and then incubated with ELISA B buffer to block the nonspecific binding sites. To the wells were added 50 µl of either PDGF standard or a test sample and 50 µl of $^{125}$I-labeled tetrameric PDGF β-receptor analog. The samples were incubated for one hour at room temperature. The wells were washed once with ELISA C buffer, and 0.1M citrate, pH 2.5 containing 1% NP-40 was added to each well to disrupt the ligand-receptor analog bond and elute the bound receptor analog. The acid wash was collected and counted in a gamma counter. The presence of PDGF or a molecule which mimics PDGF or otherwise interferes with the binding of the well-bound PDGF-BB with its receptor will cause a decrease in the binding of the radiolabeled tetrameric PDGF β-receptor. Using this assay, PDGF-BB was found to inhibit receptor binding while PDGF-AA and PDGF-AB caused no significant decrease in receptor binding.

EXAMPLE 18

Assay Methods ps A. Preparation of Nitrocellulose Filters for Colony Assay

Colonies of transformants were tested for secretion of PDGF β-receptor analogs by first growing the cells on nitrocellulose filters that had been laid on top of solid growth medium. Nitrocellulose filters (Schleicher & Schuell, Keene, N.H.) were placed on top of solid growth medium and were allowed to be completely wetted. Test colonies were patched onto the wetted filters and were grown at 30° C. for approximately 40 hours. The filters were then removed from the solid medium, and the cells were removed by four successive rinses with Western Transfer Buffer (Table 4). The nitrocellulose filters were soaked in Western Buffer A (Table 4) for one hour at room temperature on a shaking platform with two changes of buffer. Secreted PDGFβ-R analogs were visualized on the filters described below.

B. Preparation of Protein Blot Filters

A nitrocellulose filter was soaked in Western Buffer A (Table 4) without the gelatin and placed in a Minifold (Schleicher & Schuell, Keene, N.H.). Five milliliters of culture supernatant was added without dilution to the Minifold wells, and the liquid was allowed to pass through the nitrocellulose filter by gravity. The nitrocellulose filter was removed from the minifold and was soaked in Western Buffer A (Table 3) for one hour on a shaking platform at room temperature. The buffer was changed three times during the hour incubation.

C. Preparation of Western Blot Filters The transformants were analyzed by Western blot, essentially as described by Towbin et al. (*Proc. Natl. Acad. Sci. USA* 76: 4350–4354, 1979) and Gordon et al. (U.S. Pat. No. 4,452,901). Culture supernatants from appropriately grown transformants were diluted with three volumes of 95% ethanol. The ethanol mixtures were incubated overnight at −70° C. The precipitates were spun out of solution by centrifugation in an SS-24 rotor at 18,000 rpm for 20 minutes. The supernatants were discarded and the precipitate pellets were resuspended in 200 µl of dH$_2$O. Two hundred microliters of 2xloading buffer (Table 4) was added to each sample, and the samples were incubated in a boiling water bath for 5 minutes.

The samples were electrophoresed in a 15% sodium dodecylsulfate polyacrylamide gel under non-reducing conditions. The proteins were electrophoretically transferred to nitrocellulose paper using conditions described by Towbin et al. (ibid.). The nitrocellulose filters were then incubated in Western Buffer A (Table 4) for 75 minutes at room temperature on a platform rocker.

D. Processing the Filters for Visualization with Antibody

Filters prepared as described above were screened for proteins recognized by the binding of a PDGF β-receptor specific monoclonal antibody, designated PR7212. The filters were removed from the Western Buffer A (Table 4) and placed in sealed plastic bags containing a 10 ml solution comprising 10 µg/ml PR7212 monoclonal antibody diluted in Western Buffer A. The filters were incubated on a rocking platform overnight at 4° C. or for one hour at room temperature. Excess antibody was removed with three 15-minute washes with Western Buffer A on a shaking platform at room temperature.

Ten microliters biotin-conjugated horse anti-mouse antibody (Vector Laboratories, Burlingame, Calif.) in 20 ml Western Buffer A was added to the filters. The filters were re-incubated for one hour at room temperature on a platform shaker, and unbound conjugated antibody was removed with three fifteen-minute washes with Western Buffer A.

The filters were pre-incubated for one hour at room temperature with a solution comprising 50 µl Vectastain Reagent A (Vector Laboratories) in 10 ml of Western Buffer A that had been allowed to incubate at room temperature for 30 minutes before use. The filters were washed with one quick wash with distilled water followed by three 15-minute washes with Western Buffer B (Table 4) at room temperature. The Western Buffer B washes were followed by one wash with distilled water.

During the preceding wash step, the substrate reagent was prepared. Sixty mg of horseradish peroxidase reagent (Bio-Rad, Richmond, Calif.) was dissolved in 20 ml HPLC grade methanol. Ninety milliliters of distilled water was added to the dissolved peroxidase followed by 2.5 ml 2M Tris, pH 7.4 and 3.8 ml 4M NaCl. One hundred microliters of 30% H$_2$O$_2$ was added just before use. The washed filters were incubated with 75 ml of substrate and incubated at room temperature for 10 minutes with vigorous shaking. After the 10 minute incubation, the buffer was changed, and the filters were incubated for an additional 10 minutes. The filters were then washed in distilled water for one hour at room temperature. Positives were scored as those samples which exhibited coloration.

E. Processing the Filters For Visualization with an Anti-Substance P Antibody

Filters prepared as described above were probed with an anti-substance P antibody. The filters were removed from the Western Buffer A and rinsed with Western transfer buffer, followed by a 5-minute wash in phosphate buffered saline (PBS, Sigma, St. Louis, Mo.). The filters were incubated with a 10 ml solution containing 0.5M 1-ethyl-3–3-dimethylamino propyl carbodiimide (Sigma) in 1.0M NH$_4$Cl for 40 minutes at room temperature. After incubation, the filters were washed three times, for 5 minutes per wash, in PBS. The filters were blocked with 2% powdered milk diluted in PBS.

The filters were then incubated with a rat anti-substance P monoclonal antibody (Accurate Chemical & Scientific Corp., Westbury, N.Y.). Ten microliters of the antibody was diluted in 10 ml of antibody solution (PBS containing 20% fetal calf serum and 0.5% Tween-20). The filters were incubated at room temperature for 1 hour. Unbound antibody was removed with four 5-minute washes with PBS.

The filters were then incubated with a biotin-conjugated rabbit anti-rat peroxidase antibody (Cappel Laboratories, Melvern, Pa.). The conjugated antibody was diluted 1:1000 in 10 ml of antibody solution for 2 hours at room temperature. Excess conjugated antibody was removed with four 5-minute washes with PBS.

The filters were pre-incubated for 30 minutes at room temperature with a solution containing 50 μl Vectastain Reagent A (Vector Laboratories) and 50 μl Vectastain Reagent B (Vector Laboratories) in 10 ml of antibody solution that had been allowed to incubate for 30 minutes before use. Excess Vectastain reagents were removed by four 5-minute washes with PBS.

During the preceding wash step, the substrate reagent was prepared. Sixty milligrams of horseradish peroxidase reagent (Bio-Rad Laboratories, Richmond, Calif.) was dissolved in 25 ml of HPLC grade methanol. Approximately 100 ml of PBS and 200 μl $H_2O_2$ were added just before use. The filters were incubated with the substrate reagent for 10 to 20 minutes. The substrate was removed by a vigorous washing distilled water.

F. Iodination of PDGF-BB.

A PDGF-BB mutant molecule having a tyrosine replacing the phenylalanine at position 23 (PDGF-BB$_{Tyr}$) was iodinated and subsequently purified, using a purification method which produces 125I-labeled PDGF-BB with a higher specific activity than primary-labeled material and which was found to substantially decrease the nonspecific binding component. The PDGF-BB$_{Tyr}$ was labeled using the Iodobead method (Pierce Chemical). The labeled protein was gel filtered over a C-25 desalting column (Pharmacia LKB Technologies) equilibrated with 10 mM acetic acid, 0.25% gelatin and 100 mM NaCl. The peak fractions were pooled and pH adjusted to 7.2 by the addition of Tris-base. The labeled mixture was chromatographed over an affinity column composed of PDGF β-receptor analog protein coupled to CnBr-activated Sepharose (Pharmacia LKB Technologies, Inc.). The column was washed with phosphate buffered saline and eluted with 0.1M citrate, pH 2.5 containing 0.25% gelatin. The peak eluate fractions were pooled and assayed by ELISA to determine the PDGF-BB concentration.

Although the foregoing invention has been described in some detail by way of illustration and example for purposes of clarity of understanding, it will be evident that certain changes and modifications may be practiced within the scope of the appended claims.

We claim:

1. A method for producing a secreted active dimerized polypeptide fusion, comprising:

introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring dimerization for biological activity joined to a dimerizing protein heterologous to said non-immunoglobulin polypeptide;

growing said host cell in an appropriate growth medium under physiological conditions to allow the secretion of a dimerized polypeptide fusion encoded by said DNA sequence; and isolating said dimerized polypeptide fusion from said host cell.

2. The method of claim 1 wherein the dimerized polypeptide fusion is a homodimer.

3. The method of claim 1 wherein the dimerizing protein comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

4. The method of claim 1 wherein the dimerizing protein comprises an immunoglobulin light chain constant region.

5. The method of claim 1 wherein the dimerizing protein comprises an immunoglobulin heavy chain constant region.

6. The method of claim 5 wherein the immunoglobulin heavy chain constant region is joined to an immunoglobulin hinge region.

7. The method of claim 5 wherein the immunoglobulin heavy chain constant region is joined to an immunoglobulin variable region.

8. The method of claim 5 wherein the immunoglobulin variable region is selected from the group consisting of $V_H$, Vκ, and Vλ.

9. A method for producing a secreted, biologically active dimerized polypeptide fusion, comprising:

introducing into a eukaryotic host cell a first DNA construct comprising a transcriptional promoter operatively linked to a first secretory signal sequence followed downstream by and in proper reading frame with a first DNA sequence encoding a non-immunoglobulin polypeptide requiring dimerization for biological activity joined to an immunoglobulin light chain constant region;

introducing into said host cell a second DNA construct comprising a transcriptional promoter operatively linked to a second secretory signal sequence followed downstream by and in proper reading frame with a second DNA sequence encoding an immunoglobulin heavy chain constant region domain selected from the group consisting of $C_H1$, $C_H2$, $C_H3$, and $C_H4$, and optionally encoding an immunoglobulin hinge or variable region joined in proper reading frame to said immunoglobulin heavy chain constant region;

growing said host cell in an appropriate growth medium under physiological conditions to allow the secretion of a biologically active dimerized polypeptide fusion encoded by said first and second DNA sequences; and isolating said biologically active dimerized polypeptide fusion from said host cell.

10. The method of claim 9 wherein said second DNA sequence further encodes an immunoglobulin hinge region and wherein said hinge region is joined to said immunoglobulin heavy chain constant region.

11. The method of claim 9 wherein said second DNA sequence further encodes an immunoglobulin variable region and wherein said variable region is joined upstream of and in proper reading frame with said immunoglobulin heavy chain constant region domain.

12. The method of claim 9 wherein said host cell is a fungal cell or a cultured mammalian cell.

13. The method of claim 9 wherein said host cell is a cultured rodent myeloma cell line.

14. The method of claim 9 wherein said non-immunoglobulin polypeptide requiring dimerization for biological activity is selected from the group consisting of a polypeptide comprising the amino acid sequence of FIGS. 1A–1D (Sequence ID Numbers 1 and 2) from isoleucine, number 29, to lysine, number 531, a polypeptide comprising the amino acid sequence of FOGS. 1A–1D (Sequence ID Numbers 1 and 2) from isoleucine, number 29, to methionine, number 441, and a polypeptide comprising the amino acid sequence of FIGS. 11A–11 D (Sequence ID Numbers 35 and 36) from glutamine, number 24 to glutamic acid, number 524.

15. A method for producing a secreted, biologically active dimerized polypeptide fusion, comprising:

introducing into a eukaryotic host cell a first DNA construct comprising a transcriptional promoter operatively linked to a first secretory signal sequence followed downstream by and in proper reading frame with a first DNA sequence encoding a non-immunoglobulin polypeptide requiring dimerization for biological activity joined to an immunoglobulin heavy chain constant region domain selected from the group consisting of $C_H1$, $C_H2$, $C_H3$, and $C_H4$, and optionally encoding an immunoglobulin hinge or variable region joined in proper reading frame to said immunoglobulin heavy chain constant region;

introducing into said host cell a second DNA construct comprising a transcriptional promoter operatively linked to a second secretory signal sequence followed downstream by and in proper reading frame with a second DNA sequence encoding an immunoglobulin light chain constant region, and optionally encoding immunoglobulin variable region joined in proper reading frame to said immunoglobulin heavy chain constant region;

growing said host cell in an appropriate growth medium under physiological conditions to allow the secretion of a biologically active dimerized polypeptide fusion encoded by said first and second DNA sequences; and isolating said biologically active dimerized polypeptide fusion from said host cell.

16. The method of claim 15 wherein said first DNA sequence further encodes an immunoglobulin hinge region and wherein said hinge region is joined to said immunoglobulin constant region.

17. The method of claim 15 wherein said second DNA sequence further encodes an immunoglobulin variable region and wherein said variable region is joined upstream of and in proper reading frame with said immunoglobulin light chain constant region domain.

18. The method of claim 15 wherein said host cell is a fungal cell or a cultured mammalian cell.

19. The method of claim 15 wherein said host cell is a cultured rodent myeloma cell line.

20. The method of claim 15 wherein said non-immunoglobulin polypeptide requiring dimerization for biological activity is selected from the group consisting of a polypeptide comprising the amino acid sequence of FIGS. 1A–1D (Sequence ID Numbers 1 and 2) from isoleucine, number 29, to lysine, number 531 a polypeptide comprising the amino acid sequence of FIGS. 1A–1D (Sequence ID Numbers 1 and 2) from isoleucine, number 29, to methionine, number 441, and a polypeptide comprising the amino acid sequence of FIGS. 11A–11D (Sequence ID Numbers 35 and 36) from glutamine, number 24 to glutamic acid, number 524.

21. A method for producing a secreted receptor analog, comprising:

introducing into a eukaryotic host cell a DNA construct comprising a transcriptional promoter operatively linked to at least one secretory signal sequence followed downstream by and in proper reading frame with a DNA sequence encoding a ligand-binding domain of a receptor requiring dimerization for biological activity joined to a dimerizing protein heterologous to said ligand-binding domain, and optionally an immunoglobulin hinge or variable region to said dimerizing protein;

growing said host cell in an appropriate growth medium under physiological conditions to allow the secretion of a receptor analog encoded by said DNA sequence; and isolating said receptor analog from said host cell.

22. The method of claim 21 wherein the dimerizing protein comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

23. The method of claim 21 wherein the dimerizing protein comprises an immunoglobulin light chain constant region.

24. The method of claim 21 wherein the dimerizing protein comprises an immunoglobulin heavy chain constant region.

25. The method of claim 24 wherein the immunoglobulin heavy chain constant region is joined to an immunoglobulin hinge region.

26. The method of claim 24 wherein the immunoglobulin heavy chain constant region is joined to an immunoglobulin variable region.

27. The method of claim 26 wherein the immunoglobulin variable region is selected from the group consisting of $V_H$, Vκ, and Vλ.

28. A method for producing a secreted PDGF receptor analog, comprising:

introducing into a cultured rodent myeloma cell a first DNA construct comprising a mouse $V_H$ promoter operatively linked to a PDGF receptor signal sequence followed downstream of and in proper reading frame with a DNA sequence encoding the amino acid sequence of FIGS. 11A–11D (Sequence ID Numbers 35 and 36) from glutamine, number 24 to glutamic acid, number 524, joined to an immunoglobulin heavy chain constant region domain selected from the group consisting of $C_H1$, $C_H2$, $C_H3$, and $C_H4$ joined to an immunoglobulin hinge region;

introducing into said cultured rodent myeloma cell a second DNA construct comprising a mouse $V_κ$ promoter operatively linked to a PDGF receptor signal sequence followed downstream of and in proper reading frame with a DNA sequence encoding the amino acid sequence of FIGS. 1A–1D (Sequence ID Numbers 1 and 2) from isoleucine number 29, to lysine, number 531, joined to an immunoglobulin light chain constant region;

growing said cultured rodent myeloma cell in an appropriate growth medium under physiological conditions to allow the secretion of a PDGF receptor analog encoded by said first and second DNA sequences; and isolating said PDGF receptor analog from said cultured myeloma cell.

29. A method for producing a secreted active multimerized polypeptide fusion, comprising:

introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring multimerization for biological activity joined to a multimerizing protein selected from the group consisting of: an immunoglobulin heavy chain or light chain constant region, and optionally encoding an immunoglobulin hinge or variable region joined to said multimerizing protein;

growing said host cell in an appropriate growth medium under physiological conditions to allow the secretion of a multimerized polypeptide fusion encoded by said DNA sequence; and isolating said multimerized polypeptide fusion from said host cell.

30. The method of claim 29 wherein said multimerized polypeptide fusion is a tetramer comprising four polypeptide fusions each having a non-immunoglobulin polypeptide joined to a multimerizing protein.

31. The method of claim 29 wherein the multimerizing protein comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

32. The method of claim 29 wherein the multimerizing protein comprises an immunoglobulin light chain constant region.

33. The method of claim 29 wherein the multimerizing protein comprises an immunoglobulin heavy chain constant region.

34. The method of claim 33 wherein the immunoglobulin heavy chain constant region is joined to an immunoglobulin hinge region.

35. The method of claim 33 wherein the immunoglobulin heavy chain constant region is joined to an immunoglobulin variable region.

36. The method of claim 35 wherein the immunoglobulin variable region is selected from the group consisting of $V_H$, Vκ, and Vλ.

37. A method for producing a secreted active heteromultimeric polypeptide fusion, comprising:

introducing into a eukaryotic host cell a first DNA construct comprising a transcriptional promoter operatively linked to a secretory signal sequence followed downstream by and in proper reading frame with a first DNA sequence encoding a first polypeptide fusion comprising a first non-immunoglobulin polypeptide joined to a first multimerizing protein selected from the group consisting of: an immunoglobulin heavy chain or light chain constant region, and optionally encoding an immunoglobulin hinge or variable region joined to said first multimerizing protein, and a second DNA construct comprising a transcriptional promoter operatively linked to a secretory signal sequence followed downstream by and in proper reading frame with a second DNA sequence encoding a second polypeptide fusion comprising a second non-immunoglobulin polypeptide joined to a second multimerizing protein selected from the group consisting of: an immunoglobulin heavy chain or light chain constant region, and optionally encoding an immunoglobulin hinge or variable region joined to said second multimerizing protein;

growing said host cell in an appropriate growth medium under physiological conditions to allow secretion of said heteromultimeric polypeptide fusion encoded by said DNA sequences; and isolating said heteromultimeric polypeptide fusion from said host cell.

38. The method of claim 37 wherein the first and second non-immunoglobulin polypeptides each comprise an amino acid sequence selected from the group consisting of (A) the amino acid sequence of FIGS. 1A–1D (Sequence ID Numbers 1 and 2), and (B) the amino acid sequence of FIGS. 11A–11D (Sequence ID Numbers 35 and 36).

39. The method of claim 37 wherein one of said multimerizing proteins comprises an immunoglobulin heavy chain constant region domain selected from the group consisting of $C_H1$, $C_H2$, $C_H3$, and $C_H4$ of a γ, α, ε, μ, or δ class immunoglobulin heavy chain.

40. The method of claim 37 wherein the first multimerizing protein is different from the second multimerizing protein.

41. The method of claim 40 wherein the first and second non-immunoglobulin polypeptides are the same.

42. The method of claim 37 wherein said multimerized polypeptide fusion comprises a first polypeptide fusion comprising a first receptor or receptor ligand binding domain requiring multimerization for activity joined to a first immunoglobulin constant region and a second polypeptide fusion comprising a second receptor or receptor ligand binding domain requiring multimerization for activity joined to a second immunoglobulin constant region.

43. The method of claim 37 wherein said heteromultimeric polypeptide fusion is a heterotetramer comprising four polypeptide fusions each having a non-immunoglobulin polypeptide joined to a multimerizing protein.

44. The method of claim 37 wherein said heteromultimeric polypeptide fusion comprises a first polypeptide fusion having a first non-immunoglobulin polypeptide joined to a first immunoglobulin constant region and a second polypeptide fusion having a second non-immunoglobulin polypeptide fused to a second immunoglobulin constant region different from the first immunoglobulin constant region.

45. The method of claim 44 wherein the first multimerizing protein comprises an immunoglobulin heavy chain constant region and the second multimerizing protein comprises an immunoglobulin light chain constant region.

46. The method of claim 37 wherein the first and second multimerizing proteins each comprise an immunoglobulin heavy chain constant region or an immunoglobulin light chain constant region.

47. The method of claim 46 wherein one of said multimerizing proteins comprises an immunoglobulin heavy chain constant region joined to an immunoglobulin hinge region.

48. The method of claim 46 wherein one of said multimerizing proteins comprises an immunoglobulin heavy chain constant region joined to an immunoglobulin variable region.

49. The method of claim 48 wherein the immunoglobulin variable region is selected from the group consisting of $V_H$, Vκ, and Vλ.

* * * * *

UNITED STATES PATENT AND TRADEMARK OFFICE
CERTIFICATE OF CORRECTION

PATENT NO. : 5,843,725
DATED : December 1, 1998
INVENTOR(S) : Andrzej Z. Sledziewski et al.

Page 1 of 1

It is certified that error appears in the above-identified patent and that said Letters Patent is hereby corrected as shown below:

<u>Column 103, claim 15,</u>
Line 7, the term "or variable region" should be deleted.
Lines 7-8, the term "in proper reading frame" should be deleted.
Line 17, the term "heavy" should read -- light --.

Signed and Sealed this

First Day of January, 2002

Attest:

Attesting Officer

JAMES E. ROGAN
*Director of the United States Patent and Trademark Office*

US005843725C1

(12) EX PARTE REEXAMINATION CERTIFICATE (5480th)
United States Patent
Sledziewski et al.

(10) Number: US 5,843,725 C1
(45) Certificate Issued: Aug. 29, 2006

(54) METHODS OF PRODUCING SECRETED RECEPTOR ANALOGS AND BIOLOGICALLY ACTIVE DIMERIZED POLYPEPTIDE FUSIONS

(75) Inventors: Andrzej Z. Sledziewski, Seattle, WA (US); Lillian Anne Bell, Seattle, WA (US); Wayne R. Kindsvogel, Seattle, WA (US)

(73) Assignee: Zymogenetics, Inc., Seattle, WA (US)

Reexamination Request:
No. 90/006,970, Mar. 16, 2004

Reexamination Certificate for:
Patent No.: 5,843,725
Issued: Dec. 1, 1998
Appl. No.: 08/475,458
Filed: Jun. 7, 1995

Certificate of Correction issued Jan. 1, 2002.

Related U.S. Application Data

(60) Division of application No. 08/180,195, filed on Jan. 11, 1994, now Pat. No. 5,567,584, which is a continuation of application No. 07/634,510, filed on Dec. 27, 1990, now abandoned, which is a continuation-in-part of application No. 07/347,291, filed on May 2, 1989, now Pat. No. 5,155,027, which is a continuation-in-part of application No. 07/146,877, filed on Jan. 22, 1988, now abandoned.

(30) Foreign Application Priority Data

Jan. 18, 1989 (EP) .............................................. 8910087

(51) Int. Cl.
*C12N 15/10* (2006.01)
*C12N 5/10* (2006.01)

(52) U.S. Cl. .................... 435/69.7; 435/325; 435/320.1; 435/172.3; 530/387.1; 530/387.3; 530/333; 530/350; 530/399

(58) Field of Classification Search ................ 530/350, 530/387.3, 388.24, 399, 402, 387.1, 333; 435/69.7, 320.1, 325, 172.3
See application file for complete search history.

(56) References Cited

U.S. PATENT DOCUMENTS

| | | | |
|---|---|---|---|
| 4,859,609 A | 8/1989 | Dull et al. | 436/501 |
| 5,098,833 A | 3/1992 | Lasky et al. | 435/69.1 |
| 5,336,603 A | 8/1994 | Capon et al. | 435/69.7 |
| 5,428,130 A | 6/1995 | Capon et al. | 530/350 |
| 5,565,335 A | 10/1996 | Capon et al. | 435/64.7 |
| 5,605,690 A | 2/1997 | Jacobs et al. | 424/134.1 |
| 5,610,279 A | 3/1997 | Brockhaus et al. | 530/387.3 |
| 5,648,260 A | 7/1997 | Winter et al. | 435/252.3 |
| 5,650,150 A | 7/1997 | Gillies | 424/134.1 |
| 5,712,155 A | 1/1998 | Smith et al. | 435/320.1 |
| 5,726,037 A | 3/1998 | Bodary et al. | 435/69.1 |
| 5,750,375 A | 5/1998 | Sledziewski et al. | 435/69.7 |
| 6,004,781 A | 12/1999 | Seed | 435/69.7 |
| 6,018,026 A | 1/2000 | Sledziewski et al. | 530/350 |

OTHER PUBLICATIONS

Bierer, Barbara E., et al., "The Biologic Roles of CD2, CD4, and CD8 in T–cell Activation", *Ann. Rev. Immunol.*, vol. 7, (1989),579–599.

Ellis, Leland, et al., "Truncation of the Ectodomain of the Human Insulin Receptor Results in Secretion of a Soluble Insulin Binding Protein from Transfected CHO Cells", *Journal of Molecular Recognition*, vol. 1, No. 1, (1988),25–31.

Estess, Mark D., et al., "Analysis of T–Cell Receptor Structure and Function Using Chimeric T–Cell Receptor/Immunoglobulin Molecules", *J. Cell Biochem. Suppl. O* (11 part D), (1987),258.

Fernley, R. T., et al., "The Application of Recombinant DNA Techniques to the Study of Cell Membrane Receptors", *Molecular and Chemical Characterization of Membrane Receptors*, (1984),261–282.

Gascoigne, Nicholas R., et al., "Chimeric Proteins Produced By T Cell Receptor–Immunoglobulin Gene Fusions", *Immune Regulation by Characterized Polypeptides*, (1987), 617–627.

Gascoigne, Nicholas R., et al., "Secretion of Chimeric T Cell Receptor–Immunoglobulin Fushion Proteins", *J. Cell Biochem. Suppl. O* (11 part D), (1987),259.

Goverman, Joan, et al., "Chimeric T–Cell Receptor Genes as Tools in Analyzing T–Cell/Target–Cell Interactions", *J. Cell Biochem. Suppl. O* (11 part D), (1987),259.

Himmler, Adolf, et al., "Molecular Cloning and Expression of Human and Rat Tumor Necrosis Factor Receptor Chain (p60) and Its Soluble Derivative, Tumor Necrosis Factor–Binding Protein", *DNA and Cell Biology*, vol. 9, No. 10, (1990),705–715.

Ratnofsky, Sheldon E., et al., "Expression and Function of CD8 in a Murine T Cell Hybridoma", *J. Exp. Med.*, vol. 166, (Dec. 1987), 1747–1757.

Smith, Richard A., et al., "Multimeric Structure of the Tumor Necrosis Factor Receptor of HeLa Cells", *Journal of Biological Chemistry*, vol. 264, No. 25, (Sep. 5, 1989), 14646–14652.

Traunecker, Andre, et al., "Highly Efficient Neutralization of HIV with Recombinant CD4–immunoglobulin molecules", *Nature*, vol. 339, (May 4, 1989),68–70.

(Continued)

*Primary Examiner*—Bennett Celsa

(57) ABSTRACT

Methods for producing secreted receptor analogs and biologically active peptide dimers are disclosed. The methods for producing secreted receptor analogs and biologically active peptide dimers utilize a DNA sequence encoding a receptor analog or a peptide requiring dimerization for biological activity joined to a dimerizing protein. The receptor analog includes a ligand-binding domain. Polypeptides comprising essentially the extracellular domain of a human PDGF receptor fused to dimerizing proteins, the portion being capable of binding human PDGF or an isoform thereof, are also disclosed. The polypeptides may be used within methods for determining the presence of and for purifying human PDGF or isoforms thereof.

OTHER PUBLICATIONS

Traunecker, Andre, et al., "Solubilizing the T–cell receptor—problems in solution", *Immunology Today*, vol. 10, (1989),29–32.

Ullrich, Axel, et al., "Signal Transduction by Receptors with Tyrosine Kinase Activity", *Cell*, vol. 61, (1990),203–212.

Van Brunt, Jennifer, "Lymphokine Receptors as Therapeutics", *Bio/Technology*, vol. 7, (Jul., 1989),668–669.

Weber, David V., et al., "Medium–Scale Ligand–Affinity Purification of Two Soluble Forms of Human Interleukin–2 Receptor", *Journal of Chromatography*, vol. 431, (1988), 55–63.

Whittaker, Jonathan, et al., "Secretion of Soluble Functional Insulin Receptors by Transfected NIH3T3 Cells", *Journal of Biological Chemistry*, vol. 263, No. 7, (Mar. 5, 1988), 3063–3066.

Williams, Gareth T., et al., "Signal Transduction by Receptors with Tyrosine Kinase Activity", *Gene*, vol. 43, (1986), 319–324.

Williams, Alan F., et al., "The Immunoglobulin Superfamily—Domains for Cell Surface Recognition", *Ann. Rev. Immunol*, vol. 6, (1988),381–405.

Broach, James R., et al., "Transformation in Yeast: Development of a Hybrid Cloning Vector and Isolation of the CAN1 Gene", *Gene*, 8, (1979),pp. 121–133.

Struhl, Kevin, et al., "High–Frequency Transformation of Yeast: Autonomous Replication of Hybrid DNA Molecules", *Proc. Natl. Acad. Sci. USA*, 76, (1979),pp. 1035–1039.

Ellis, Leland, et al., "Linking functional domains of the human insulin receptor with the bacterial aspartate receptor", *Proc. Natl. Acad. Sci. USA*, vol. 83, (Nov. 1986), pp. 8137–8141.

Gascoigne, Nicholas R., et al., "Secretion of a chimeric T–cell receptor–immunoglobulin protein", *Proc. Natl. Acad. Sci.*, vol. 84, (May 1987), pp. 2936–2940.

Riedel, Heimo, et al., "A chimeric, ligand–binding v–erbB/EGF receptor retains transforming potential", *Science*, vol. 236,(Apr. 10, 1987), pp. 197–200.

Traunecker, Andre, et al., "Soluble CD4 molecules neutralize human immunodeficiency virus type 1", *Nature*, vol. 331,(Jan. 1988), pp. 84–86.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9–13, 15–20 and 28–49 is confirmed.

Claims 1, 14 and 21 are determined to be patentable as amended.

Claims 2–8 and 22–27, dependent on an amended claim, are determined to be patentable.

New claims 50 and 51 are added and determined to be patentable.

1. A method for producing a secreted active dimerized polypeptide fusion, comprising:
   introducing into a eukaryotic host cell a DNA construct comprising a transcriptional promoter operatively linked to a secretory signal sequence followed downstream by and in proper reading frame with a DNA sequence encoding a non-immunoglobulin polypeptide requiring dimerization for biological activity joined to a dimerizing protein heterologous to said non-immunoglobulin polypeptide;
   growing said host cell in an appropriate growth medium under physiological conditions to allow the secretion of a dimerized polypeptide fusion encoded by said DNA sequence; and
   isolating said dimerized polypeptide fusion from said host cell,
   *wherein the dimerizing protein is selected from the group consisting of yeast invertase; at least a portion of an immunoglobulin light chain comprising at least an immunoglobulin light chain constant region domain; and at least a portion of an immunoglobulin heavy chain comprising at least an immunoglobulin heavy chain constant region domain.*

14. The method of claim 9 wherein said non-immunoglobulin polypeptide requiring dimerization for biological activity is selected from the group consisting of a polypeptide comprising the amino acid sequence of FIGS. 1A–1D (Sequence ID Numbers 1 and 2) from isoleucine, number 29, to lysine, number 531, a polypeptide comprising the amino acid sequence of [FOGS.] *FIGS.* 1A–1D (Sequence ID Numbers 1 and 2) from isoleucine, number 29, to methionine, number 441, and a polypeptide comprising the amino acid sequence of FIGS. 11A–11 D (Sequence ID Numbers 35 and 36) from glutamine, number 24 to glutamic acid, number 524.

21. A method for producing a secreted receptor analog, comprising:
   introducing into a eukaryotic host cell a DNA construct comprising a transcriptional promoter operatively linked to at least one secretory signal sequence followed downstream by and in proper reading frame with a DNA sequence encoding a ligand-binding domain of a receptor requiring dimerization for biological activity joined to a dimerizing protein heterologous to said ligand-binding domain, and optionally an immunoglobulin hinge or variable region *joined* to said dimerizing protein;
   growing said host cell in an appropriate growth medium under physiological conditions to allow the secretion of a receptor analog encoded by said DNA sequence; and
   isolating said receptor analog from said host cell,
   *wherein the dimerizing protein is selected from the group consisting of yeast invertase; at least a portion of an immunoglobulin light chain comprising at least an immunoglobulin light chain constant region domain; and at least a portion of an immunoglobulin heavy chain comprising at least an immunoglobulin heavy chain constant region domain.*

*50. The method of claim 1 wherein the dimerizing protein is at least a portion of an immunoglobulin heavy chain comprising at least an immunoglobulin heavy chain constant region domain joined to an immunoglobulin heavy chain hinge region.*

*51. The method of claim 21 wherein the dimerizing protein is at least a portion of an immunoglobulin heavy chain comprising at least an immunoglobulin heavy chain constant region domain, and an immunoglobulin heavy chain hinge region is joined to the dimerizing protein.*

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 4465 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: N ( i v ) ANTI-SENSE: N ( v i ) ORIGINAL SOURCE:
        ( A ) ORGANISM: Homo sapiens
        ( D ) DEVELOPMENTAL STAGE: Adult
        ( F ) TISSUE TYPE: Skin
        ( G ) CELL TYPE: fibroblasts ( v i i ) IMMEDIATE SOURCE:
        ( B ) CLONE: pR-rX1

( i x ) FEATURE:
        ( A ) NAME/KEY: CDS
        ( B ) LOCATION: 354..3671
        ( D ) OTHER INFORMATION:

( x i ) SEQUENCE DESCRIPTION: SEQ ID NO:1:

```
CCCTCAGCCC   TGCTGCCCAG   CACGAGCCTG   TGCTCGCCCT   GCCCAACGCA   GACAGCCAGA         60

CCCAGGGCGG   CCCCTCTGGC   GGCTCTGCTC   CTCCCGAAGG   ATGCTTGGGG   AGTGAGGCGA        120

AGCTGGGCGC   TCCTCTCCCC   TACAGCAGCC   CCCTTCCTCC   ATCCCTCTGT   TCTCCTGAGC        180

CTTCAGGAGC   CTGCACCAGT   CCTGCCTGTC   CTTCTACTCA   GCTGTTACCC   ACTCTGGGAC        240

CAGCAGTCTT   TCTGATAACT   GGGAGAGGGC   AGTAAGGAGG   ACTTCCTGGA   GGGGGTGACT        300

GTCCAGAGCC   TGGAACTGTG   CCCACACCAG   AAGCCATCAG   CAGCAAGGAC   ACC ATG         356
                                                                   Met
                                                                    1
```

| | | | | | | | | | | | | | | | | |
|---|---|---|---|---|---|---|---|---|---|---|---|---|---|---|---|---|
| CGG | CTT | CCG | GGT | GCG | ATG | CCA | GCT | CTG | GCC | CTC | AAA | GGC | GAG | CTG | CTG | 404 |
| Arg | Leu | Pro | Gly | Ala | Met | Pro | Ala | Leu | Ala | Leu | Lys | Gly | Glu | Leu | Leu | |
| | | | 5 | | | | 10 | | | | | | 15 | | | |
| TTG | CTG | TCT | CTC | CTG | TTA | CTT | CTG | GAA | CCA | CAG | ATC | TCT | CAG | GGC | CTG | 452 |
| Leu | Leu | Ser | Leu | Leu | Leu | Leu | Leu | Glu | Pro | Gln | Ile | Ser | Gln | Gly | Leu | |
| | | 20 | | | | | 25 | | | | | 30 | | | | |
| GTC | GTC | ACA | CCC | CCG | GGG | CCA | GAG | CTT | GTC | CTC | AAT | GTC | TCC | AGC | ACC | 500 |
| Val | Val | Thr | Pro | Pro | Gly | Pro | Glu | Leu | Val | Leu | Asn | Val | Ser | Ser | Thr | |
| | | 35 | | | | 40 | | | | | 45 | | | | | |
| TTC | GTT | CTG | ACC | TGC | TCG | GGT | TCA | GCT | CCG | GTG | GTG | TGG | GAA | CGG | ATG | 548 |
| Phe | Val | Leu | Thr | Cys | Ser | Gly | Ser | Ala | Pro | Val | Val | Trp | Glu | Arg | Met | |
| 50 | | | | | 55 | | | | | 60 | | | | | 65 | |
| TCC | CAG | GAG | CCC | CCA | CAG | GAA | ATG | GCC | AAG | GCC | CAG | GAT | GGC | ACC | TTC | 596 |
| Ser | Gln | Glu | Pro | Pro | Gln | Glu | Met | Ala | Lys | Ala | Gln | Asp | Gly | Thr | Phe | |
| | | | | 70 | | | | | 75 | | | | | 80 | | |
| TCC | AGC | GTG | CTC | ACA | CTG | ACC | AAC | CTC | ACT | GGG | CTA | GAC | ACG | GGA | GAA | 644 |
| Ser | Ser | Val | Leu | Thr | Leu | Thr | Asn | Leu | Thr | Gly | Leu | Asp | Thr | Gly | Glu | |
| | | | 85 | | | | | 90 | | | | | 95 | | | |
| TAC | TTT | TGC | ACC | CAC | AAT | GAC | TCC | CGT | GGA | CTG | GAG | ACC | GAT | GAG | CGG | 692 |
| Tyr | Phe | Cys | Thr | His | Asn | Asp | Ser | Arg | Gly | Leu | Glu | Thr | Asp | Glu | Arg | |
| | | 100 | | | | | 105 | | | | | 110 | | | | |
| AAA | CGG | CTC | TAC | ATC | TTT | GTG | CCA | GAT | CCC | ACC | GTG | GGC | TTC | CTC | CCT | 740 |
| Lys | Arg | Leu | Tyr | Ile | Phe | Val | Pro | Asp | Pro | Thr | Val | Gly | Phe | Leu | Pro | |
| | 115 | | | | | 120 | | | | | 125 | | | | | |
| AAT | GAT | GCC | GAG | GAA | CTA | TTC | ATC | TTT | CTC | ACG | GAA | ATA | ACT | GAG | ATC | 788 |
| Asn | Asp | Ala | Glu | Glu | Leu | Phe | Ile | Phe | Leu | Thr | Glu | Ile | Thr | Glu | Ile | |
| 130 | | | | | 135 | | | | | 140 | | | | | 145 | |
| ACC | ATT | CCA | TGC | CGA | GTA | ACA | GAC | CCA | CAG | CTG | GTG | GTG | ACA | CTG | CAC | 836 |
| Thr | Ile | Pro | Cys | Arg | Val | Thr | Asp | Pro | Gln | Leu | Val | Val | Thr | Leu | His | |
| | | | | 150 | | | | | 155 | | | | | 160 | | |
| GAG | AAG | AAA | GGG | GAC | GTT | GCA | CTG | CCT | GTC | CCC | TAT | GAT | CAC | CAA | CGT | 884 |
| Glu | Lys | Lys | Gly | Asp | Val | Ala | Leu | Pro | Val | Pro | Tyr | Asp | His | Gln | Arg | |
| | | | 165 | | | | | 170 | | | | | 175 | | | |
| GGC | TTT | TCT | GGT | ATC | TTT | GAG | GAC | AGA | AGC | TAC | ATC | TGC | AAA | ACC | ACC | 932 |
| Gly | Phe | Ser | Gly | Ile | Phe | Glu | Asp | Arg | Ser | Tyr | Ile | Cys | Lys | Thr | Thr | |
| | | 180 | | | | | 185 | | | | | 190 | | | | |
| ATT | GGG | GAC | AGG | GAG | GTG | GAT | TCT | GAT | GCC | TAC | TAT | GTC | TAC | AGA | CTC | 980 |
| Ile | Gly | Asp | Arg | Glu | Val | Asp | Ser | Asp | Ala | Tyr | Tyr | Val | Tyr | Arg | Leu | |
| | 195 | | | | | 200 | | | | | 205 | | | | | |
| CAG | GTG | TCA | TCC | ATC | AAC | GTC | TCT | GTG | AAC | GCA | GTG | CAG | ACT | GTG | GTC | 1028 |
| Gln | Val | Ser | Ser | Ile | Asn | Val | Ser | Val | Asn | Ala | Val | Gln | Thr | Val | Val | |
| 210 | | | | | 215 | | | | | 220 | | | | | 225 | |
| CGC | CAG | GGT | GAG | AAC | ATC | ACC | CTC | ATG | TGC | ATT | GTG | ATC | GGG | AAT | GAG | 1076 |
| Arg | Gln | Gly | Glu | Asn | Ile | Thr | Leu | Met | Cys | Ile | Val | Ile | Gly | Asn | Glu | |
| | | | | 230 | | | | | 235 | | | | | 240 | | |
| GTG | GTC | AAC | TTC | GAG | TGG | ACA | TAC | CCC | CGC | AAA | GAA | AGT | GGG | CGG | CTG | 1124 |
| Val | Val | Asn | Phe | Glu | Trp | Thr | Tyr | Pro | Arg | Lys | Glu | Ser | Gly | Arg | Leu | |
| | | | 245 | | | | | 250 | | | | | 255 | | | |
| GTG | GAG | CCG | GTG | ACT | GAC | TTC | CTC | TTG | GAT | ATG | CCT | TAC | CAC | ATC | CGC | 1172 |
| Val | Glu | Pro | Val | Thr | Asp | Phe | Leu | Leu | Asp | Met | Pro | Tyr | His | Ile | Arg | |
| | | 260 | | | | | 265 | | | | | 270 | | | | |
| TCC | ATC | CTG | CAC | ATC | CCC | AGT | GCC | GAG | TTA | GAA | GAC | TCG | GGG | ACC | TAC | 1220 |
| Ser | Ile | Leu | His | Ile | Pro | Ser | Ala | Glu | Leu | Glu | Asp | Ser | Gly | Thr | Tyr | |
| | 275 | | | | | 280 | | | | | 285 | | | | | |
| ACC | TGC | AAT | GTG | ACG | GAG | AGT | GTG | AAT | GAC | CAT | CAG | GAT | GAA | AAG | GCC | 1268 |
| Thr | Cys | Asn | Val | Thr | Glu | Ser | Val | Asn | Asp | His | Gln | Asp | Glu | Lys | Ala | |
| 290 | | | | | 295 | | | | | 300 | | | | | 305 | |
| ATC | AAC | ATC | ACC | GTG | GTT | GAG | AGC | GGC | TAC | GTG | CGG | CTC | CTG | GGA | GAG | 1316 |
| Ile | Asn | Ile | Thr | Val | Val | Glu | Ser | Gly | Tyr | Val | Arg | Leu | Leu | Gly | Glu | |
| | | | | 310 | | | | | 315 | | | | | 320 | | |

| | | | | | | | | | | | | | | | | |
|---|---|---|---|---|---|---|---|---|---|---|---|---|---|---|---|---|
| GTG | GGC | ACA | CTA | CAA | TTT | GCT | GAG | CTG | CAT | CGG | AGC | CGG | ACA | CTG | CAG | 1364 |
| Val | Gly | Thr | Leu | Gln | Phe | Ala | Glu | Leu | His | Arg | Ser | Arg | Thr | Leu | Gln | |
| | | 325 | | | | | 330 | | | | | 335 | | | | |
| GTA | GTG | TTC | GAG | GCC | TAC | CCA | CCG | CCC | ACT | GTC | CTG | TGG | TTC | AAA | GAC | 1412 |
| Val | Val | Phe | Glu | Ala | Tyr | Pro | Pro | Pro | Thr | Val | Leu | Trp | Phe | Lys | Asp | |
| | 340 | | | | | 345 | | | | | 350 | | | | | |
| AAC | CGC | ACC | CTG | GGC | GAC | TCC | AGC | GCT | GGC | GAA | ATC | GCC | CTG | TCC | ACG | 1460 |
| Asn | Arg | Thr | Leu | Gly | Asp | Ser | Ser | Ala | Gly | Glu | Ile | Ala | Leu | Ser | Thr | |
| 355 | | | | | 360 | | | | | 365 | | | | | | |
| CGC | AAC | GTG | TCG | GAG | ACC | CGG | TAT | GTG | TCA | GAG | CTG | ACA | CTG | GTT | CGC | 1508 |
| Arg | Asn | Val | Ser | Glu | Thr | Arg | Tyr | Val | Ser | Glu | Leu | Thr | Leu | Val | Arg | |
| 370 | | | | | 375 | | | | | 380 | | | | | 385 | |
| GTG | AAG | GTG | GCA | GAG | GCT | GGC | CAC | TAC | ACC | ATG | CGG | GCC | TTC | CAT | GAG | 1556 |
| Val | Lys | Val | Ala | Glu | Ala | Gly | His | Tyr | Thr | Met | Arg | Ala | Phe | His | Glu | |
| | | | | 390 | | | | | 395 | | | | | 400 | | |
| GAT | GCT | GAG | GTC | CAG | CTC | TCC | TTC | CAG | CTA | CAG | ATC | AAT | GTC | CCT | GTC | 1604 |
| Asp | Ala | Glu | Val | Gln | Leu | Ser | Phe | Gln | Leu | Gln | Ile | Asn | Val | Pro | Val | |
| | | | 405 | | | | | 410 | | | | | 415 | | | |
| CGA | GTG | CTG | GAG | CTA | AGT | GAG | AGC | CAC | CCT | GAC | AGT | GGG | GAA | CAG | ACA | 1652 |
| Arg | Val | Leu | Glu | Leu | Ser | Glu | Ser | His | Pro | Asp | Ser | Gly | Glu | Gln | Thr | |
| | | 420 | | | | | 425 | | | | | 430 | | | | |
| GTC | CGC | TGT | CGT | GGC | CGG | GGC | ATG | CCC | CAG | CCG | AAC | ATC | ATC | TGG | TCT | 1700 |
| Val | Arg | Cys | Arg | Gly | Arg | Gly | Met | Pro | Gln | Pro | Asn | Ile | Ile | Trp | Ser | |
| | 435 | | | | | 440 | | | | | 445 | | | | | |
| GCC | TGC | AGA | GAC | CTC | AAA | AGG | TGT | CCA | CGT | GAG | CTG | CCG | CCC | ACG | CTG | 1748 |
| Ala | Cys | Arg | Asp | Leu | Lys | Arg | Cys | Pro | Arg | Glu | Leu | Pro | Pro | Thr | Leu | |
| 450 | | | | | 455 | | | | | 460 | | | | | 465 | |
| CTG | GGG | AAC | AGT | TCC | GAA | GAG | GAG | AGC | CAG | CTG | GAG | ACT | AAC | GTG | ACG | 1796 |
| Leu | Gly | Asn | Ser | Ser | Glu | Glu | Glu | Ser | Gln | Leu | Glu | Thr | Asn | Val | Thr | |
| | | | | 470 | | | | | 475 | | | | | 480 | | |
| TAC | TGG | GAG | GAG | GAG | CAG | GAG | TTT | GAG | GTG | GTG | AGC | ACA | CTG | CGT | CTG | 1844 |
| Tyr | Trp | Glu | Glu | Glu | Gln | Glu | Phe | Glu | Val | Val | Ser | Thr | Leu | Arg | Leu | |
| | | | | 485 | | | | | 490 | | | | | 495 | | |
| CAG | CAC | GTG | GAT | CGG | CCA | CTG | TCG | GTG | CGC | TGC | ACG | CTG | CGC | AAC | GCT | 1892 |
| Gln | His | Val | Asp | Arg | Pro | Leu | Ser | Val | Arg | Cys | Thr | Leu | Arg | Asn | Ala | |
| | | 500 | | | | | 505 | | | | | 510 | | | | |
| GTG | GGC | CAG | GAC | ACG | CAG | GAG | GTC | ATC | GTG | GTG | CCA | CAC | TCC | TTG | CCC | 1940 |
| Val | Gly | Gln | Asp | Thr | Gln | Glu | Val | Ile | Val | Val | Pro | His | Ser | Leu | Pro | |
| | 515 | | | | | 520 | | | | | 525 | | | | | |
| TTT | AAG | GTG | GTG | GTG | ATC | TCA | GCC | ATC | CTG | GCC | CTG | GTG | GTG | CTC | ACC | 1988 |
| Phe | Lys | Val | Val | Val | Ile | Ser | Ala | Ile | Leu | Ala | Leu | Val | Val | Leu | Thr | |
| 530 | | | | | 535 | | | | | 540 | | | | | 545 | |
| ATC | ATC | TCC | CTT | ATC | ATC | CTC | ATC | ATG | CTT | TGG | CAG | AAG | AAG | CCA | CGT | 2036 |
| Ile | Ile | Ser | Leu | Ile | Ile | Leu | Ile | Met | Leu | Trp | Gln | Lys | Lys | Pro | Arg | |
| | | | | 550 | | | | | 555 | | | | | 560 | | |
| TAC | GAG | ATC | CGA | TGG | AAG | GTG | ATT | GAG | TCT | GTG | AGC | TCT | GAC | GGC | CAT | 2084 |
| Tyr | Glu | Ile | Arg | Trp | Lys | Val | Ile | Glu | Ser | Val | Ser | Ser | Asp | Gly | His | |
| | | | 565 | | | | | 570 | | | | | 575 | | | |
| GAG | TAC | ATC | TAC | GTG | GAC | CCC | ATG | CAG | CTG | CCC | TAT | GAC | TCC | ACG | TGG | 2132 |
| Glu | Tyr | Ile | Tyr | Val | Asp | Pro | Met | Gln | Leu | Pro | Tyr | Asp | Ser | Thr | Trp | |
| | | 580 | | | | | 585 | | | | | 590 | | | | |
| GAG | CTG | CCG | CGG | GAC | CAG | CTT | GTG | CTG | GGA | CGC | ACC | CTC | GGC | TCT | GGG | 2180 |
| Glu | Leu | Pro | Arg | Asp | Gln | Leu | Val | Leu | Gly | Arg | Thr | Leu | Gly | Ser | Gly | |
| | | 595 | | | | | 600 | | | | | 605 | | | | |
| GCC | TTT | GGG | CAG | GTG | GTG | GAG | GCC | ACG | GCT | CAT | GGC | CTG | AGC | CAT | TCT | 2228 |
| Ala | Phe | Gly | Gln | Val | Val | Glu | Ala | Thr | Ala | His | Gly | Leu | Ser | His | Ser | |
| 610 | | | | | 615 | | | | | 620 | | | | | 625 | |
| CAG | GCC | ACG | ATG | AAA | GTG | GCC | GTC | AAG | ATG | CTT | AAA | TCC | ACA | GCC | CGC | 2276 |
| Gln | Ala | Thr | Met | Lys | Val | Ala | Val | Lys | Met | Leu | Lys | Ser | Thr | Ala | Arg | |
| | | | | 630 | | | | | 635 | | | | | 640 | | |

| | | | | | | | | | | | | | | | | |
|---|---|---|---|---|---|---|---|---|---|---|---|---|---|---|---|---|
| AGC | AGT | GAG | AAG | CAA | GCC | CTT | ATG | TCG | GAG | CTG | AAG | ATC | ATG | AGT | CAC | 2324 |
| Ser | Ser | Glu | Lys | Gln | Ala | Leu | Met | Ser | Glu | Leu | Lys | Ile | Met | Ser | His | |
| | | | 645 | | | | 650 | | | | | 655 | | | | |
| CTT | GGG | CCC | CAC | CTG | AAC | GTG | GTC | AAC | CTG | TTG | GGG | GCC | TGC | ACC | AAA | 2372 |
| Leu | Gly | Pro | His | Leu | Asn | Val | Val | Asn | Leu | Leu | Gly | Ala | Cys | Thr | Lys | |
| | | 660 | | | | | 665 | | | | | 670 | | | | |
| GGA | GGA | CCC | ATC | TAT | ATC | ATC | ACT | GAG | TAC | TGC | CGC | TAC | GGA | GAC | CTG | 2420 |
| Gly | Gly | Pro | Ile | Tyr | Ile | Ile | Thr | Glu | Tyr | Cys | Arg | Tyr | Gly | Asp | Leu | |
| | 675 | | | | | 680 | | | | | 685 | | | | | |
| GTG | GAC | TAC | CTG | CAC | CGC | AAC | AAA | CAC | ACC | TTC | CTG | CAG | CAC | CAC | TCC | 2468 |
| Val | Asp | Tyr | Leu | His | Arg | Asn | Lys | His | Thr | Phe | Leu | Gln | His | His | Ser | |
| 690 | | | | | 695 | | | | | 700 | | | | | 705 | |
| GAC | AAG | CGC | CGC | CCG | CCC | AGC | GCG | GAG | CTC | TAC | AGC | AAT | GCT | CTG | CCC | 2516 |
| Asp | Lys | Arg | Arg | Pro | Pro | Ser | Ala | Glu | Leu | Tyr | Ser | Asn | Ala | Leu | Pro | |
| | | | | 710 | | | | | 715 | | | | | 720 | | |
| GTT | GGG | CTC | CCC | CTG | CCC | AGC | CAT | GTG | TCC | TTG | ACC | GGG | GAG | AGC | GAC | 2564 |
| Val | Gly | Leu | Pro | Leu | Pro | Ser | His | Val | Ser | Leu | Thr | Gly | Glu | Ser | Asp | |
| | | | 725 | | | | | 730 | | | | | 735 | | | |
| GGT | GGC | TAC | ATG | GAC | ATG | AGC | AAG | GAC | GAG | TCG | GTG | GAC | TAT | GTG | CCC | 2612 |
| Gly | Gly | Tyr | Met | Asp | Met | Ser | Lys | Asp | Glu | Ser | Val | Asp | Tyr | Val | Pro | |
| | | 740 | | | | | 745 | | | | | 750 | | | | |
| ATG | CTG | GAC | ATG | AAA | GGA | GAC | GTC | AAA | TAT | GCA | GAC | ATC | GAG | TCC | TCC | 2660 |
| Met | Leu | Asp | Met | Lys | Gly | Asp | Val | Lys | Tyr | Ala | Asp | Ile | Glu | Ser | Ser | |
| | 755 | | | | | 760 | | | | | 765 | | | | | |
| AAC | TAC | ATG | GCC | CCT | TAC | GAT | AAC | TAC | GTT | CCC | TCT | GCC | CCT | GAG | AGG | 2708 |
| Asn | Tyr | Met | Ala | Pro | Tyr | Asp | Asn | Tyr | Val | Pro | Ser | Ala | Pro | Glu | Arg | |
| 770 | | | | | 775 | | | | | 780 | | | | | 785 | |
| ACC | TGC | CGA | GCA | ACT | TTG | ATC | AAC | GAG | TCT | CCA | GTG | CTA | AGC | TAC | ATG | 2756 |
| Thr | Cys | Arg | Ala | Thr | Leu | Ile | Asn | Glu | Ser | Pro | Val | Leu | Ser | Tyr | Met | |
| | | | | 790 | | | | | 795 | | | | | 800 | | |
| GAC | CTC | GTG | GGC | TTC | AGC | TAC | CAG | GTG | GCC | AAT | GGC | ATG | GAG | TTT | CTG | 2804 |
| Asp | Leu | Val | Gly | Phe | Ser | Tyr | Gln | Val | Ala | Asn | Gly | Met | Glu | Phe | Leu | |
| | | | 805 | | | | | 810 | | | | | 815 | | | |
| GCC | TCC | AAG | AAC | TGC | GTC | CAC | AGA | GAC | CTG | GCG | GCT | AGG | AAC | GTG | CTC | 2852 |
| Ala | Ser | Lys | Asn | Cys | Val | His | Arg | Asp | Leu | Ala | Ala | Arg | Asn | Val | Leu | |
| | | 820 | | | | | 825 | | | | | 830 | | | | |
| ATC | TGT | GAA | GGC | AAG | CTG | GTC | AAG | ATC | TGT | GAC | TTT | GGC | CTG | GCT | CGA | 2900 |
| Ile | Cys | Glu | Gly | Lys | Leu | Val | Lys | Ile | Cys | Asp | Phe | Gly | Leu | Ala | Arg | |
| | 835 | | | | | 840 | | | | | 845 | | | | | |
| GAC | ATC | ATG | CGG | GAC | TCG | AAT | TAC | ATC | TCC | AAA | GGC | AGC | ACC | TTT | TTG | 2948 |
| Asp | Ile | Met | Arg | Asp | Ser | Asn | Tyr | Ile | Ser | Lys | Gly | Ser | Thr | Phe | Leu | |
| 850 | | | | | 855 | | | | | 860 | | | | | 865 | |
| CCT | TTA | AAG | TGG | ATG | GCT | CCG | GAG | AGC | ATC | TTC | AAC | AGC | CTC | TAC | ACC | 2996 |
| Pro | Leu | Lys | Trp | Met | Ala | Pro | Glu | Ser | Ile | Phe | Asn | Ser | Leu | Tyr | Thr | |
| | | | | 870 | | | | | 875 | | | | | 880 | | |
| ACC | CTG | AGC | GAC | GTG | TGG | TCC | TTC | GGG | ATC | CTG | CTC | TGG | GAG | ATC | TTC | 3044 |
| Thr | Leu | Ser | Asp | Val | Trp | Ser | Phe | Gly | Ile | Leu | Leu | Trp | Glu | Ile | Phe | |
| | | | 885 | | | | | 890 | | | | | 895 | | | |
| ACC | TTG | GGT | GGC | ACC | CCT | TAC | CCA | GAG | CTG | CCC | ATG | AAC | GAG | CAG | TTC | 3092 |
| Thr | Leu | Gly | Gly | Thr | Pro | Tyr | Pro | Glu | Leu | Pro | Met | Asn | Glu | Gln | Phe | |
| | | 900 | | | | | 905 | | | | | 910 | | | | |
| TAC | AAT | GCC | ATC | AAA | CGG | GGT | TAC | CGC | ATG | GCC | CAG | CCT | GCC | CAT | GCC | 3140 |
| Tyr | Asn | Ala | Ile | Lys | Arg | Gly | Tyr | Arg | Met | Ala | Gln | Pro | Ala | His | Ala | |
| | | 915 | | | | | 920 | | | | | 925 | | | | |
| TCC | GAC | GAG | ATC | TAT | GAG | ATC | ATG | CAG | AAG | TGC | TGG | GAA | GAG | AAG | TTT | 3188 |
| Ser | Asp | Glu | Ile | Tyr | Glu | Ile | Met | Gln | Lys | Cys | Trp | Glu | Glu | Lys | Phe | |
| 930 | | | | | 935 | | | | | 940 | | | | | 945 | |
| GAG | ATT | CGG | CCC | CCC | TTC | TCC | CAG | CTG | GTG | CTG | CTT | CTC | GAG | AGA | CTG | 3236 |
| Glu | Ile | Arg | Pro | Pro | Phe | Ser | Gln | Leu | Val | Leu | Leu | Leu | Glu | Arg | Leu | |
| | | | | 950 | | | | | 955 | | | | | 960 | | |

| | | | | | | | | | | | | | | | | |
|---|---|---|---|---|---|---|---|---|---|---|---|---|---|---|---|---|
| TTG | GGC | GAA | GGT | TAC | AAA | AAG | AAG | TAC | CAG | CAG | GTG | GAT | GAG | GAG | TTT | 3284 |
| Leu | Gly | Glu | Gly<br>965 | Tyr | Lys | Lys | Lys | Tyr<br>970 | Gln | Gln | Val | Asp | Glu<br>975 | Glu | Phe | |
| CTG | AGG | AGT | GAC | CAC | CCA | GCC | ATC | CTT | CGG | TCC | CAG | GCC | CGC | TTG | CCT | 3332 |
| Leu | Arg | Ser<br>980 | Asp | His | Pro | Ala | Ile | Leu<br>985 | Arg | Ser | Gln | Ala | Arg<br>990 | Leu | Pro | |
| GGG | TTC | CAT | GGC | CTC | CGA | TCT | CCC | CTG | GAC | ACC | AGC | TCC | GTC | CTC | TAT | 3380 |
| Gly | Phe<br>995 | His | Gly | Leu | Arg | Ser | Pro | Leu<br>1000 | Asp | Thr | Ser | Ser<br>1005 | Val | Leu | Tyr | |
| ACT | GCC | GTG | CAG | CCC | AAT | GAG | GGT | GAC | AAC | GAC | TAT | ATC | ATC | CCC | CTG | 3428 |
| Thr<br>1010 | Ala | Val | Gln | Pro | Asn<br>1015 | Glu | Gly | Asp | Asn | Asp<br>1020 | Tyr | Ile | Ile | Pro<br>1025 | Leu | |
| CCT | GAC | CCC | AAA | CCC | GAG | GTT | GCT | GAC | GAG | GGC | CCA | CTG | GAG | GGT | TCC | 3476 |
| Pro | Asp | Pro | Lys<br>1030 | Pro | Glu | Val | Ala | Asp<br>1035 | Glu | Gly | Pro | Leu | Glu<br>1040 | Gly | Ser | |
| CCC | AGC | CTA | GCC | AGC | TCC | ACC | CTG | AAT | GAA | GTC | AAC | ACC | TCC | TCA | ACC | 3524 |
| Pro | Ser | Leu | Ala<br>1045 | Ser | Ser | Thr | Leu | Asn<br>1050 | Glu | Val | Asn | Thr | Ser<br>1055 | Ser | Thr | |
| ATC | TCC | TGT | GAC | AGC | CCC | CTG | GAG | CCC | CAG | GAC | GAA | CCA | GAG | CCA | GAG | 3572 |
| Ile | Ser | Cys<br>1060 | Asp | Ser | Pro | Leu | Glu<br>1065 | Pro | Gln | Asp | Glu | Pro<br>1070 | Glu | Pro | Glu | |
| CCC | CAG | CTT | GAG | CTC | CAG | GTG | GAG | CCG | GAG | CCA | GAG | CTG | GAA | CAG | TTG | 3620 |
| Pro | Gln | Leu<br>1075 | Glu | Leu | Gln | Val | Glu<br>1080 | Pro | Glu | Pro | Glu | Leu<br>1085 | Glu | Gln | Leu | |
| CCG | GAT | TCG | GGG | TGC | CCT | GCG | CCT | CGG | GCG | GAA | GCA | GAG | GAT | AGC | TTC | 3668 |
| Pro | Asp | Ser | Gly<br>1090 | Cys | Pro | Ala | Pro | Arg<br>1095 | Ala | Glu | Ala | Glu | Asp<br>1100 | Ser | Phe<br>1105 | |
| CTG | TAGGGGCTG | GCCCCTACCC | TGCCCTGCCT | GAAGCTCCCC | CCCTGCCAGC | | | | | | | | | | | 3721 |
| Leu | | | | | | | | | | | | | | | | |

| | | | | | |
|---|---|---|---|---|---|
| ACCCAGCATC | TCCTGGCCTG | GCCTGACCGG | GCTTCCTGTC | AGCCAGGCTG | CCCTTATCAG | 3781 |
| CTGTCCCCTT | CTGGAAGCTT | TCTGCTCCTG | ACGTGTTGTG | CCCCAAACCC | TGGGGCTGGC | 3841 |
| TTAGGAGGCA | AGAAAACTGC | AGGGGCCGTG | ACCAGCCCTC | TGCCTCCAGG | GAGGCCAACT | 3901 |
| GACTCTGAGC | CAGGGTTCCC | CCAGGGAACT | CAGTTTTCCC | ATATGTAAGA | TGGGAAAGTT | 3961 |
| AGGCTTGATG | ACCCAGAATC | TAGGATTCTC | TCCCTGGCTG | ACACGGTGGG | GAGACCGAAT | 4021 |
| CCCTCCCTGG | GAAGATTCTT | GGAGTTACTG | AGGTGGTAAA | TTAACATTTT | TTCTGTTCAG | 4081 |
| CCAGCTACCC | CTCAAGGAAT | CATAGCTCTC | TCCTCGCACT | TTTTATCCAC | CCAGGAGCTA | 4141 |
| GGGAAGAGAC | CCTAGCCTCC | CTGGCTGCTG | GCTGAGCTAG | GGCCTAGCTT | GAGCAGTGTT | 4201 |
| GCCTCATCCA | GAAGAAAGCC | AGTCTCCTCC | CTATGATGCC | AGTCCCTGCG | TTCCCTGGCC | 4261 |
| CGAGCTGGTC | TGGGGCCATT | AGGCAGCCTA | ATTAATGCTG | GAGGCTGAGC | CAAGTACAGG | 4321 |
| ACACCCCAG | CCTGCAGCCC | TTGCCCAGGG | CACTTGGAGC | ACACGCAGCC | ATAGCAAGTG | 4381 |
| CCTGTGTCCC | TGTCCTTCAG | GCCCATCAGT | CCTGGGGCTT | TTTCTTTATC | ACCCTCAGTC | 4441 |
| TTAATCCATC | CACCAGAGTC | TAGA | | | | 4465 |

( 2 ) INFORMATION FOR SEQ ID NO:2:

( i ) SEQUENCE CHARACTERISTICS:
        ( A ) LENGTH: 1106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Arg | Leu | Pro | Gly<br>5 | Ala | Met | Pro | Ala | Leu<br>10 | Ala | Leu | Lys | Gly | Glu | Leu<br>15 |

```
Leu  Leu  Leu  Ser  Leu  Leu  Leu  Leu  Leu  Glu  Pro  Gln  Ile  Ser  Gln  Gly
               20                  25                      30

Leu  Val  Val  Thr  Pro  Pro  Gly  Pro  Glu  Leu  Val  Leu  Asn  Val  Ser  Ser
               35                  40                      45

Thr  Phe  Val  Leu  Thr  Cys  Ser  Gly  Ser  Ala  Pro  Val  Trp  Glu  Arg
     50                  55                       60

Met  Ser  Gln  Glu  Pro  Gln  Glu  Met  Ala  Lys  Ala  Gln  Asp  Gly  Thr
65                       70                  75                            80

Phe  Ser  Ser  Val  Leu  Thr  Leu  Thr  Asn  Leu  Thr  Gly  Leu  Asp  Thr  Gly
                85                  90                              95

Glu  Tyr  Phe  Cys  Thr  His  Asn  Asp  Ser  Arg  Gly  Leu  Glu  Thr  Asp  Glu
               100                 105                     110

Arg  Lys  Arg  Leu  Tyr  Ile  Phe  Val  Pro  Asp  Pro  Thr  Val  Gly  Phe  Leu
          115                      120                     125

Pro  Asn  Asp  Ala  Glu  Glu  Leu  Phe  Ile  Phe  Leu  Thr  Glu  Ile  Thr  Glu
     130                      135                     140

Ile  Thr  Ile  Pro  Cys  Arg  Val  Thr  Asp  Pro  Gln  Leu  Val  Val  Thr  Leu
145                 150                      155                           160

His  Glu  Lys  Lys  Gly  Asp  Val  Ala  Leu  Pro  Val  Pro  Tyr  Asp  His  Gln
                165                      170                     175

Arg  Gly  Phe  Ser  Gly  Ile  Phe  Glu  Asp  Arg  Ser  Tyr  Ile  Cys  Lys  Thr
               180                      185                     190

Thr  Ile  Gly  Asp  Arg  Glu  Val  Asp  Ser  Asp  Ala  Tyr  Tyr  Val  Tyr  Arg
          195                      200                     205

Leu  Gln  Val  Ser  Ser  Ile  Asn  Val  Ser  Val  Asn  Ala  Val  Gln  Thr  Val
     210                      215                     220

Val  Arg  Gln  Gly  Glu  Asn  Ile  Thr  Leu  Met  Cys  Ile  Val  Ile  Gly  Asn
225                      230                 235                           240

Glu  Val  Val  Asn  Phe  Glu  Trp  Thr  Tyr  Pro  Arg  Lys  Glu  Ser  Gly  Arg
               245                      250                     255

Leu  Val  Glu  Pro  Val  Thr  Asp  Phe  Leu  Leu  Asp  Met  Pro  Tyr  His  Ile
               260                      265                     270

Arg  Ser  Ile  Leu  His  Ile  Pro  Ser  Ala  Glu  Leu  Glu  Asp  Ser  Gly  Thr
          275                      280                     285

Tyr  Thr  Cys  Asn  Val  Thr  Glu  Ser  Val  Asn  Asp  His  Gln  Asp  Glu  Lys
     290                      295                     300

Ala  Ile  Asn  Ile  Thr  Val  Val  Glu  Ser  Gly  Tyr  Val  Arg  Leu  Leu  Gly
305                      310                      315                      320

Glu  Val  Gly  Thr  Leu  Gln  Phe  Ala  Glu  Leu  His  Arg  Ser  Arg  Thr  Leu
               325                      330                     335

Gln  Val  Val  Phe  Glu  Ala  Tyr  Pro  Pro  Thr  Val  Leu  Trp  Phe  Lys
               340                      345                     350

Asp  Asn  Arg  Thr  Leu  Gly  Asp  Ser  Ser  Ala  Gly  Glu  Ile  Ala  Leu  Ser
          355                      360                     365

Thr  Arg  Asn  Val  Ser  Glu  Thr  Arg  Tyr  Val  Ser  Glu  Leu  Thr  Leu  Val
     370                      375                     380

Arg  Val  Lys  Val  Ala  Glu  Ala  Gly  His  Tyr  Thr  Met  Arg  Ala  Phe  His
385                      390                      395                      400

Glu  Asp  Ala  Glu  Val  Gln  Leu  Ser  Phe  Gln  Leu  Gln  Ile  Asn  Val  Pro
               405                      410                     415

Val  Arg  Val  Leu  Glu  Leu  Ser  Glu  Ser  His  Pro  Asp  Ser  Gly  Glu  Gln
               420                      425                     430

Thr  Val  Arg  Cys  Arg  Gly  Arg  Gly  Met  Pro  Gln  Pro  Asn  Ile  Ile  Trp
          435                      440                     445
```

-continued

| | | | | | | | | | | | | | | |
|---|---|---|---|---|---|---|---|---|---|---|---|---|---|---|
|Ser|Ala|Cys|Arg|Asp|Leu|Lys|Arg|Cys|Pro|Arg|Glu|Leu|Pro|Pro|Thr|
| |450| | | |455| | | |460| | | | | |
|Leu|Leu|Gly|Asn|Ser|Ser|Glu|Glu|Glu|Ser|Gln|Leu|Glu|Thr|Asn|Val|
|465| | | | |470| | | |475| | | | |480|
|Thr|Tyr|Trp|Glu|Glu|Glu|Gln|Glu|Phe|Glu|Val|Val|Ser|Thr|Leu|Arg|
| | | | |485| | | |490| | | | |495| |
|Leu|Gln|His|Val|Asp|Arg|Pro|Leu|Ser|Val|Arg|Cys|Thr|Leu|Arg|Asn|
| | | |500| | | | |505| | | | |510| |
|Ala|Val|Gly|Gln|Asp|Thr|Gln|Glu|Val|Ile|Val|Val|Pro|His|Ser|Leu|
| | | |515| | | |520| | | | |525| | |
|Pro|Phe|Lys|Val|Val|Val|Ile|Ser|Ala|Ile|Leu|Ala|Leu|Val|Val|Leu|
| |530| | | |535| | | | |540| | | | |
|Thr|Ile|Ile|Ser|Leu|Ile|Ile|Leu|Ile|Met|Leu|Trp|Gln|Lys|Lys|Pro|
|545| | | |550| | | | |555| | | | |560| |
|Arg|Tyr|Glu|Ile|Arg|Trp|Lys|Val|Ile|Glu|Ser|Val|Ser|Ser|Asp|Gly|
| | | | |565| | | |570| | | | |575| |
|His|Glu|Tyr|Ile|Tyr|Val|Asp|Pro|Met|Gln|Leu|Pro|Tyr|Asp|Ser|Thr|
| | | |580| | | |585| | | | |590| | |
|Trp|Glu|Leu|Pro|Arg|Asp|Gln|Leu|Val|Leu|Gly|Arg|Thr|Leu|Gly|Ser|
| | |595| | | |600| | | | |605| | | |
|Gly|Ala|Phe|Gly|Gln|Val|Val|Glu|Ala|Thr|Ala|His|Gly|Leu|Ser|His|
| |610| | | |615| | | | |620| | | | |
|Ser|Gln|Ala|Thr|Met|Lys|Val|Ala|Val|Lys|Met|Leu|Lys|Ser|Thr|Ala|
|625| | | |630| | | | |635| | | | |640|
|Arg|Ser|Ser|Glu|Lys|Gln|Ala|Leu|Met|Ser|Glu|Leu|Lys|Ile|Met|Ser|
| | | |645| | | | |650| | | | |655| |
|His|Leu|Gly|Pro|His|Leu|Asn|Val|Val|Asn|Leu|Leu|Gly|Ala|Cys|Thr|
| | |660| | | | |665| | | | |670| | |
|Lys|Gly|Gly|Pro|Ile|Tyr|Ile|Ile|Thr|Glu|Tyr|Cys|Arg|Tyr|Gly|Asp|
| | |675| | | |680| | | | |685| | | |
|Leu|Val|Asp|Tyr|Leu|His|Arg|Asn|Lys|His|Thr|Phe|Leu|Gln|His|His|
| |690| | | |695| | | | |700| | | | |
|Ser|Asp|Lys|Arg|Arg|Pro|Pro|Ser|Ala|Glu|Leu|Tyr|Ser|Asn|Ala|Leu|
|705| | | |710| | | | |715| | | | |720|
|Pro|Val|Gly|Leu|Pro|Leu|Pro|Ser|His|Val|Ser|Leu|Thr|Gly|Glu|Ser|
| | | |725| | | | |730| | | | |735| |
|Asp|Gly|Gly|Tyr|Met|Asp|Met|Ser|Lys|Asp|Glu|Ser|Val|Asp|Tyr|Val|
| | |740| | | |745| | | | |750| | | |
|Pro|Met|Leu|Asp|Met|Lys|Gly|Asp|Val|Lys|Tyr|Ala|Asp|Ile|Glu|Ser|
| |755| | | |760| | | | |765| | | | |
|Ser|Asn|Tyr|Met|Ala|Pro|Tyr|Asp|Asn|Tyr|Val|Pro|Ser|Ala|Pro|Glu|
|770| | | |775| | | | |780| | | | | |
|Arg|Thr|Cys|Arg|Ala|Thr|Leu|Ile|Asn|Glu|Ser|Pro|Val|Leu|Ser|Tyr|
|785| | | |790| | | | |795| | | | |800|
|Met|Asp|Leu|Val|Gly|Phe|Ser|Tyr|Gln|Val|Ala|Asn|Gly|Met|Glu|Phe|
| | | |805| | | |810| | | | |815| | |
|Leu|Ala|Ser|Lys|Asn|Cys|Val|His|Arg|Asp|Leu|Ala|Ala|Arg|Asn|Val|
| | | |820| | | |825| | | | |830| | |
|Leu|Ile|Cys|Glu|Gly|Lys|Leu|Val|Lys|Ile|Cys|Asp|Phe|Gly|Leu|Ala|
| | |835| | | |840| | | | |845| | | |
|Arg|Asp|Ile|Met|Arg|Asp|Ser|Asn|Tyr|Ile|Ser|Lys|Gly|Ser|Thr|Phe|
| |850| | | |855| | | | |860| | | | |
|Leu|Pro|Leu|Lys|Trp|Met|Ala|Pro|Glu|Ser|Ile|Phe|Asn|Ser|Leu|Tyr|

| | | | | | | | | | | | | | | | |
|---|---|---|---|---|---|---|---|---|---|---|---|---|---|---|---|
| | | | 865 | | | | 870 | | | | 875 | | | | 880 |
| Thr | Thr | Leu | Ser | Asp | Val | Trp | Ser | Phe | Gly | Ile | Leu | Leu | Trp | Glu | Ile |
| | | | 885 | | | | 890 | | | | | | | 895 | |
| Phe | Thr | Leu | Gly | Gly | Thr | Pro | Tyr | Pro | Glu | Leu | Pro | Met | Asn | Glu | Gln |
| | | | 900 | | | | 905 | | | | | | 910 | | |
| Phe | Tyr | Asn | Ala | Ile | Lys | Arg | Gly | Tyr | Arg | Met | Ala | Gln | Pro | Ala | His |
| | | 915 | | | | 920 | | | | | 925 | | | | |
| Ala | Ser | Asp | Glu | Ile | Tyr | Glu | Ile | Met | Gln | Lys | Cys | Trp | Glu | Glu | Lys |
| 930 | | | | | 935 | | | | | 940 | | | | | |
| Phe | Glu | Ile | Arg | Pro | Pro | Phe | Ser | Gln | Leu | Val | Leu | Leu | Leu | Glu | Arg |
| 945 | | | | 950 | | | | | 955 | | | | | | 960 |
| Leu | Leu | Gly | Glu | Gly | Tyr | Lys | Lys | Tyr | Gln | Gln | Val | Asp | Glu | Glu | |
| | | | | 965 | | | | 970 | | | | | 975 | | |
| Phe | Leu | Arg | Ser | Asp | His | Pro | Ala | Ile | Leu | Arg | Ser | Gln | Ala | Arg | Leu |
| | | | 980 | | | | 985 | | | | | 990 | | | |
| Pro | Gly | Phe | His | Gly | Leu | Arg | Ser | Pro | Leu | Asp | Thr | Ser | Ser | Val | Leu |
| | | 995 | | | | 1000 | | | | | 1005 | | | | |
| Tyr | Thr | Ala | Val | Gln | Pro | Asn | Glu | Gly | Asp | Asn | Asp | Tyr | Ile | Ile | Pro |
| | 1010 | | | | 1015 | | | | | 1020 | | | | | |
| Leu | Pro | Asp | Pro | Lys | Pro | Glu | Val | Ala | Asp | Glu | Gly | Pro | Leu | Glu | Gly |
| 1025 | | | | 1030 | | | | | 1035 | | | | | | 1040 |
| Ser | Pro | Ser | Leu | Ala | Ser | Ser | Thr | Leu | Asn | Glu | Val | Asn | Thr | Ser | Ser |
| | | | 1045 | | | | 1050 | | | | | | 1055 | | |
| Thr | Ile | Ser | Cys | Asp | Ser | Pro | Leu | Glu | Pro | Gln | Asp | Glu | Pro | Glu | Pro |
| | | | 1060 | | | | 1065 | | | | | 1070 | | | |
| Glu | Pro | Gln | Leu | Glu | Leu | Gln | Val | Glu | Pro | Glu | Pro | Glu | Leu | Glu | Gln |
| | | 1075 | | | | 1080 | | | | | 1085 | | | | |
| Leu | Pro | Asp | Ser | Gly | Cys | Pro | Ala | Pro | Arg | Ala | Glu | Ala | Glu | Asp | Ser |
| | 1090 | | | | 1095 | | | | | 1100 | | | | | |
| Phe | Leu | | | | | | | | | | | | | | |
| 1105 | | | | | | | | | | | | | | | |

( 2 ) INFORMATION FOR SEQ ID NO:3:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC871

( x i ) SEQUENCE DESCRIPTION: SEQ ID NO:3:

ATTATACGCT CTCTTCCTCA GGTAAATGAG TGCCAGGGCC GGCAAGCCCC CGCTCCA　　57

( 2 ) INFORMATION FOR SEQ ID NO:4:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: Other nucleic acid (i i i) HYPOTHETICAL: N (i v) ANTI-SENSE: N (v i i) IMMEDIATE SOURCE:
   (B) CLONE: ZC872

(x i) SEQUENCE DESCRIPTION: SEQ ID NO:4:

CCGGGGAGCG GGGGCTTGCC GGCCCTGGCA CTCATTTACC TGAGGAAGAG AGAGCT          56

(2) INFORMATION FOR SEQ ID NO:5:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (i i) MOLECULE TYPE: Other nucleic acid (i i i) HYPOTHETICAL: N (i v) ANTI-SENSE: N (v i i) IMMEDIATE SOURCE:
      (B) CLONE: ZC904

(x i) SEQUENCE DESCRIPTION: SEQ ID NO:5:

CATGGGCACG TAATCTATAG ATTCATCCTT GCTCATATCC ATGTA          45

(2) INFORMATION FOR SEQ ID NO:6:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (i i) MOLECULE TYPE: Other nucleic acid (i i i) HYPOTHETICAL: N (i v) ANTI-SENSE: N (v i i) IMMEDIATE SOURCE:
      (B) CLONE: ZC906

(x i) SEQUENCE DESCRIPTION: SEQ ID NO:6:

AAGCTGTCCT CTGCTTCAGC CAGAGGTCCT GGGCAGCC          38

(2) INFORMATION FOR SEQ ID NO:7:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (i i) MOLECULE TYPE: Other nucleic acid (i i i) HYPOTHETICAL: N (i v) ANTI-SENSE: N (v i i) IMMEDIATE SOURCE:
      (B) CLONE: ZC906

(x i) SEQUENCE DESCRIPTION: SEQ ID NO:7:

AAGCTGTCCT CTGCTTCAGC CAGAGGTCCT GGGCAGCC          38

(2) INFORMATION FOR SEQ ID NO:8:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: N (iv) ANTI-SENSE: N (vii) IMMEDIATE SOURCE:
  (B) CLONE: ZC1380

(xi) SEQUENCE DESCRIPTION: SEQ ID NO:8:

CATGGTGGAA TTCCTGCTGA T    21

(2) INFORMATION FOR SEQ ID NO:9:

(i) SEQUENCE CHARACTERISTICS:
  (A) LENGTH: 29 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: N (iv) ANTI-SENSE: N (vii) IMMEDIATE SOURCE:
  (B) CLONE: ZC1447

(xi) SEQUENCE DESCRIPTION: SEQ ID NO:9:

TGGTTGTGCA GAGCTGAGGA AGAGATGGA    29

(2) INFORMATION FOR SEQ ID NO:10:

(i) SEQUENCE CHARACTERISTICS:
  (A) LENGTH: 55 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: N (iv) ANTI-SENSE: N (vii) IMMEDIATE SOURCE:
  (B) CLONE: ZC1453

(xi) SEQUENCE DESCRIPTION: SEQ ID NO:10:

AATTCATTAT GTTGTTGCAA GCCTTCTTGT TCCTGCTAGC TGGTTTCGCT GTTAA    55

(2) INFORMATION FOR SEQ ID NO:11:

(i) SEQUENCE CHARACTERISTICS:
  (A) LENGTH: 55 base pairs
  (B) TYPE: nucleic acid
  (C) STRANDEDNESS: single
  (D) TOPOLOGY: linear (ii) MOLECULE TYPE: Other nucleic acid (iii) HYPOTHETICAL: N (iv) ANTI-SENSE: N (vii) IMMEDIATE SOURCE:
  (B) CLONE: ZC1454

( x i ) SEQUENCE DESCRIPTION: SEQ ID NO:11:

GATCTTAACA GCGAAACCAG CTAGCAGGAA CAAGAAGGCT TGCAACAACA TAATG 55

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC1478

( x i ) SEQUENCE DESCRIPTION: SEQ ID NO:12:

ATCGCGAGCA TGCAGATCTG A 21

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC1479

( x i ) SEQUENCE DESCRIPTION: SEQ ID NO:13:

AGCTTCAGAT CTGCATGCTG CCGAT 25

( 2 ) INFORMATION FOR SEQ ID NO:14:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC1776

( x i ) SEQUENCE DESCRIPTION: SEQ ID NO:14:

AGCTGAGCGC AAATGTTGTG TCGAGTGCCC ACCGTGCCCA GCTTAGAATT CT 52

( 2 ) INFORMATION FOR SEQ ID NO:15:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
( B ) CLONE: ZC1777

( x i ) SEQUENCE DESCRIPTION: SEQ ID NO:15:

CTAGAGAATT CTAAGCTGGG CACGGTGGGC ACTCGACACA ACATTTGCGC TC    52

( 2 ) INFORMATION FOR SEQ ID NO:16:

( i ) SEQUENCE CHARACTERISTICS:
( A ) LENGTH: 95 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
( B ) CLONE: ZC1846

( x i ) SEQUENCE DESCRIPTION: SEQ ID NO:16:

GATCGGCCAC TGTCGGTGCG CTGCACGCTG CGCAACGCTG TGGGCCAGGA CACGCAGGAG    60

GTCATCGTGG TGCCACACTC CTTGCCCTTT AAGCA    95

( 2 ) INFORMATION FOR SEQ ID NO:17:

( i ) SEQUENCE CHARACTERISTICS:
( A ) LENGTH: 95 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
( B ) CLONE: ZC1847

( x i ) SEQUENCE DESCRIPTION: SEQ ID NO:17:

AGCTTGCTTA AAGGGCAAGG AGTGTGGCAC CACGATGACC TCCTGCGTGT CCTGGCCCAC    60

AGCGTTGCGC AGCGTGCAGC GCACCGACAG TGGCC    95

( 2 ) INFORMATION FOR SEQ ID NO:18:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
( B ) CLONE: ZC1886

( x i ) SEQUENCE DESCRIPTION: SEQ ID NO:18:

CCAGTGCCAA GCTTGTCTAG ACTTACCTTT AAAGGGCAAG GAG    43

( 2 ) INFORMATION FOR SEQ ID NO:19:

( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
            ( B ) CLONE: ZC1892

( x i ) SEQUENCE DESCRIPTION: SEQ ID NO:19:

AGCTTGAGCG T    11

( 2 ) INFORMATION FOR SEQ ID NO:20:

( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
            ( B ) CLONE: ZC1893

( x i ) SEQUENCE DESCRIPTION: SEQ ID NO:20:

CTAGACGCTC A    11

( 2 ) INFORMATION FOR SEQ ID NO:21:

( i ) SEQUENCE CHARACTERISTICS:
            ( A ) LENGTH: 47 base pairs
            ( B ) TYPE: nucleic acid
            ( C ) STRANDEDNESS: single
            ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
            ( B ) CLONE: ZC1894

( x i ) SEQUENCE DESCRIPTION: SEQ ID NO:21:

AGCTTCCAGT TCTTCGGCCT CATGTCAGTT CTTCGGCCTC ATGTGAT    47

( 2 ) INFORMATION FOR SEQ ID NO:22:

( i ) SEQUENCE CHARACTERISTICS:
            ( A ) LENGTH: 47 base pairs
            ( B ) TYPE: nucleic acid
            ( C ) STRANDEDNESS: single
            ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
  ( B ) CLONE: ZC1895

( x i ) SEQUENCE DESCRIPTION: SEQ ID NO:22:

CTAGATCACA TGAGGCCGAA GAACTGACAT GAGGCCGAAG AACTGGA      47

( 2 ) INFORMATION FOR SEQ ID NO:23:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
    ( B ) CLONE: ZC2181

( x i ) SEQUENCE DESCRIPTION: SEQ ID NO:23:

AATTCGGATC CACCATGGGC ACCAGCCACC CGGCGTTCCT GGTGTTAGGC TGCCTGCTGA    60

CCGGCC        66

( 2 ) INFORMATION FOR SEQ ID NO:24:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
    ( B ) CLONE: ZC2182

( x i ) SEQUENCE DESCRIPTION: SEQ ID NO:24:

TGAGCCTGAT CCTGTGCCAA CTGAGCCTGC CATCGATCCT GCCAAACGAG AACGAGAAGG    60

TTGTGCAGCT A        71

( 2 ) INFORMATION FOR SEQ ID NO:25:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
    ( B ) CLONE: ZC2183

( x i ) SEQUENCE DESCRIPTION: SEQ ID NO:25:

AATTTAGCTG CACAACCTTC TCGTTCTCGT TTGGCAGGAT CGATGGCAGG CTCAGTTGGC    60

ACAGGATCA 69

( 2 ) INFORMATION FOR SEQ ID NO:26:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC2184

( x i ) SEQUENCE DESCRIPTION: SEQ ID NO:26:

GGCTCAGGCC GGTCAGCAGG CAGCCTAACA CCAGGAACGC CGGGTGGCTG GTGCCCATGG 60

TGGATCCG 68

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC2311

( x i ) SEQUENCE DESCRIPTION: SEQ ID NO:27:

TGATCACCAT GGCTCAACTG 20

( 2 ) INFORMATION FOR SEQ ID NO:28:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
        ( B ) CLONE: ZC2351

( x i ) SEQUENCE DESCRIPTION: SEQ ID NO:28:

CGAATTCCAC 10

( 2 ) INFORMATION FOR SEQ ID NO:29:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
  ( B ) CLONE: ZC2352

( x i ) SEQUENCE DESCRIPTION: SEQ ID NO:29:

ATTATACGCA TGGTGGAATT CGAGCT 26

( 2 ) INFORMATION FOR SEQ ID NO:30:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: N ( i v ) ANTI-SENSE: N ( v i i ) IMMEDIATE SOURCE:
    ( B ) CLONE: ZC2392

( x i ) SEQUENCE DESCRIPTION: SEQ ID NO:30:

ACGTAAGCTT GTCTAGACTT ACCTTCAGAA CGCAGGGTGG G 41

( 2 ) INFORMATION FOR SEQ ID NO:31:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( v ) FRAGMENT TYPE: C-terminal ( v i i ) IMMEDIATE SOURCE:
    ( B ) CLONE: pWK1

( x i ) SEQUENCE DESCRIPTION: SEQ ID NO:31:

Ala Leu His Asn His Tyr Thr Glu Lys Ser Leu Ser Leu Ser Pro Gly
1               5                   10                  15

Lys ( 2 ) INFORMATION FOR SEQ ID NO:32:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid ( i i i ) HYPOTHETICAL: N ( i v ) ANTI-SENSE: N ( x i ) SEQUENCE DESCRIPTION: SEQ ID NO:32:

TGTGACACTC TCCTGGGAGT TA 22

( 2 ) INFORMATION FOR SEQ ID NO:33:

( i ) SEQUENCE CHARACTERISTICS:

(A) LENGTH: 30 base pairs
(B) TYPE: nucleic acid
(C) STRANDEDNESS: single
(D) TOPOLOGY: linear (ii) MOLECULE TYPE: Other nucleic acid (iii) HYPOTHETICAL: N (iv) ANTI-SENSE: N (xi) SEQUENCE DESCRIPTION: SEQ ID NO:33:

GCATAGTAGT TACCATATCC TCTTGCACAG                                                30

(2) INFORMATION FOR SEQ ID NO:34:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Other nucleic acid (iii) HYPOTHETICAL: N (iv) ANTI-SENSE: N (xi) SEQUENCE DESCRIPTION: SEQ ID NO:34:

ACCGAACGTG AGAGGAGTGC TATAA                                                     25

(2) INFORMATION FOR SEQ ID NO:35:

(i) SEQUENCE CHARACTERISTICS:
(A) LENGTH: 4054 base pairs
(B) TYPE: nucleic acid
(C) STRANDEDNESS: double
(D) TOPOLOGY: linear (ii) MOLECULE TYPE: cDNA (iii) HYPOTHETICAL: N (iv) ANTI-SENSE: N (vi) ORIGINAL SOURCE:
(A) ORGANISM: Homo sapiens (vii) IMMEDIATE SOURCE:
(B) CLONE: p-alpha-17B (ix) FEATURE:
(A) NAME/KEY: CDS
(B) LOCATION: 205..3471
(D) OTHER INFORMATION:

(xi) SEQUENCE DESCRIPTION: SEQ ID NO:35:

| GCCCTGGGGA | CGGACCGTGG | GCGGCGCGCA | GCGGCGGGAC | GCGTTTTGGG | GACGTGGTGG | 60 |

| CCAGCGCCTT | CCTGCAGACC | CACAGGGAAG | TACTCCCTTT | GACCTCCGGG | GAGCTGCGAC | 120 |

| CAGGTTATAC | GTTGCTGGTG | GAAAAGTGAC | AATTCTAGGA | AAAGAGCTAA | AAGCCGGATC | 180 |

GGTGACCGAA AGTTTCCCAG AGCT ATG GGG ACT TCC CAT CCG GCG TTC CTG                  231
                            Met Gly Thr Ser His Pro Ala Phe Leu
                             1               5

GTC TTA GGC TGT CTT CTC ACA GGG CTG AGC CTA ATC CTC TGC AGC TTC                 279
Val Leu Gly Cys Leu Leu Thr Gly Leu Ser Leu Ile Leu Cys Gln Leu
 10              15                  20                  25

TCA TTA CCC TCT ATC CTT CCA AAT GAA AAT GAA AAG GTT GTG CAG CTG                 327
Ser Leu Pro Ser Ile Leu Pro Asn Glu Asn Glu Lys Val Val Gln Leu
             30                  35                  40

| | | | | | | | | | | | | | | | | |
|---|---|---|---|---|---|---|---|---|---|---|---|---|---|---|---|---|
| AAT | TCA | TCC | TTT | TCT | CTG | AGA | TGC | TTT | GGG | GAG | AGT | GAA | GTG | AGC | TGG | 375 |
| Asn | Ser | Ser | Phe | Ser | Leu | Arg | Cys | Phe | Gly | Glu | Ser | Glu | Val | Ser | Trp | |
| | | | 45 | | | | 50 | | | | | 55 | | | | |
| CAG | TAC | CCC | ATG | TCT | GAA | GAA | GAG | AGC | TCC | GAT | GTG | GAA | ATC | AGA | AAT | 423 |
| Gln | Tyr | Pro | Met | Ser | Glu | Glu | Glu | Ser | Ser | Asp | Val | Glu | Ile | Arg | Asn | |
| | | 60 | | | | | 65 | | | | | 70 | | | | |
| GAA | GAA | AAC | AAC | AGC | GGC | CTT | TTT | GTG | ACG | GTC | TTG | GAA | GTG | AGC | AGT | 471 |
| Glu | Glu | Asn | Asn | Ser | Gly | Leu | Phe | Val | Thr | Val | Leu | Glu | Val | Ser | Ser | |
| | 75 | | | | | 80 | | | | | 85 | | | | | |
| GCC | TCG | GCG | GCC | CAC | ACA | GGG | TTG | TAC | ACT | TGC | TAT | TAC | AAC | CAC | ACT | 519 |
| Ala | Ser | Ala | Ala | His | Thr | Gly | Leu | Tyr | Thr | Cys | Tyr | Tyr | Asn | His | Thr | |
| 90 | | | | | 95 | | | | | 100 | | | | | 105 | |
| CAG | ACA | GAA | GAG | AAT | GAG | CTT | GAA | GGC | AGG | CAC | ATT | TAC | ATC | TAT | GTG | 567 |
| Gln | Thr | Glu | Glu | Asn | Glu | Leu | Glu | Gly | Arg | His | Ile | Tyr | Ile | Tyr | Val | |
| | | | | 110 | | | | | 115 | | | | | 120 | | |
| CCA | GAC | CCA | GAT | GTA | GCC | TTT | GTA | CCT | CTA | GGA | ATG | ACG | GAT | TAT | TTA | 615 |
| Pro | Asp | Pro | Asp | Val | Ala | Phe | Val | Pro | Leu | Gly | Met | Thr | Asp | Tyr | Leu | |
| | | | 125 | | | | | 130 | | | | | 135 | | | |
| GTC | ATC | GTG | GAG | GAT | GAT | GAT | TCT | GCC | ATT | ATA | CCT | TGT | CGC | ACA | ACT | 663 |
| Val | Ile | Val | Glu | Asp | Asp | Asp | Ser | Ala | Ile | Ile | Pro | Cys | Arg | Thr | Thr | |
| | | 140 | | | | | 145 | | | | | 150 | | | | |
| GAT | CCC | GAG | ACT | CCT | GTA | ACC | TTA | CAC | AAC | AGT | GAG | GGG | GTG | GTA | CCT | 711 |
| Asp | Pro | Glu | Thr | Pro | Val | Thr | Leu | His | Asn | Ser | Glu | Gly | Val | Val | Pro | |
| | 155 | | | | | 160 | | | | | 165 | | | | | |
| GCC | TCC | TAC | GAC | AGC | AGA | CAG | GGC | TTT | AAT | GGG | ACC | TTC | ACT | GTA | GGG | 759 |
| Ala | Ser | Tyr | Asp | Ser | Arg | Gln | Gly | Phe | Asn | Gly | Thr | Phe | Thr | Val | Gly | |
| 170 | | | | | 175 | | | | | 180 | | | | | 185 | |
| CCC | TAT | ATC | TGT | GAG | GCC | ACC | GTC | AAA | GGA | AAG | AAG | TTC | CAG | ACC | ATC | 807 |
| Pro | Tyr | Ile | Cys | Glu | Ala | Thr | Val | Lys | Gly | Lys | Lys | Phe | Gln | Thr | Ile | |
| | | | | 190 | | | | | 195 | | | | | 200 | | |
| CCA | TTT | AAT | GTT | TAT | GCT | TTA | AAA | GCA | ACA | TCA | GAG | CTG | GAT | CTA | GAA | 855 |
| Pro | Phe | Asn | Val | Tyr | Ala | Leu | Lys | Ala | Thr | Ser | Glu | Leu | Asp | Leu | Glu | |
| | | | 205 | | | | | 210 | | | | | 215 | | | |
| ATG | GAA | GCT | CTT | AAA | ACC | GTG | TAT | AAG | TCA | GGG | GAA | ACG | ATT | GTG | GTC | 903 |
| Met | Glu | Ala | Leu | Lys | Thr | Val | Tyr | Lys | Ser | Gly | Glu | Thr | Ile | Val | Val | |
| | | | 220 | | | | | 225 | | | | | 230 | | | |
| ACC | TGT | GCT | GTT | TTT | AAC | AAT | GAG | GTG | GTT | GAC | CTT | CAA | TGG | ACT | TAC | 951 |
| Thr | Cys | Ala | Val | Phe | Asn | Asn | Glu | Val | Val | Asp | Leu | Gln | Trp | Thr | Tyr | |
| | | 235 | | | | | 240 | | | | | 245 | | | | |
| CCT | GGA | GAA | GTG | AAA | GGC | AAA | GGC | ATC | ACA | ATA | CTG | GAA | GAA | ATC | AAA | 999 |
| Pro | Gly | Glu | Val | Lys | Gly | Lys | Gly | Ile | Thr | Ile | Leu | Glu | Glu | Ile | Lys | |
| 250 | | | | | 255 | | | | | 260 | | | | | 265 | |
| GTC | CCA | TCC | ATC | AAA | TTG | GTG | TAC | ACT | TTG | ACG | GTC | CCC | GAG | GCC | ACG | 1047 |
| Val | Pro | Ser | Ile | Lys | Leu | Val | Tyr | Thr | Leu | Thr | Val | Pro | Glu | Ala | Thr | |
| | | | | 270 | | | | | 275 | | | | | 280 | | |
| GTG | AAA | GAC | AGT | GGA | GAT | TAC | GAA | TGT | GCT | GCC | CGC | CAG | GCT | ACC | AGG | 1095 |
| Val | Lys | Asp | Ser | Gly | Asp | Tyr | Glu | Cys | Ala | Ala | Arg | Gln | Ala | Thr | Arg | |
| | | | 285 | | | | | 290 | | | | | 295 | | | |
| GAG | GTC | AAA | GAA | ATG | AAG | AAA | GTC | ACT | ATT | TCT | GTC | CAT | GAG | AAA | GGT | 1143 |
| Glu | Val | Lys | Glu | Met | Lys | Lys | Val | Thr | Ile | Ser | Val | His | Glu | Lys | Gly | |
| | | 300 | | | | | 305 | | | | | 310 | | | | |
| TTC | ATT | GAA | ATC | AAA | CCC | ACC | TTC | AGC | CAG | TTG | GAA | GCT | GTC | AAC | CTG | 1191 |
| Phe | Ile | Glu | Ile | Lys | Pro | Thr | Phe | Ser | Gln | Leu | Glu | Ala | Val | Asn | Leu | |
| | 315 | | | | | 320 | | | | | 325 | | | | | |
| CAT | GAA | GTC | AAA | CAT | TTT | GTT | GTA | GAG | GTG | CGG | GCC | TAC | CCA | CCT | CCC | 1239 |
| His | Glu | Val | Lys | His | Phe | Val | Val | Glu | Val | Arg | Ala | Tyr | Pro | Pro | Pro | |
| 330 | | | | | 335 | | | | | 340 | | | | | 345 | |
| AGG | ATA | TCC | TGG | CTG | AAA | AAC | AAT | CTG | ACT | CTG | ATT | GAA | AAT | CTC | ACT | 1287 |
| Arg | Ile | Ser | Trp | Leu | Lys | Asn | Asn | Leu | Thr | Leu | Ile | Glu | Asn | Leu | Thr | |
| | | | | 350 | | | | | 355 | | | | | 360 | | |

| | | | | | | | | | | | | | | | | |
|---|---|---|---|---|---|---|---|---|---|---|---|---|---|---|---|---|
| GAG | ATC | ACC | ACT | GAT | GTG | GAA | AAG | ATT | CAG | GAA | ATA | AGG | TAT | CGA | AGC | 1335 |
| Glu | Ile | Thr | Thr | Asp | Val | Glu | Lys | Ile | Gln | Glu | Ile | Arg | Tyr | Arg | Ser | |
| | | | 365 | | | | 370 | | | | | 375 | | | | |
| AAA | TTA | AAG | CTG | ATC | CGT | GCT | AAG | GAA | GAA | GAC | AGT | GGC | CAT | TAT | ACT | 1383 |
| Lys | Leu | Lys | Leu | Ile | Arg | Ala | Lys | Glu | Glu | Asp | Ser | Gly | His | Tyr | Thr | |
| | | 380 | | | | | 385 | | | | | 390 | | | | |
| ATT | GTA | GCT | CAA | AAT | GAA | GAT | GCT | GTG | AAG | AGC | TAT | ACT | TTT | GAA | CTG | 1431 |
| Ile | Val | Ala | Gln | Asn | Glu | Asp | Ala | Val | Lys | Ser | Tyr | Thr | Phe | Glu | Leu | |
| 395 | | | | | 400 | | | | | | 405 | | | | | |
| TTA | ACT | CAA | GTT | CCT | TCA | TCC | ATT | CTG | GAC | TTG | GTC | GAT | GAT | CAC | CAT | 1479 |
| Leu | Thr | Gln | Val | Pro | Ser | Ser | Ile | Leu | Asp | Leu | Val | Asp | Asp | His | His | |
| 410 | | | | | 415 | | | | 420 | | | | | | 425 | |
| GGC | TCA | ACT | GGG | GGA | CAG | ACG | GTG | AGG | TGC | ACA | GCT | GAA | GGC | ACG | CCG | 1527 |
| Gly | Ser | Thr | Gly | Gly | Gln | Thr | Val | Arg | Cys | Thr | Ala | Glu | Gly | Thr | Pro | |
| | | | | 430 | | | | | 435 | | | | | 440 | | |
| CTT | CCT | GAT | ATT | GAG | TGG | ATG | ATA | TGC | AAA | GAT | ATT | AAG | AAA | TGT | AAT | 1575 |
| Leu | Pro | Asp | Ile | Glu | Trp | Met | Ile | Cys | Lys | Asp | Ile | Lys | Lys | Cys | Asn | |
| | | | 445 | | | | | 450 | | | | 455 | | | | |
| AAT | GAA | ACT | TCC | TGG | ACT | ATT | TTG | GCC | AAC | AAT | GTC | TCA | AAC | ATC | ATC | 1623 |
| Asn | Glu | Thr | Ser | Trp | Thr | Ile | Leu | Ala | Asn | Asn | Val | Ser | Asn | Ile | Ile | |
| | | 460 | | | | | 465 | | | | | 470 | | | | |
| ACG | GAG | ATC | CAC | TCC | CGA | GAC | AGG | AGT | ACC | GTG | GAG | GGC | CGT | GTG | ACT | 1671 |
| Thr | Glu | Ile | His | Ser | Arg | Asp | Arg | Ser | Thr | Val | Glu | Gly | Arg | Val | Thr | |
| | 475 | | | | | 480 | | | | | 485 | | | | | |
| TTC | GCC | AAA | GTG | GAG | GAG | ACC | ATC | GCC | GTG | CGA | TGC | CTG | GCT | AAG | AAT | 1719 |
| Phe | Ala | Lys | Val | Glu | Glu | Thr | Ile | Ala | Val | Arg | Cys | Leu | Ala | Lys | Asn | |
| 490 | | | | | 495 | | | | | 500 | | | | | 505 | |
| CTC | CTT | GGA | GCT | GAG | AAC | CGA | GAG | CTG | AAG | CTG | GTG | GCT | CCC | ACC | CTG | 1767 |
| Leu | Leu | Gly | Ala | Glu | Asn | Arg | Glu | Leu | Lys | Leu | Val | Ala | Pro | Thr | Leu | |
| | | | | 510 | | | | | 515 | | | | | 520 | | |
| CGT | TCT | GAA | CTC | ACG | GTG | GCT | GCT | GCA | GTC | CTG | GTG | CTG | TTG | GTG | ATT | 1815 |
| Arg | Ser | Glu | Leu | Thr | Val | Ala | Ala | Ala | Val | Leu | Val | Leu | Leu | Val | Ile | |
| | | | | 525 | | | | 530 | | | | | 535 | | | |
| GTG | ATC | ATC | TCA | CTT | ATT | GTC | CTG | GTT | GTC | ATT | TGG | AAA | CAG | AAA | CCG | 1863 |
| Val | Ile | Ile | Ser | Leu | Ile | Val | Leu | Val | Val | Ile | Trp | Lys | Gln | Lys | Pro | |
| | | | 540 | | | | | 545 | | | | | 550 | | | |
| AGG | TAT | GAA | ATT | CGC | TGG | AGG | GTC | ATT | GAA | TCA | ATC | AGC | CCG | GAT | GGA | 1911 |
| Arg | Tyr | Glu | Ile | Arg | Trp | Arg | Val | Ile | Glu | Ser | Ile | Ser | Pro | Asp | Gly | |
| | 555 | | | | | 560 | | | | | 565 | | | | | |
| CAT | GAA | TAT | ATT | TAT | GTG | GAC | CCG | ATG | CAG | CTG | CCT | TAT | GAC | TCA | AGA | 1959 |
| His | Glu | Tyr | Ile | Tyr | Val | Asp | Pro | Met | Gln | Leu | Pro | Tyr | Asp | Ser | Arg | |
| 570 | | | | | 575 | | | | | 580 | | | | | 585 | |
| TGG | GAG | TTT | CCA | AGA | GAT | GGA | CTA | GTG | CTT | GGT | CGG | GTC | TTG | GGG | TCT | 2007 |
| Trp | Glu | Phe | Pro | Arg | Asp | Gly | Leu | Val | Leu | Gly | Arg | Val | Leu | Gly | Ser | |
| | | | | 590 | | | | 595 | | | | | 600 | | | |
| GGA | GCG | TTT | GGG | AAG | GTG | GTT | GAA | GGA | ACA | GCC | TAT | GGA | TTA | AGC | CGG | 2055 |
| Gly | Ala | Phe | Gly | Lys | Val | Val | Glu | Gly | Thr | Ala | Tyr | Gly | Leu | Ser | Arg | |
| | | | 605 | | | | | 610 | | | | | 615 | | | |
| TCC | CAA | CCT | GTC | ATG | AAA | GTT | GCA | GTG | AAG | ATG | CTA | AAA | CCC | ACG | GCC | 2103 |
| Ser | Gln | Pro | Val | Met | Lys | Val | Ala | Val | Lys | Met | Leu | Lys | Pro | Thr | Ala | |
| | | 620 | | | | | 625 | | | | | 630 | | | | |
| AGA | TCC | AGT | GAA | AAA | CAA | GCT | CTC | ATG | TCT | GAA | CTG | AAG | ATA | ATG | ACT | 2151 |
| Arg | Ser | Ser | Glu | Lys | Gln | Ala | Leu | Met | Ser | Glu | Leu | Lys | Ile | Met | Thr | |
| | 635 | | | | | 640 | | | | | 645 | | | | | |
| CAC | CTG | GGG | CCA | CAT | TTG | AAC | ATT | GTA | AAC | TTG | CTG | GGA | GCC | TGC | ACC | 2199 |
| His | Leu | Gly | Pro | His | Leu | Asn | Ile | Val | Asn | Leu | Leu | Gly | Ala | Cys | Thr | |
| 650 | | | | | 655 | | | | | 660 | | | | | 665 | |
| AAG | TCA | GGC | CCC | ATT | TAC | ATC | ATC | ACA | GAG | TAT | TGC | TTC | TAT | GGA | GAT | 2247 |
| Lys | Ser | Gly | Pro | Ile | Tyr | Ile | Ile | Thr | Glu | Tyr | Cys | Phe | Tyr | Gly | Asp | |
| | | | | 670 | | | | | 675 | | | | | 680 | | |

```
TTG  GTC  AAC  TAT  TTG  CAT  AAG  AAT  AGG  GAT  AGC  TTC  CTG  AGC  CAC  CAC   2295
Leu  Val  Asn  Tyr  Leu  His  Lys  Asn  Arg  Asp  Ser  Phe  Leu  Ser  His  His
               685                 690                      695

CCA  GAG  AAG  CCA  AAG  AAA  GAG  CTG  GAT  ATC  TTT  GGA  TTG  AAC  CCT  GCT   2343
Pro  Glu  Lys  Pro  Lys  Lys  Glu  Leu  Asp  Ile  Phe  Gly  Leu  Asn  Pro  Ala
          700                      705                      710

GAT  GAA  AGC  ACA  CGG  AGC  TAT  GTT  ATT  TTA  TCT  TTT  GAA  AAC  AAT  GGT   2391
Asp  Glu  Ser  Thr  Arg  Ser  Tyr  Val  Ile  Leu  Ser  Phe  Glu  Asn  Asn  Gly
     715                           720                      725

GAC  TAC  ATG  GAC  ATG  AAG  CAG  GCT  GAT  ACT  ACA  CAG  TAT  GTC  CCC  ATG   2439
Asp  Tyr  Met  Asp  Met  Lys  Gln  Ala  Asp  Thr  Thr  Gln  Tyr  Val  Pro  Met
730                      735                      740                      745

CTA  GAA  AGG  AAA  GAG  GTT  TCT  AAA  TAT  TCC  GAC  ATC  CAG  AGA  TCA  CTC   2487
Leu  Glu  Arg  Lys  Glu  Val  Ser  Lys  Tyr  Ser  Asp  Ile  Gln  Arg  Ser  Leu
                    750                      755                      760

TAT  GAT  CGT  CCA  GCC  TCA  TAT  AAG  AAG  AAA  TCT  ATG  TTA  GAC  TCA  GAA   2535
Tyr  Asp  Arg  Pro  Ala  Ser  Tyr  Lys  Lys  Lys  Ser  Met  Leu  Asp  Ser  Glu
               765                      770                      775

GTC  AAA  AAC  CTC  CTT  TCA  GAT  GAT  AAC  TCA  GAA  GGC  CTT  ACT  TTA  TTG   2583
Val  Lys  Asn  Leu  Leu  Ser  Asp  Asp  Asn  Ser  Glu  Gly  Leu  Thr  Leu  Leu
          780                      785                      790

GAT  TTG  TTG  AGC  TTC  ACC  TAT  CAA  GTT  GCC  CGA  GGA  ATG  GAG  TTT  TTG   2631
Asp  Leu  Leu  Ser  Phe  Thr  Tyr  Gln  Val  Ala  Arg  Gly  Met  Glu  Phe  Leu
     795                           800                      805

GCT  TCA  AAA  AAT  TGT  GTC  CAC  CGT  GAT  CTG  GCT  GCT  CGC  AAC  GTC  CTC   2679
Ala  Ser  Lys  Asn  Cys  Val  His  Arg  Asp  Leu  Ala  Ala  Arg  Asn  Val  Leu
810                      815                      820                      825

CTG  GCA  CAA  GGA  AAA  ATT  GTG  AAG  ATC  TGT  GAC  TTT  GGC  CTG  GCC  AGA   2727
Leu  Ala  Gln  Gly  Lys  Ile  Val  Lys  Ile  Cys  Asp  Phe  Gly  Leu  Ala  Arg
                    830                      835                      840

GAC  ATC  ATG  CAT  GAT  TCG  AAC  TAT  GTG  TCG  AAA  GGC  AGT  ACC  TTT  CTG   2775
Asp  Ile  Met  His  Asp  Ser  Asn  Tyr  Val  Ser  Lys  Gly  Ser  Thr  Phe  Leu
               845                      850                      855

CCC  GTG  AAG  TGG  ATG  GCT  CCT  GAG  AGC  ATC  TTT  GAC  AAC  CTC  TAC  ACC   2823
Pro  Val  Lys  Trp  Met  Ala  Pro  Glu  Ser  Ile  Phe  Asp  Asn  Leu  Tyr  Thr
          860                      865                      870

ACA  CTG  AGT  GAT  GTC  TGG  TCT  TAT  GGC  ATT  CTG  CTC  TGG  GAG  ATC  TTT   2871
Thr  Leu  Ser  Asp  Val  Trp  Ser  Tyr  Gly  Ile  Leu  Leu  Trp  Glu  Ile  Phe
875                      880                      885

TCC  CTT  GGT  GGC  ACC  CCT  TAC  CCC  GGC  ATG  ATG  GTG  GAT  TCT  ACT  TTC   2919
Ser  Leu  Gly  Gly  Thr  Pro  Tyr  Pro  Gly  Met  Met  Val  Asp  Ser  Thr  Phe
890                      895                      900                      905

TAC  AAT  AAG  ATC  AAG  AGT  GGG  TAC  CGG  ATG  GCC  AAG  CCT  GAC  CAC  GCT   2967
Tyr  Asn  Lys  Ile  Lys  Ser  Gly  Tyr  Arg  Met  Ala  Lys  Pro  Asp  His  Ala
               910                      915                      920

ACC  AGT  GAA  GTC  TAC  GAG  ATC  ATG  GTG  AAA  TGC  TGG  AAC  AGT  GAG  CCG   3015
Thr  Ser  Glu  Val  Tyr  Glu  Ile  Met  Val  Lys  Cys  Trp  Asn  Ser  Glu  Pro
          925                      930                      935

GAG  AAG  AGA  CCC  TCC  TTT  TAC  CAC  CTG  AGT  GAG  ATT  GTG  GAG  AAT  CTG   3063
Glu  Lys  Arg  Pro  Ser  Phe  Tyr  His  Leu  Ser  Glu  Ile  Val  Glu  Asn  Leu
          940                      945                      950

CTG  CCT  GGA  CAA  TAT  AAA  AAG  AGT  TAT  GAA  AAA  ATT  CAC  CTG  GAC  TTC   3111
Leu  Pro  Gly  Gln  Tyr  Lys  Lys  Ser  Tyr  Glu  Lys  Ile  His  Leu  Asp  Phe
     955                      960                      965

CTG  AAG  AGT  GAC  CAT  CCT  GCT  GTG  GCA  CGC  ATG  CGT  GTG  GAC  TCA  GAC   3159
Leu  Lys  Ser  Asp  His  Pro  Ala  Val  Ala  Arg  Met  Arg  Val  Asp  Ser  Asp
970                      975                      980                      985

AAT  GCA  TAC  ATT  GGT  GTC  ACC  TAC  AAA  AAC  GAG  GAA  GAC  AAG  CTG  AAG   3207
Asn  Ala  Tyr  Ile  Gly  Val  Thr  Tyr  Lys  Asn  Glu  Glu  Asp  Lys  Leu  Lys
                    990                      995                      1000
```

| | | | | | | | | | | | | | | | | |
|---|---|---|---|---|---|---|---|---|---|---|---|---|---|---|---|---|
| GAC | TGG | GAG | GGT | GGT | CTG | GAT | GAG | CAG | AGA | CTG | AGC | GCT | GAC | AGT | GGC | 3255 |
| Asp | Trp | Glu | Gly | Gly | Leu | Asp | Glu | Gln | Arg | Leu | Ser | Ala | Asp | Ser | Gly | |
| | | | 1005 | | | | | 1010 | | | | | 1015 | | | |
| TAC | ATC | ATT | CCT | CTG | CCT | GAC | ATT | GAC | CCT | GTC | CCT | GAG | GAG | GAG | GAC | 3303 |
| Tyr | Ile | Ile | Pro | Leu | Pro | Asp | Ile | Asp | Pro | Val | Pro | Glu | Glu | Glu | Asp | |
| | | 1020 | | | | | 1025 | | | | | 1030 | | | | |
| CTG | GGC | AAG | AGG | AAC | AGA | CAC | AGC | TCG | CAG | ACC | TCT | GAA | GAG | AGT | GCC | 3351 |
| Leu | Gly | Lys | Arg | Asn | Arg | His | Ser | Ser | Gln | Thr | Ser | Glu | Glu | Ser | Ala | |
| | 1035 | | | | | 1040 | | | | | 1045 | | | | | |
| ATT | GAG | ACG | GGT | TCC | AGC | AGT | TCC | ACC | TTC | ATC | AAG | AGA | GAG | GAC | GAG | 3399 |
| Ile | Glu | Thr | Gly | Ser | Ser | Ser | Ser | Thr | Phe | Ile | Lys | Arg | Glu | Asp | Glu | |
| 1050 | | | | | 1055 | | | | | 1060 | | | | | 1065 | |
| ACC | ATT | GAA | GAC | ATC | GAC | ATG | ATG | GAC | GAC | ATC | GGC | ATA | GAC | TCT | TCA | 3447 |
| Thr | Ile | Glu | Asp | Ile | Asp | Met | Met | Asp | Asp | Ile | Gly | Ile | Asp | Ser | Ser | |
| | | | | 1070 | | | | | 1075 | | | | | 1080 | | |
| GAC | CTG | GTG | GAA | GAC | AGC | TTC | CTG | TAACTGGCGG | | ATTCGAGGGG | | TTCCTTCCAC | | | | 3501 |
| Asp | Leu | Val | Glu | Asp | Ser | Phe | Leu | | | | | | | | | |
| | | | | 1085 | | | | | | | | | | | | |

| | | | | | |
|---|---|---|---|---|---|
| TTCTGGGGCC | ACCTCTGGAT | CCCGTTCAGA | AAACCACTTT | ATTGCAATGC | GGAGGTTGAG | 3561 |
| AGGAGGACTT | GGTTGATGTT | TAAAGAGAAG | TTCCCAGCCA | AGGGCCTCGG | GGAGCGTTCT | 3621 |
| AAATATGAAT | GAATGGGATA | TTTTGAAATG | AACTTTGTCA | GTGTTGCCTC | TTGCAATGCC | 3681 |
| TCAGTAGCAT | CTCAGTGGTG | TGTGAAGTTT | GGAGATAGAT | GGATAAGGGA | ATAATAGGCC | 3741 |
| ACAGAAGGTG | AACTTTGTGC | TTCAAGGACA | TTGGTGAGAG | TCCAACAGAC | ACAATTTATA | 3801 |
| CTGCGACAGA | ACTTCAGCAT | TGTAATTATG | TAAATAACTC | TAACCAAGGC | TGTGTTTAGA | 3861 |
| TTGTATTAAC | TATCTTCTTT | GGACTTCTGA | AGAGACCACT | CAATCCATCC | TGTACTTCCC | 3921 |
| TCTTGAAACC | TGATGTAGCT | GCTGTTGAAC | TTTTTAAAGA | AGTGCATGAA | AAACCATTTT | 3981 |
| TGAACCTTAA | AAGGTACTGG | TACTATAGCA | TTTTGCTATC | TTTTTTAGTG | TTAAAGAGAT | 4041 |
| AAAGAATAAT | AAG | | | | | 4054 |

( 2 ) INFORMATION FOR SEQ ID NO:36:

( i ) SEQUENCE CHARACTERISTICS:
        ( A ) LENGTH: 1089 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| | | | | | | | | | | | | | | |
|---|---|---|---|---|---|---|---|---|---|---|---|---|---|---|
| Met | Gly | Thr | Ser | His | Pro | Ala | Phe | Leu | Val | Leu | Gly | Cys | Leu | Leu | Thr |
| 1 | | | | 5 | | | | | 10 | | | | | 15 | |
| Gly | Leu | Ser | Leu | Ile | Leu | Cys | Gln | Leu | Ser | Leu | Pro | Ser | Ile | Leu | Pro |
| | | | 20 | | | | 25 | | | | | 30 | | | |
| Asn | Glu | Asn | Glu | Lys | Val | Val | Gln | Leu | Asn | Ser | Ser | Phe | Ser | Leu | Arg |
| | | | 35 | | | | 40 | | | | | 45 | | | |
| Cys | Phe | Gly | Glu | Ser | Glu | Val | Ser | Trp | Gln | Tyr | Pro | Met | Ser | Glu | Glu |
| | 50 | | | | | 55 | | | | | 60 | | | | |
| Glu | Ser | Ser | Asp | Val | Glu | Ile | Arg | Asn | Glu | Glu | Asn | Asn | Ser | Gly | Leu |
| 65 | | | | | 70 | | | | | 75 | | | | | 80 |
| Phe | Val | Thr | Val | Leu | Glu | Val | Ser | Ser | Ala | Ser | Ala | Ala | His | Thr | Gly |
| | | | | 85 | | | | | 90 | | | | | 95 | |
| Leu | Tyr | Thr | Cys | Tyr | Tyr | Asn | His | Thr | Gln | Thr | Glu | Glu | Asn | Glu | Leu |
| | | | 100 | | | | 105 | | | | | 110 | | | |
| Glu | Gly | Arg | His | Ile | Tyr | Ile | Tyr | Val | Pro | Asp | Pro | Asp | Val | Ala | Phe |
| | | 115 | | | | 120 | | | | | 125 | | | | |

| | | | | | | | | | | | | | |
|---|---|---|---|---|---|---|---|---|---|---|---|---|---|
| Val | Pro | Leu | Gly | Met | Thr | Asp | Tyr | Leu | Val | Ile | Val | Glu | Asp | Asp | Asp |
| | 130 | | | | 135 | | | | 140 | | | | |
| Ser | Ala | Ile | Ile | Pro | Cys | Arg | Thr | Thr | Asp | Pro | Glu | Thr | Pro | Val | Thr |
| 145 | | | | | 150 | | | | 155 | | | | | | 160 |
| Leu | His | Asn | Ser | Gly | Val | Val | Pro | Ala | Ser | Tyr | Asp | Ser | Arg | Gln |
| | | | | 165 | | | | 170 | | | | | 175 | |
| Gly | Phe | Asn | Gly | Thr | Phe | Thr | Val | Gly | Pro | Tyr | Ile | Cys | Glu | Ala | Thr |
| | | | 180 | | | | | 185 | | | | | 190 | | |
| Val | Lys | Gly | Lys | Lys | Phe | Gln | Thr | Ile | Pro | Phe | Asn | Val | Tyr | Ala | Leu |
| | | 195 | | | | | 200 | | | | | 205 | | | |
| Lys | Ala | Thr | Ser | Glu | Leu | Asp | Leu | Glu | Met | Glu | Ala | Leu | Lys | Thr | Val |
| | 210 | | | | | 215 | | | | | 220 | | | | |
| Tyr | Lys | Ser | Gly | Glu | Thr | Ile | Val | Val | Thr | Cys | Ala | Val | Phe | Asn | Asn |
| 225 | | | | | 230 | | | | | 235 | | | | | 240 |
| Glu | Val | Val | Asp | Leu | Gln | Trp | Thr | Tyr | Pro | Gly | Glu | Val | Lys | Gly | Lys |
| | | | | 245 | | | | | 250 | | | | | 255 | |
| Gly | Ile | Thr | Ile | Leu | Glu | Glu | Ile | Lys | Val | Pro | Ser | Ile | Lys | Leu | Val |
| | | | 260 | | | | | 265 | | | | | 270 | | |
| Tyr | Thr | Leu | Thr | Val | Pro | Glu | Ala | Thr | Val | Lys | Asp | Ser | Gly | Asp | Tyr |
| | | 275 | | | | | 280 | | | | | 285 | | | |
| Glu | Cys | Ala | Ala | Arg | Gln | Ala | Thr | Arg | Glu | Val | Lys | Glu | Met | Lys | Lys |
| | 290 | | | | | 295 | | | | | 300 | | | | |
| Val | Thr | Ile | Ser | Val | His | Glu | Lys | Gly | Phe | Ile | Glu | Ile | Lys | Pro | Thr |
| 305 | | | | | 310 | | | | | 315 | | | | | 320 |
| Phe | Ser | Gln | Leu | Glu | Ala | Val | Asn | Leu | His | Glu | Val | Lys | His | Phe | Val |
| | | | | 325 | | | | | 330 | | | | | 335 | |
| Val | Glu | Val | Arg | Ala | Tyr | Pro | Pro | Pro | Arg | Ile | Ser | Trp | Leu | Lys | Asn |
| | | | 340 | | | | | 345 | | | | | 350 | | |
| Asn | Leu | Thr | Leu | Ile | Glu | Asn | Leu | Thr | Glu | Ile | Thr | Thr | Asp | Val | Glu |
| | | 355 | | | | | 360 | | | | | 365 | | | |
| Lys | Ile | Gln | Glu | Ile | Arg | Tyr | Arg | Ser | Lys | Leu | Lys | Leu | Ile | Arg | Ala |
| | 370 | | | | | 375 | | | | | 380 | | | | |
| Lys | Glu | Glu | Asp | Ser | Gly | His | Tyr | Thr | Ile | Val | Ala | Gln | Asn | Glu | Asp |
| 385 | | | | | 390 | | | | | 395 | | | | | 400 |
| Ala | Val | Lys | Ser | Tyr | Thr | Phe | Glu | Leu | Leu | Thr | Gln | Val | Pro | Ser | Ser |
| | | | | 405 | | | | | 410 | | | | | 415 | |
| Ile | Leu | Asp | Leu | Val | Asp | Asp | His | His | Gly | Ser | Thr | Gly | Gly | Gln | Thr |
| | | | 420 | | | | | 425 | | | | | 430 | | |
| Val | Arg | Cys | Thr | Ala | Glu | Gly | Thr | Pro | Leu | Pro | Asp | Ile | Glu | Trp | Met |
| | | 435 | | | | | 440 | | | | | 445 | | | |
| Ile | Cys | Lys | Asp | Ile | Lys | Lys | Cys | Asn | Asn | Glu | Thr | Ser | Trp | Thr | Ile |
| | 450 | | | | | 455 | | | | | 460 | | | | |
| Leu | Ala | Asn | Asn | Val | Ser | Asn | Ile | Ile | Thr | Glu | Ile | His | Ser | Arg | Asp |
| 465 | | | | | 470 | | | | | 475 | | | | | 480 |
| Arg | Ser | Thr | Val | Glu | Gly | Arg | Val | Thr | Phe | Ala | Lys | Val | Glu | Glu | Thr |
| | | | | 485 | | | | | 490 | | | | | 495 | |
| Ile | Ala | Val | Arg | Cys | Leu | Ala | Lys | Asn | Leu | Leu | Gly | Ala | Glu | Asn | Arg |
| | | | 500 | | | | | 505 | | | | | 510 | | |
| Glu | Leu | Lys | Leu | Val | Ala | Pro | Thr | Leu | Arg | Ser | Glu | Leu | Thr | Val | Ala |
| | | 515 | | | | | 520 | | | | | 525 | | | |
| Ala | Ala | Val | Leu | Val | Leu | Leu | Val | Ile | Val | Ile | Ile | Ser | Leu | Ile | Val |
| | 530 | | | | | 535 | | | | | 540 | | | | |
| Leu | Val | Val | Ile | Trp | Lys | Gln | Lys | Pro | Arg | Tyr | Glu | Ile | Arg | Trp | Arg |
| 545 | | | | | 550 | | | | | 555 | | | | | 560 |

| | | | | | | | | | | | | | | |
|---|---|---|---|---|---|---|---|---|---|---|---|---|---|---|
| Val | Ile | Glu | Ser | Ile | Ser | Pro | Asp | Gly | His | Glu | Tyr | Ile | Tyr | Val | Asp |
| | | | | 565 | | | | | 570 | | | | | 575 | |
| Pro | Met | Gln | Leu | Pro | Tyr | Asp | Ser | Arg | Trp | Glu | Phe | Pro | Arg | Asp | Gly |
| | | | 580 | | | | 585 | | | | | 590 | | | |
| Leu | Val | Leu | Gly | Arg | Val | Leu | Gly | Ser | Gly | Ala | Phe | Gly | Lys | Val | Val |
| | | 595 | | | | 600 | | | | | 605 | | | | |
| Glu | Gly | Thr | Ala | Tyr | Gly | Leu | Ser | Arg | Ser | Gln | Pro | Val | Met | Lys | Val |
| | 610 | | | | | 615 | | | | 620 | | | | | |
| Ala | Val | Lys | Met | Leu | Lys | Pro | Thr | Ala | Arg | Ser | Ser | Glu | Lys | Gln | Ala |
| 625 | | | | 630 | | | | | 635 | | | | | 640 | |
| Leu | Met | Ser | Glu | Leu | Lys | Ile | Met | Thr | His | Leu | Gly | Pro | His | Leu | Asn |
| | | | 645 | | | | | 650 | | | | | 655 | | |
| Ile | Val | Asn | Leu | Leu | Gly | Ala | Cys | Thr | Lys | Ser | Gly | Pro | Ile | Tyr | Ile |
| | | 660 | | | | | 665 | | | | | 670 | | | |
| Ile | Thr | Glu | Tyr | Cys | Phe | Tyr | Gly | Asp | Leu | Val | Asn | Tyr | Leu | His | Lys |
| | 675 | | | | | 680 | | | | | 685 | | | | |
| Asn | Arg | Asp | Ser | Phe | Leu | Ser | His | His | Pro | Glu | Lys | Pro | Lys | Lys | Glu |
| | 690 | | | | | 695 | | | | 700 | | | | | |
| Leu | Asp | Ile | Phe | Gly | Leu | Asn | Pro | Ala | Asp | Glu | Ser | Thr | Arg | Ser | Tyr |
| 705 | | | | 710 | | | | | 715 | | | | | 720 | |
| Val | Ile | Leu | Ser | Phe | Glu | Asn | Asn | Gly | Asp | Tyr | Met | Asp | Met | Lys | Gln |
| | | | | 725 | | | | | 730 | | | | | 735 | |
| Ala | Asp | Thr | Thr | Gln | Tyr | Val | Pro | Met | Leu | Glu | Arg | Lys | Glu | Val | Ser |
| | | | 740 | | | | | 745 | | | | | 750 | | |
| Lys | Tyr | Ser | Asp | Ile | Gln | Arg | Ser | Leu | Tyr | Asp | Arg | Pro | Ala | Ser | Tyr |
| | | 755 | | | | | 760 | | | | | 765 | | | |
| Lys | Lys | Lys | Ser | Met | Leu | Asp | Ser | Glu | Val | Lys | Asn | Leu | Leu | Ser | Asp |
| | 770 | | | | | 775 | | | | | 780 | | | | |
| Asp | Asn | Ser | Glu | Gly | Leu | Thr | Leu | Leu | Asp | Leu | Leu | Ser | Phe | Thr | Tyr |
| 785 | | | | | 790 | | | | | 795 | | | | | 800 |
| Gln | Val | Ala | Arg | Gly | Met | Glu | Phe | Leu | Ala | Ser | Lys | Asn | Cys | Val | His |
| | | | | 805 | | | | | 810 | | | | | 815 | |
| Arg | Asp | Leu | Ala | Ala | Arg | Asn | Val | Leu | Leu | Ala | Gln | Gly | Lys | Ile | Val |
| | | | 820 | | | | | 825 | | | | | 830 | | |
| Lys | Ile | Cys | Asp | Phe | Gly | Leu | Ala | Arg | Asp | Ile | Met | His | Asp | Ser | Asn |
| | | 835 | | | | | 840 | | | | | 845 | | | |
| Tyr | Val | Ser | Lys | Gly | Ser | Thr | Phe | Leu | Pro | Val | Lys | Trp | Met | Ala | Pro |
| | 850 | | | | | 855 | | | | | 860 | | | | |
| Glu | Ser | Ile | Phe | Asp | Asn | Leu | Tyr | Thr | Thr | Leu | Ser | Asp | Val | Trp | Ser |
| 865 | | | | | 870 | | | | | 875 | | | | | 880 |
| Tyr | Gly | Ile | Leu | Leu | Trp | Glu | Ile | Phe | Ser | Leu | Gly | Gly | Thr | Pro | Tyr |
| | | | | 885 | | | | | 890 | | | | | 895 | |
| Pro | Gly | Met | Met | Val | Asp | Ser | Thr | Phe | Tyr | Asn | Lys | Ile | Lys | Ser | Gly |
| | | | 900 | | | | | 905 | | | | | 910 | | |
| Tyr | Arg | Met | Ala | Lys | Pro | Asp | His | Ala | Thr | Ser | Glu | Val | Tyr | Glu | Ile |
| | | 915 | | | | | 920 | | | | | 925 | | | |
| Met | Val | Lys | Cys | Trp | Asn | Ser | Glu | Pro | Glu | Lys | Arg | Pro | Ser | Phe | Tyr |
| | 930 | | | | | 935 | | | | | 940 | | | | |
| His | Leu | Ser | Glu | Ile | Val | Glu | Asn | Leu | Leu | Pro | Gly | Gln | Tyr | Lys | Lys |
| 945 | | | | | 950 | | | | | 955 | | | | | 960 |
| Ser | Tyr | Glu | Lys | Ile | His | Leu | Asp | Phe | Leu | Lys | Ser | Asp | His | Pro | Ala |
| | | | | 965 | | | | | 970 | | | | | 975 | |
| Val | Ala | Arg | Met | Arg | Val | Asp | Ser | Asp | Asn | Ala | Tyr | Ile | Gly | Val | Thr |

-continued

| | | | | | | 980 | | | | | 985 | | | | | 990 | | |
|---|---|---|---|---|---|---|---|---|---|---|---|---|---|---|---|---|---|---|
| Tyr | Lys | Asn 995 | Glu | Glu | Asp | Lys | Leu 1000 | Lys | Asp | Trp | Glu | Gly 1005 | Gly | Leu | Asp | | | |
| Glu | Gln 1010 | Arg | Leu | Ser | Ala | Asp 1015 | Ser | Gly | Tyr | Ile | Ile 1020 | Pro | Leu | Pro | Asp | | | |
| Ile 1025 | Asp | Pro | Val | Pro | Glu 1030 | Glu | Glu | Asp | Leu | Gly 1035 | Lys | Arg | Asn | Arg | His 1040 | | | |
| Ser | Ser | Gln | Thr | Ser 1045 | Glu | Glu | Ser | Ala | Ile 1050 | Glu | Thr | Gly | Ser | Ser 1055 | Ser | | | |
| Ser | Thr | Phe | Ile 1060 | Lys | Arg | Glu | Asp | Glu 1065 | Thr | Ile | Glu | Asp | Ile 1070 | Asp | Met | | | |
| Met | Asp | Asp 1075 | Ile | Gly | Ile | Asp | Ser 1080 | Ser | Asp | Leu | Val | Glu 1085 | Asp | Ser | Phe | | | |
| Leu | | | | | | | | | | | | | | | | | | |